(12) United States Patent
Beria et al.

(10) Patent No.: US 8,389,697 B2
(45) Date of Patent: Mar. 5, 2013

(54) ANTHRACYCLINE DERIVATIVE CONJUGATES, PROCESS FOR THEIR PREPARATION AND THEIR USE AS ANTITUMOR COMPOUNDS

(75) Inventors: Italo Beria, Milan (IT); Michele Caruso, Milan (IT); John A. Flygare, Burlingame, CA (US); Vittoria Lupi, Milan (IT); Rita Perego, Milan (IT); Paul Polakis, Mill Valley, CA (US); Andrew Polson, San Francisco, CA (US); Matteo Salsa, Novara (IT); Susan D. Spencer, Mill Valley, CA (US); Barbara Valsasina, Milan (IT)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/360,212

(22) Filed: Jan. 27, 2012

(65) Prior Publication Data

US 2012/0130059 A1 May 24, 2012

Related U.S. Application Data

(63) Continuation of application No. 12/502,433, filed on Jul. 14, 2009.

(60) Provisional application No. 61/080,944, filed on Jul. 15, 2008.

(51) Int. Cl.
*C07H 15/24* (2006.01)
(52) U.S. Cl. ................ 536/6.4; 514/26; 514/33; 514/34
(58) Field of Classification Search .................. None
See application file for complete search history.

(56) References Cited

U.S. PATENT DOCUMENTS

| | | | |
|---|---|---|---|
| 4,672,057 | A | 6/1987 | Bargiotti et al. |
| 4,826,964 | A | 5/1989 | Acton et al. |
| 5,122,368 | A | 6/1992 | Greenfield et al. |
| 5,304,687 | A | 4/1994 | Bargiotti et al. |
| 5,387,578 | A | 2/1995 | Angelucci et al. |
| 5,776,458 | A | 7/1998 | Angelucci et al. |
| 5,843,903 | A | 12/1998 | Schally et al. |
| 6,630,579 | B2 | 10/2003 | Chari et al. |
| 7,223,837 | B2 | 5/2007 | De Groot et al. |
| 7,521,541 | B2 | 4/2009 | Eigenbrot et al. |
| 2007/0060534 | A1 | 3/2007 | Matteucci et al. |
| 2008/0241128 | A1 | 10/2008 | Jeffrey |

FOREIGN PATENT DOCUMENTS

| | | |
|---|---|---|
| EP | 0294 294 B1 | 12/1988 |
| EP | 0 398 305 | 11/1990 |
| EP | 0 476 408 | 3/1992 |
| GB | 2 247 885 A | 3/1992 |
| GB | 2 296 495 A | 7/1996 |
| GB | 2 315 067 | 1/1998 |
| WO | 92/02255 | 2/1992 |
| WO | 98/02446 | 1/1998 |
| WO | 2004/067038 | 8/2004 |
| WO | 2004/082579 A2 | 9/2004 |
| WO | 2004/082689 A1 | 9/2004 |
| WO | 2005/005455 A2 | 1/2005 |
| WO | 2009/099741 A1 | 8/2009 |

OTHER PUBLICATIONS

H. Dalton King, "BR96 Conjugates of Highly Potent Anthracyclines" *Bioorganic & Medicinal Chemistry Letters, Pergamon, Elsevier Science* (XP-001193826) 13(13):2219-2822 (Jan. 1, 2003).
Jacques Robert and Luca Gianni, "Pharmacokinetics and Metabolism of Anthracyclines" *Pharamacokinetic and Metabolism of Anthracyclines* (XP-000893095) 17(1):219-252 (Jan. 1, 1993).
Martin C. Garnett, "Target drug Conjugates: principles and progress" *Advanced Drug Delivery Reviews, Elsevier Science B.V.* (XP-002261805) 52(2):171-216 (Dec. 17, 2001).
Patent Cooperation Treact (PCT), "International Search Report and Written Opinion, Dated Nov. 11, 2010, 15 pages" *International Searching Authority*.
Philip R. Hamann, "Monoclonal Antibody-drug Conjugates" *Expert Opinion on Therapeutic Patents* (XP-002606237) 15(9):1087-1103 (Sep. 2005).
Beulz-Riche et al., "Metabolism of methoxymorpholino-doxorubicin in rat, dog and monkey liver microsomes: comparison with human microsomes" *Fundam Clin Pharmacol.* 15:373-8 (2001).
Dubowchik et al., "Doxorubicin immunoconjugates containing bivalent, lysosomally-cleavable dipeptide linkages" *Bioorg Med Chem Lett.* 12:1529-32 (2002).
Jeffrey et al., "Development and properties of beta-glucuronide linkers for monoclonal antibody-drug conjugates" *Bioconjug Chem.* 17:831-40 (2006).
Jeffrey et al., "Dipeptide-based highly potent doxorubicin antibody conjugates" *Bioorganic & Med. Chem. Letters* 16:358-362 (2006).
King et al., "Monoclonal Antibody Conjugates of Doxorubicin Prepared with Branched Peptide Linkers: Inhibition of Aggregation by Methoxytriethyleneglycol Chains" *J. Med. Chem* 45:4336-4343 (2002).
Kratz et al., "Prodrugs of anthracyclines in cancer chemotherapy" *Curr Med Chem.* 13:477-523 (2006).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies" *Proc Natl Acad Sci U S A.* 94(2):829-34 (Jan. 18, 2000).
Quintieri et al., "Formation and antitumor activity of PNU-159682, a major metabolite of nemorubicin in human liver microsomes" *Clin Cancer Res.* 11:1608-17 (Feb. 15, 2005).
Sessa et al., "Ongoing phase I and II studies of novel anthracyclines" *Cardiovasc Toxicol.* 7:75-9 (2007).
Torgov et al., "Generation of an intensely potent anthracycline by a monoclonal antibody-beta-galactosidase conjugate" *Bioconjug Chem.* 16:717-21 (2005).

*Primary Examiner* — Patrick Lewis
(74) *Attorney, Agent, or Firm* — Alex Andrus; Genentech, Inc.

(57) ABSTRACT

The present invention relates to conjugates of therapeutically useful anthracyclines with carriers such as polyclonal and monoclonal antibodies, proteins or peptides of natural or synthetic origin; methods for their preparation, pharmaceutical composition containing them and use thereof in treating certain mammalian tumors.

15 Claims, 27 Drawing Sheets

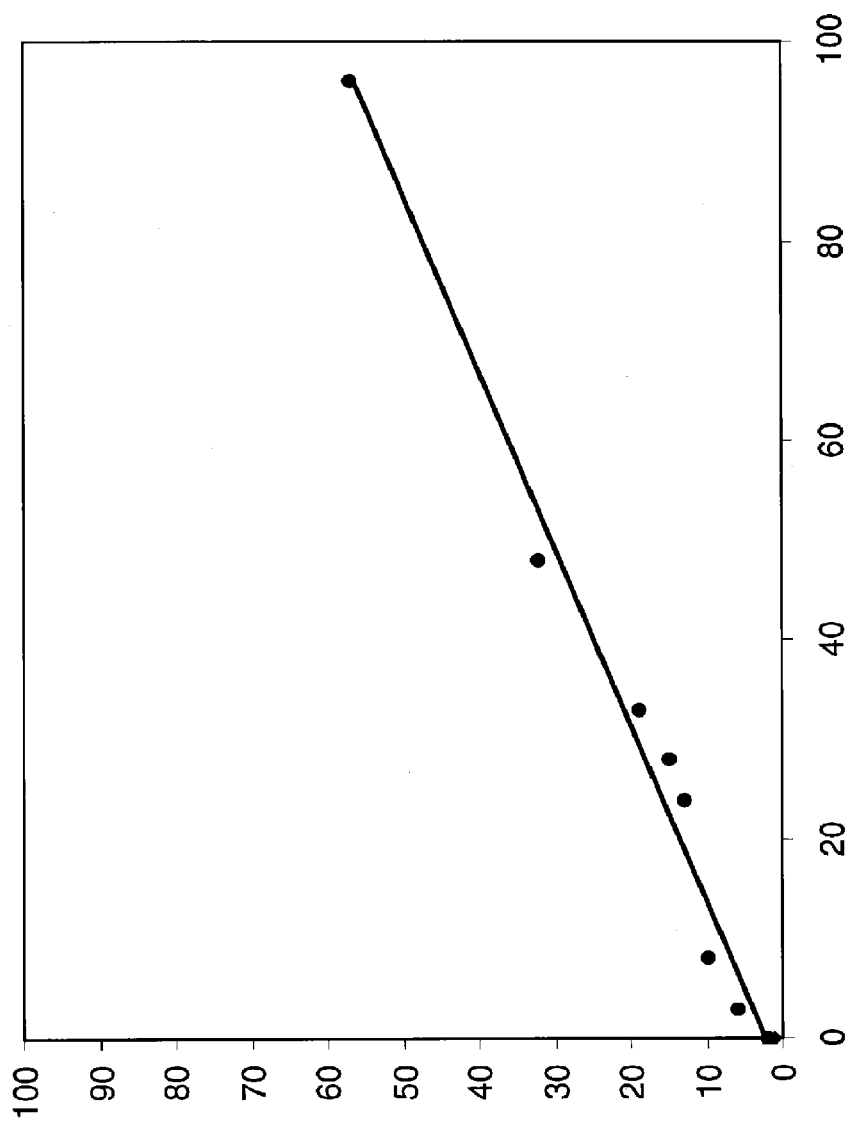
FIG._1

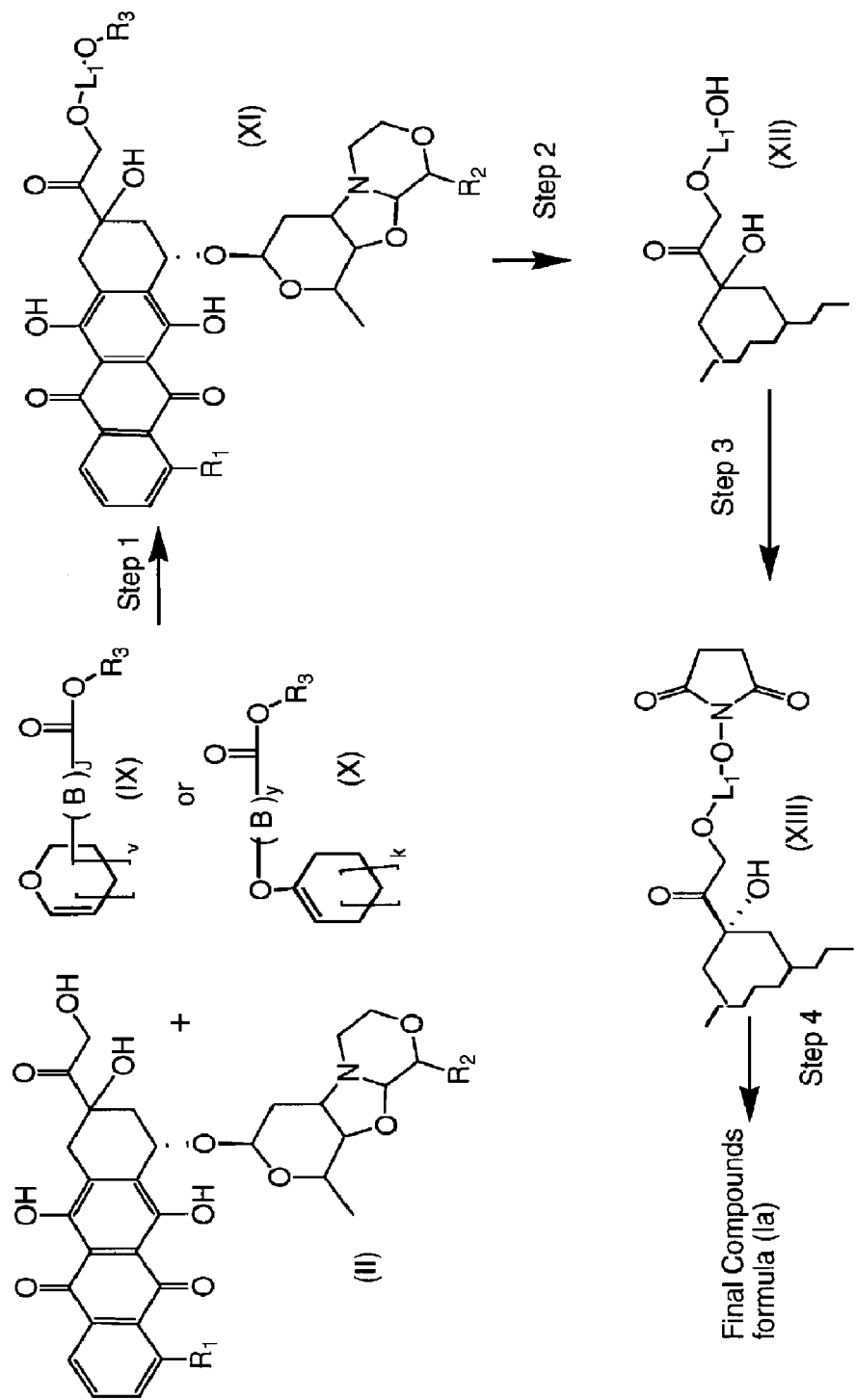
FIG._2

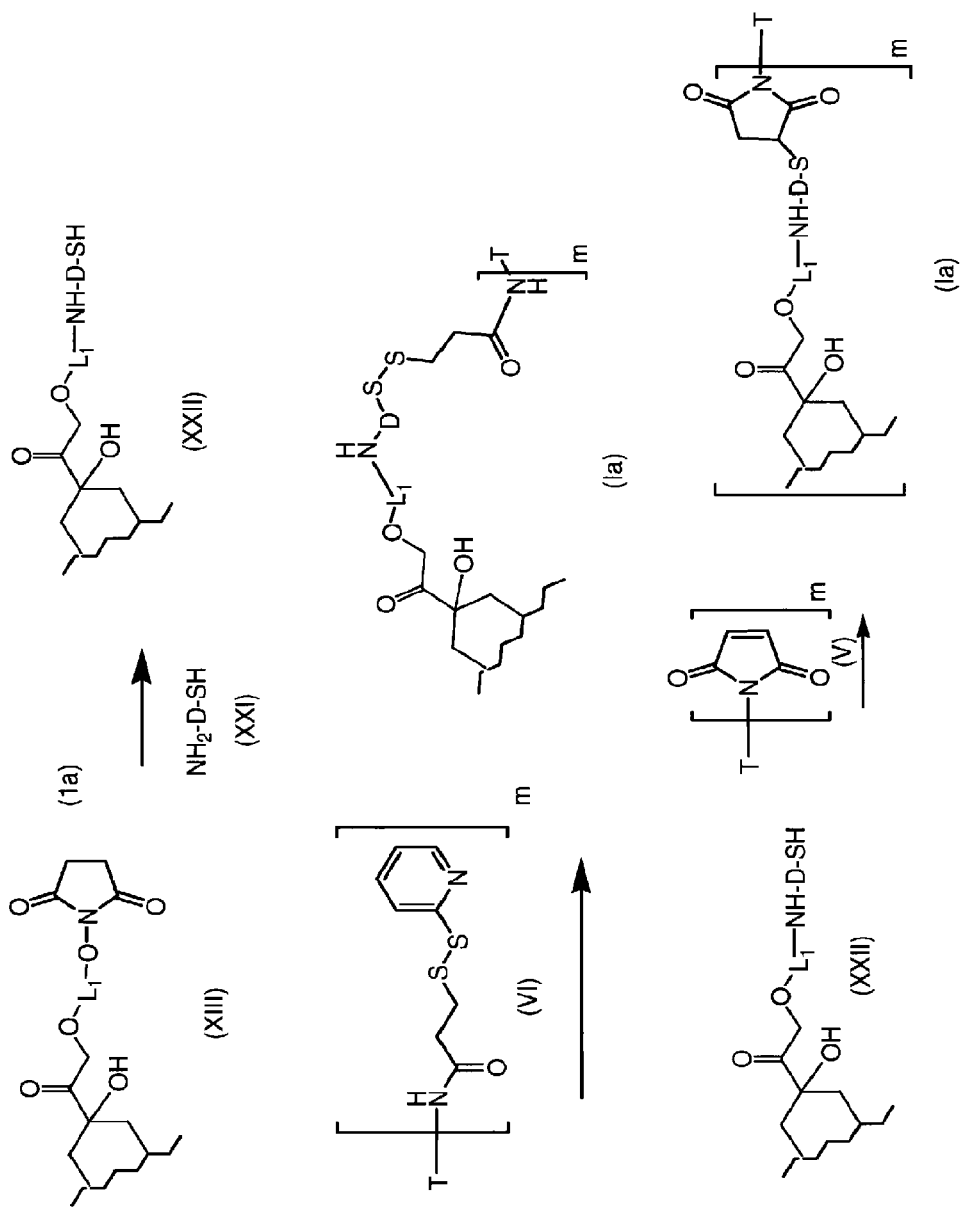
FIG._3a

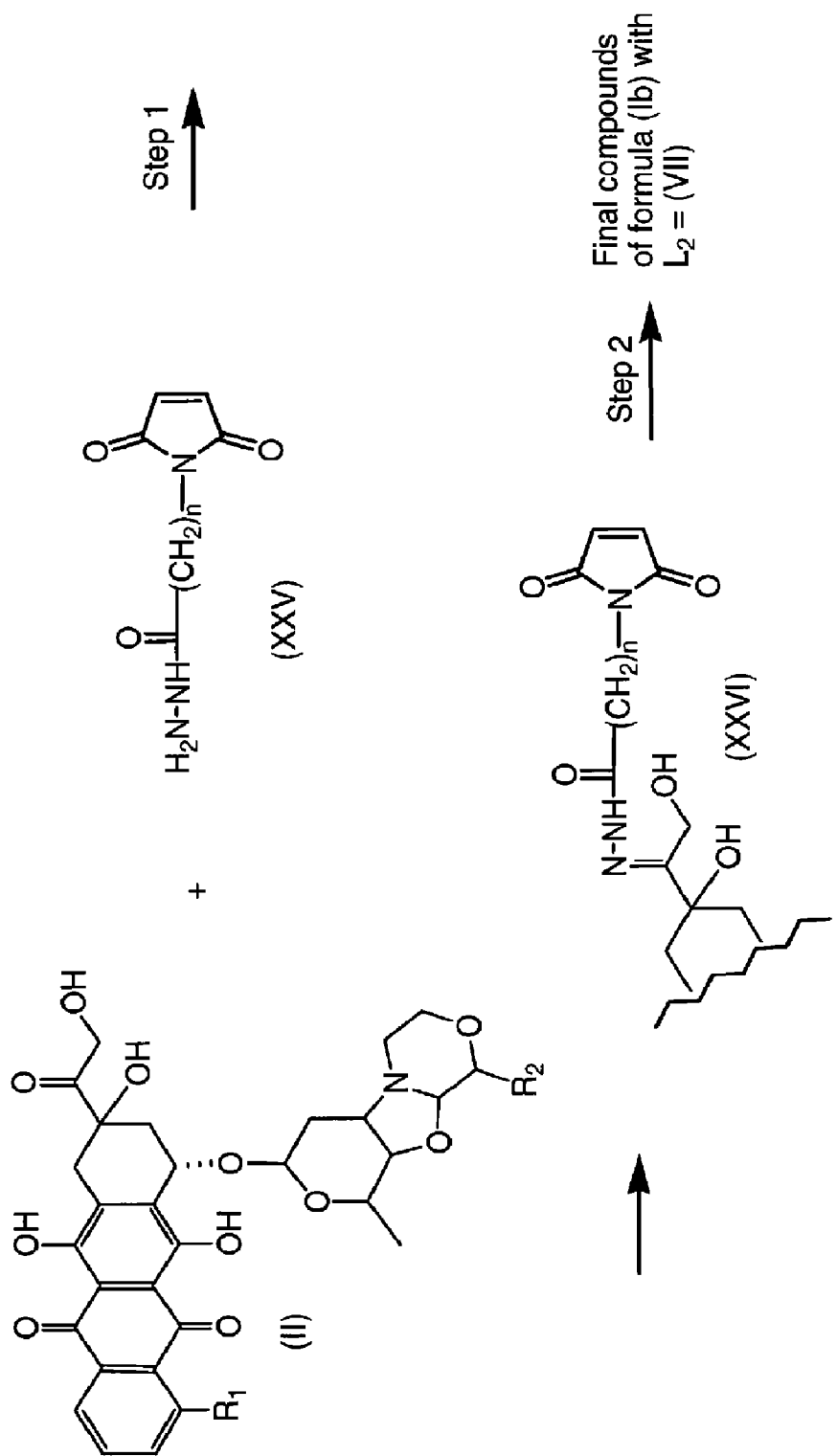
FIG._4

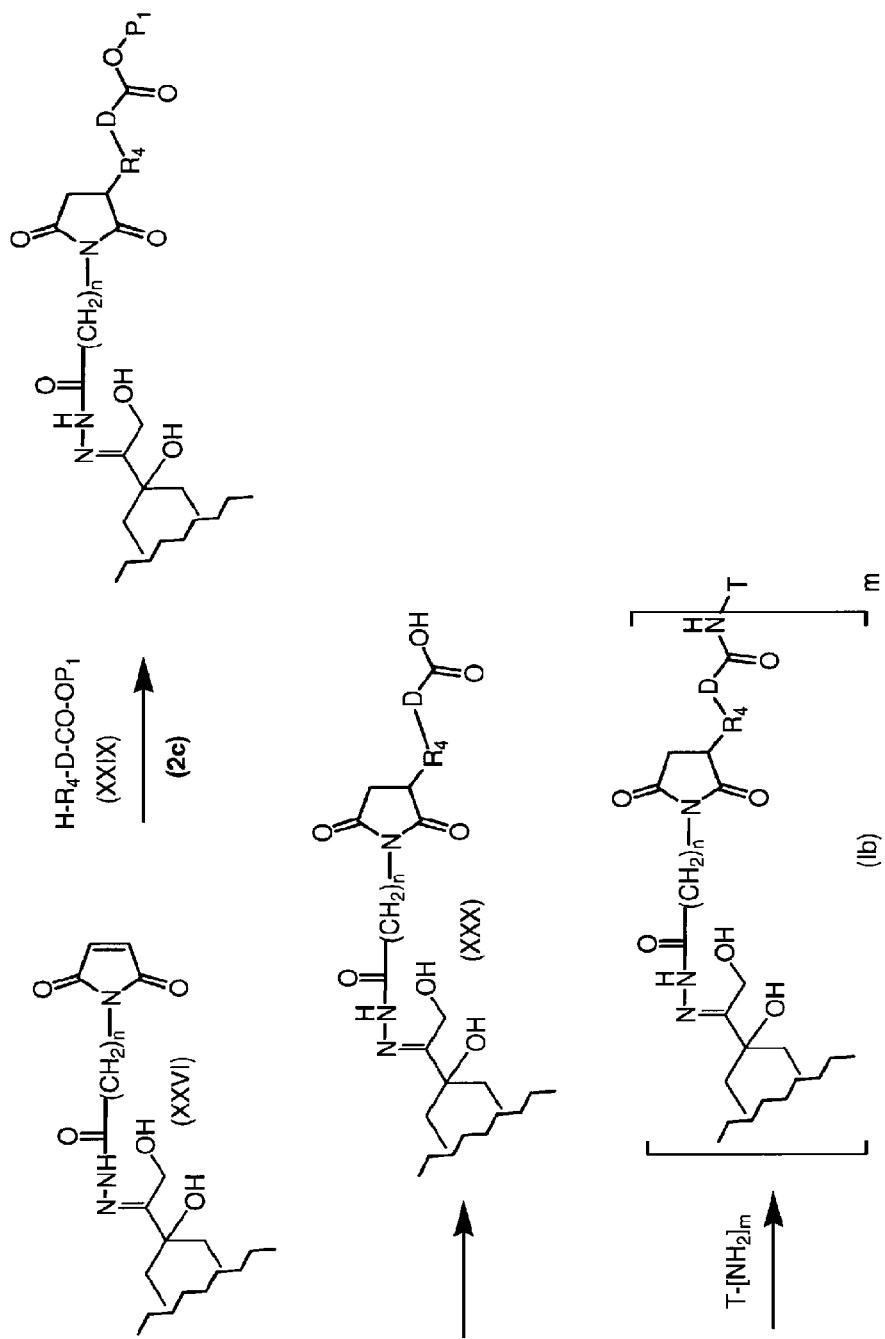
FIG._5b

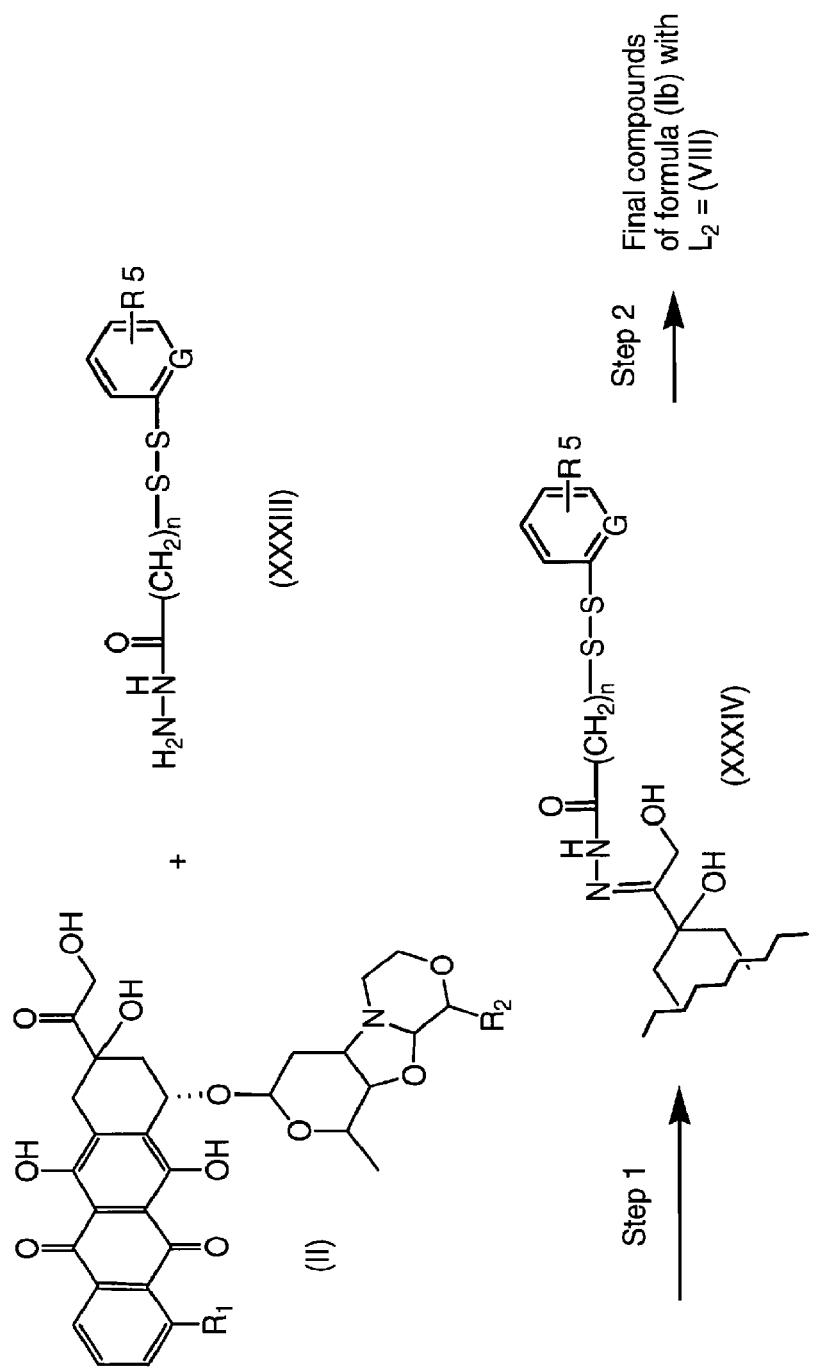
FIG._6

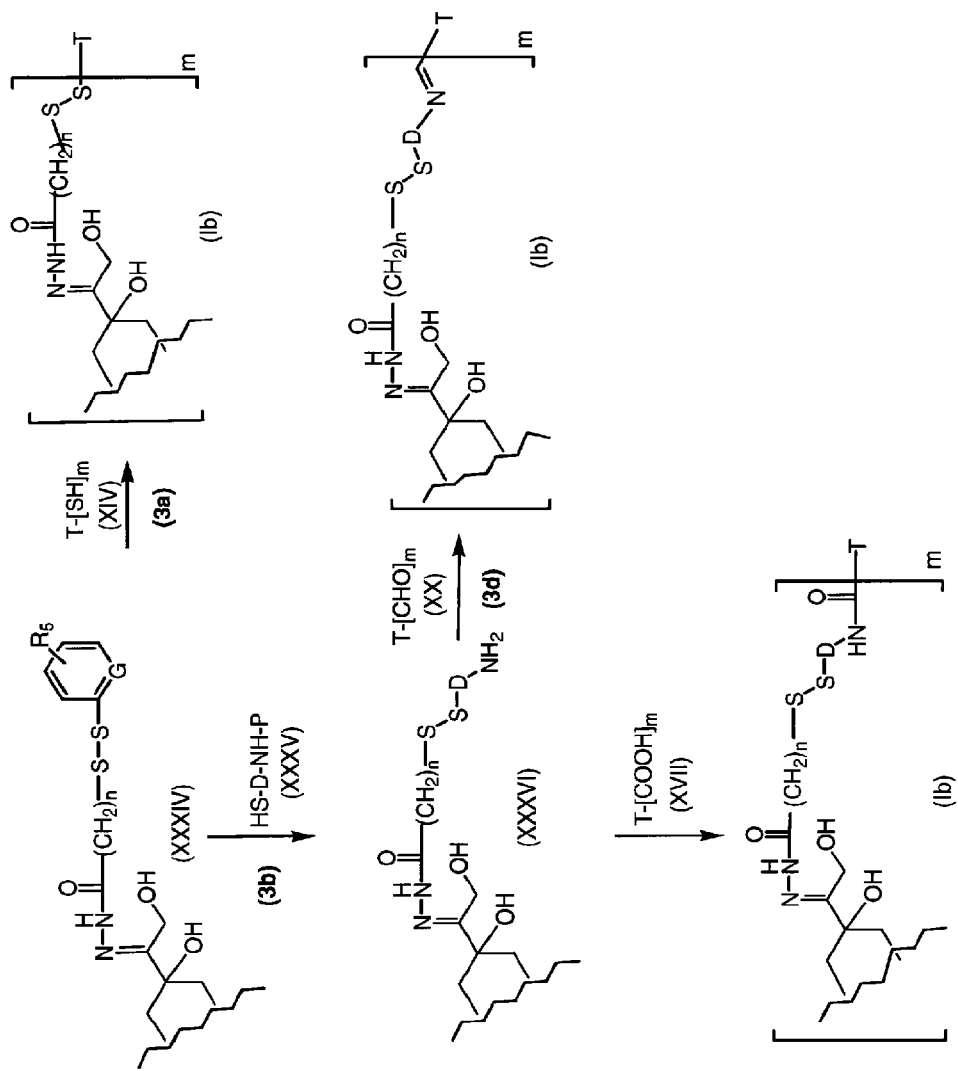
FIG._7a

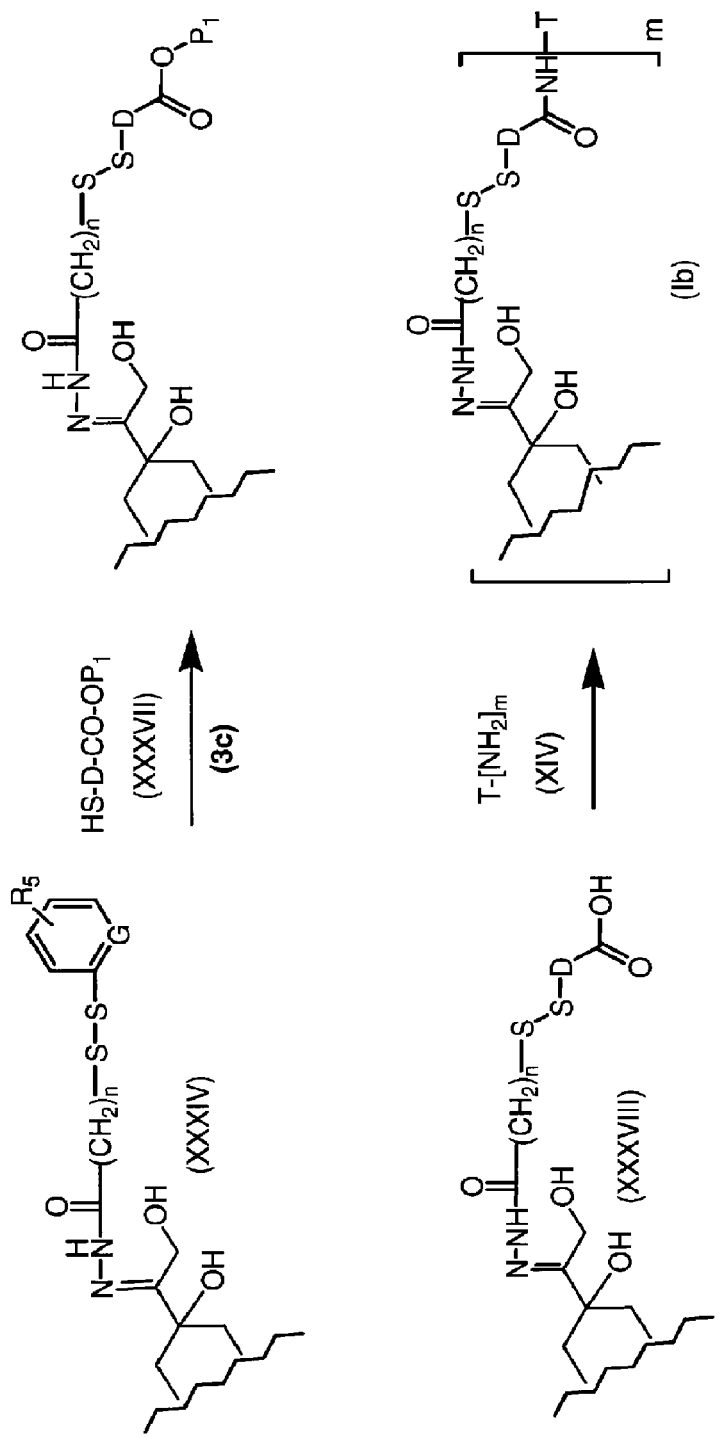
FIG. _7b

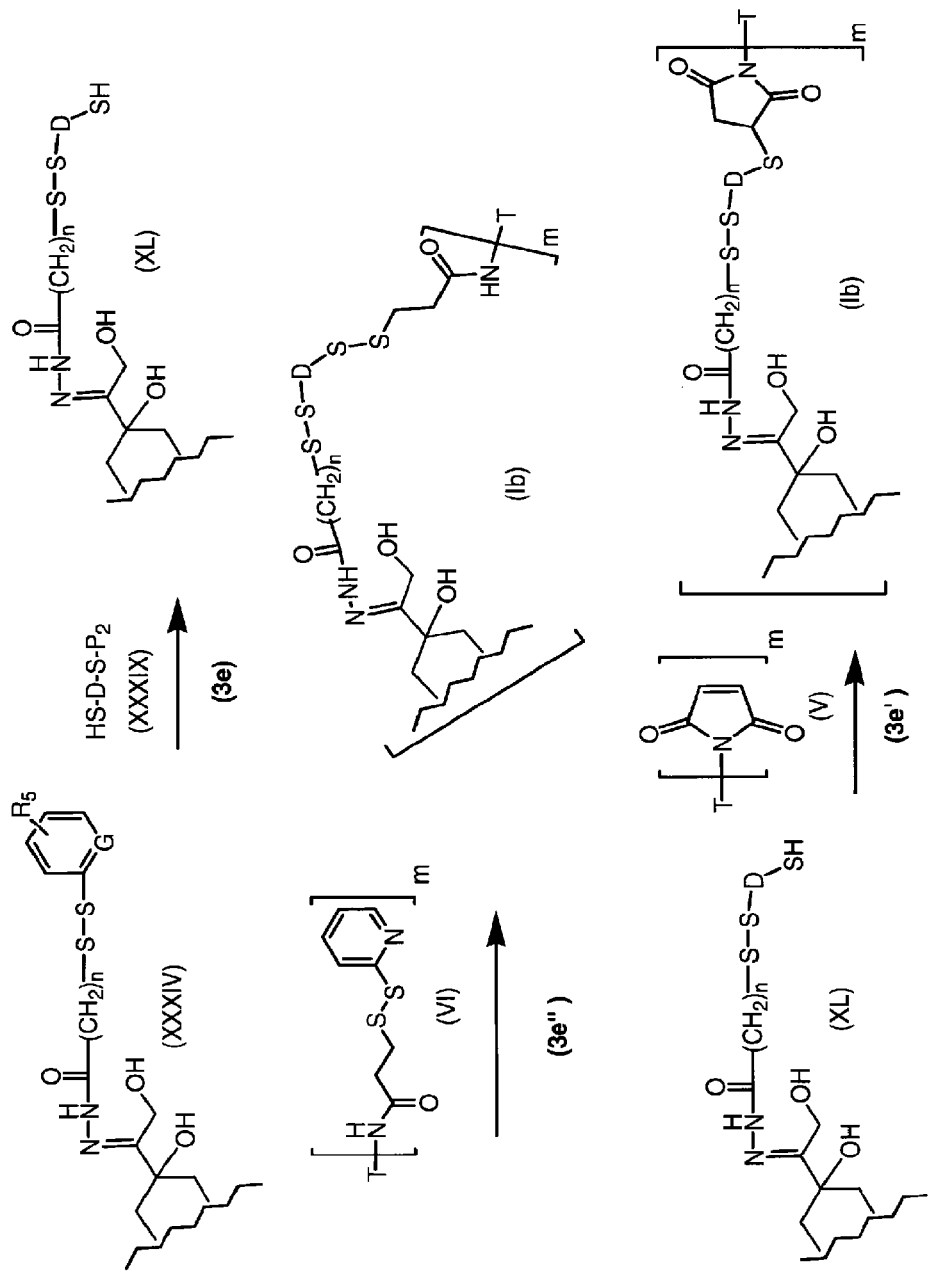
FIG._7c

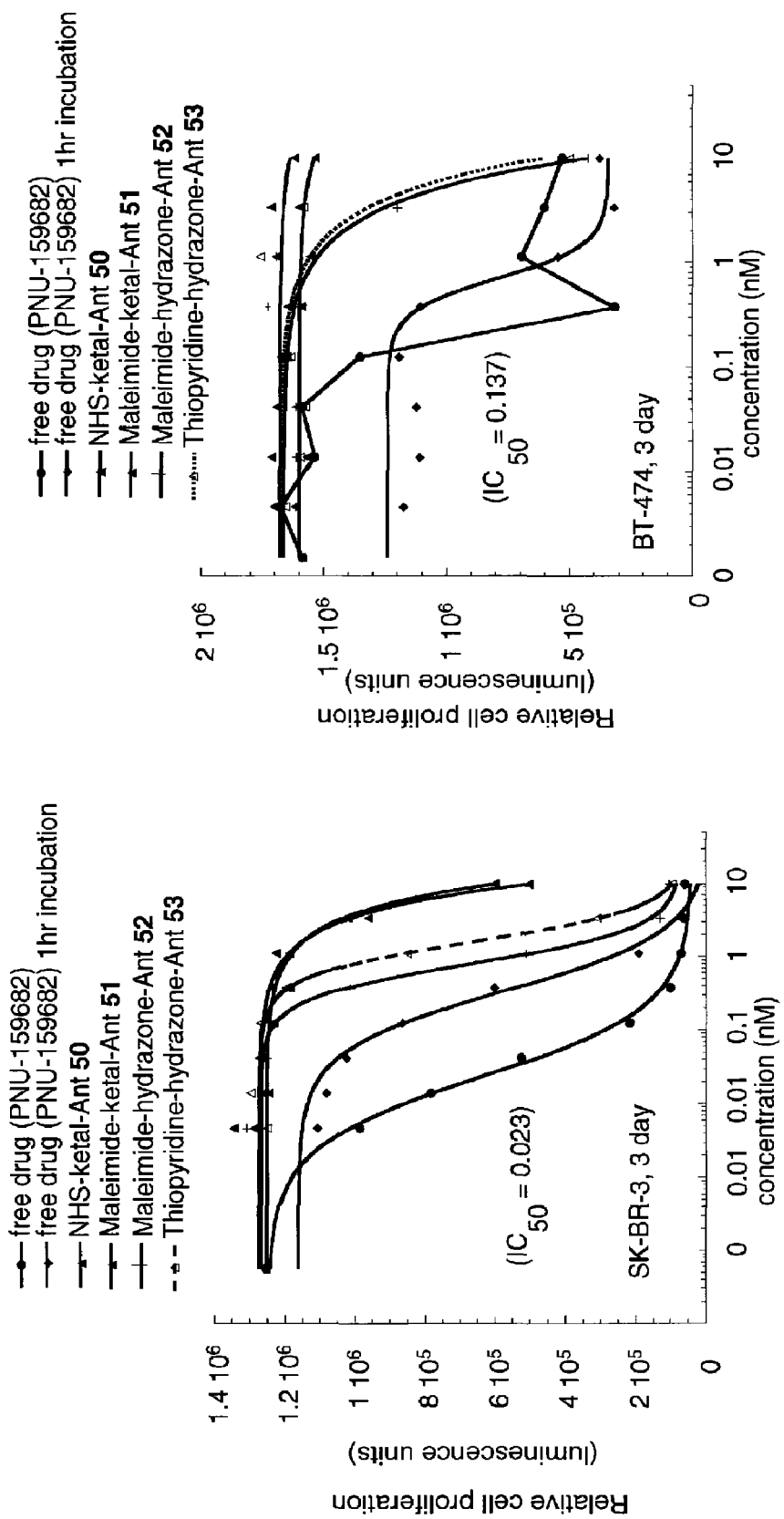

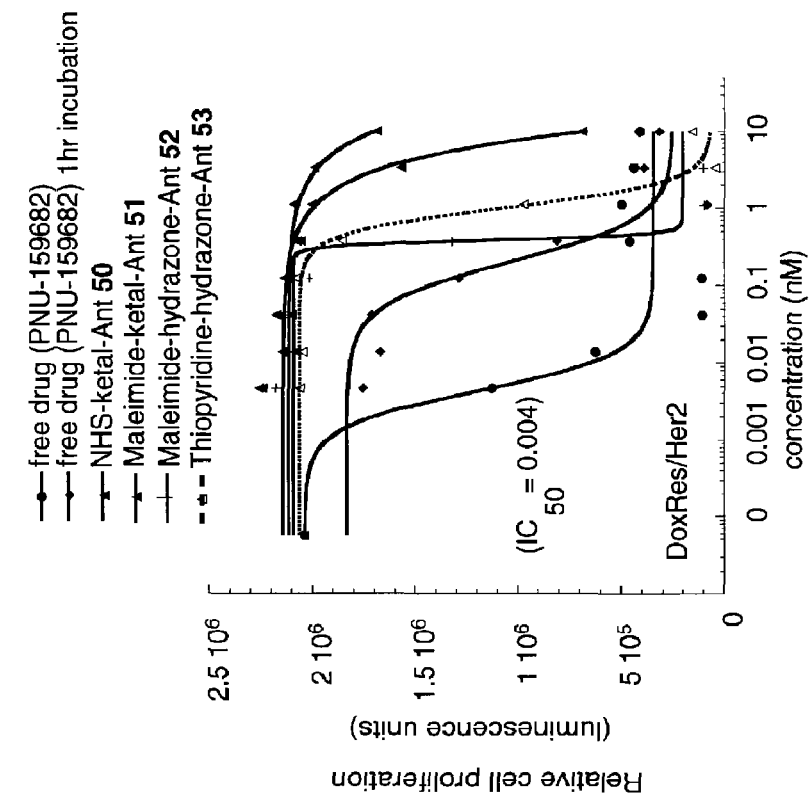
FIG._11
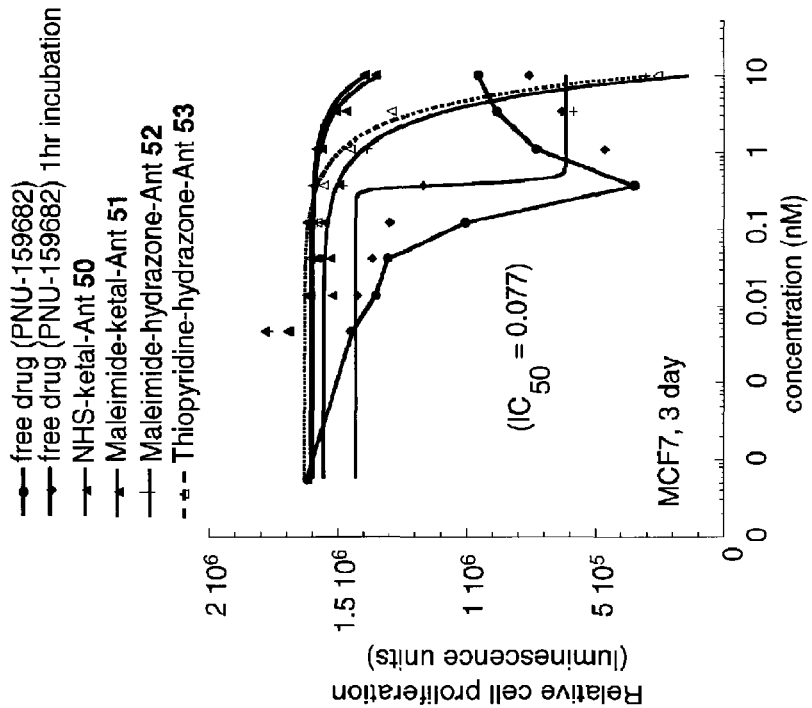
FIG._10

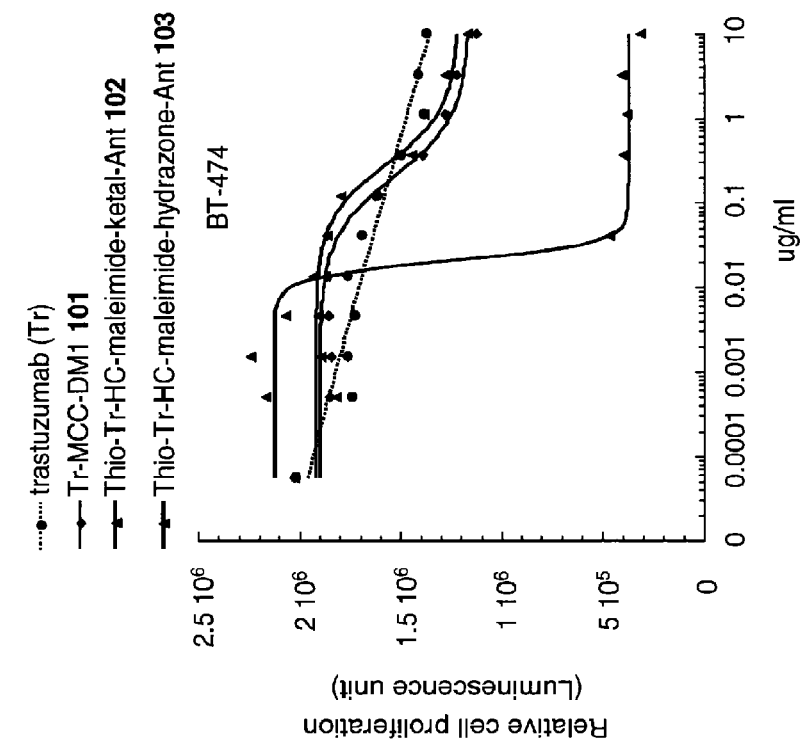
FIG._13
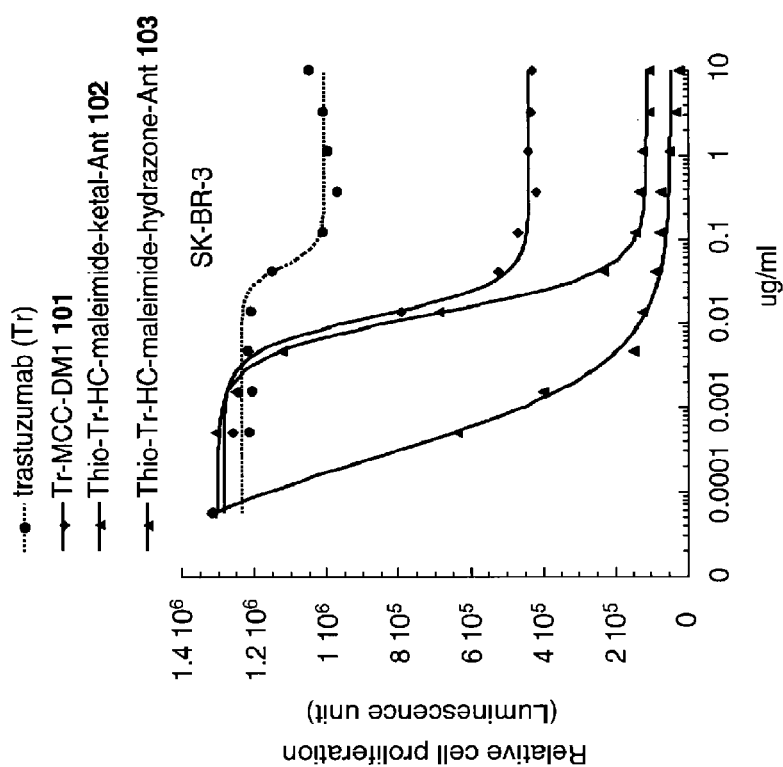
FIG._12

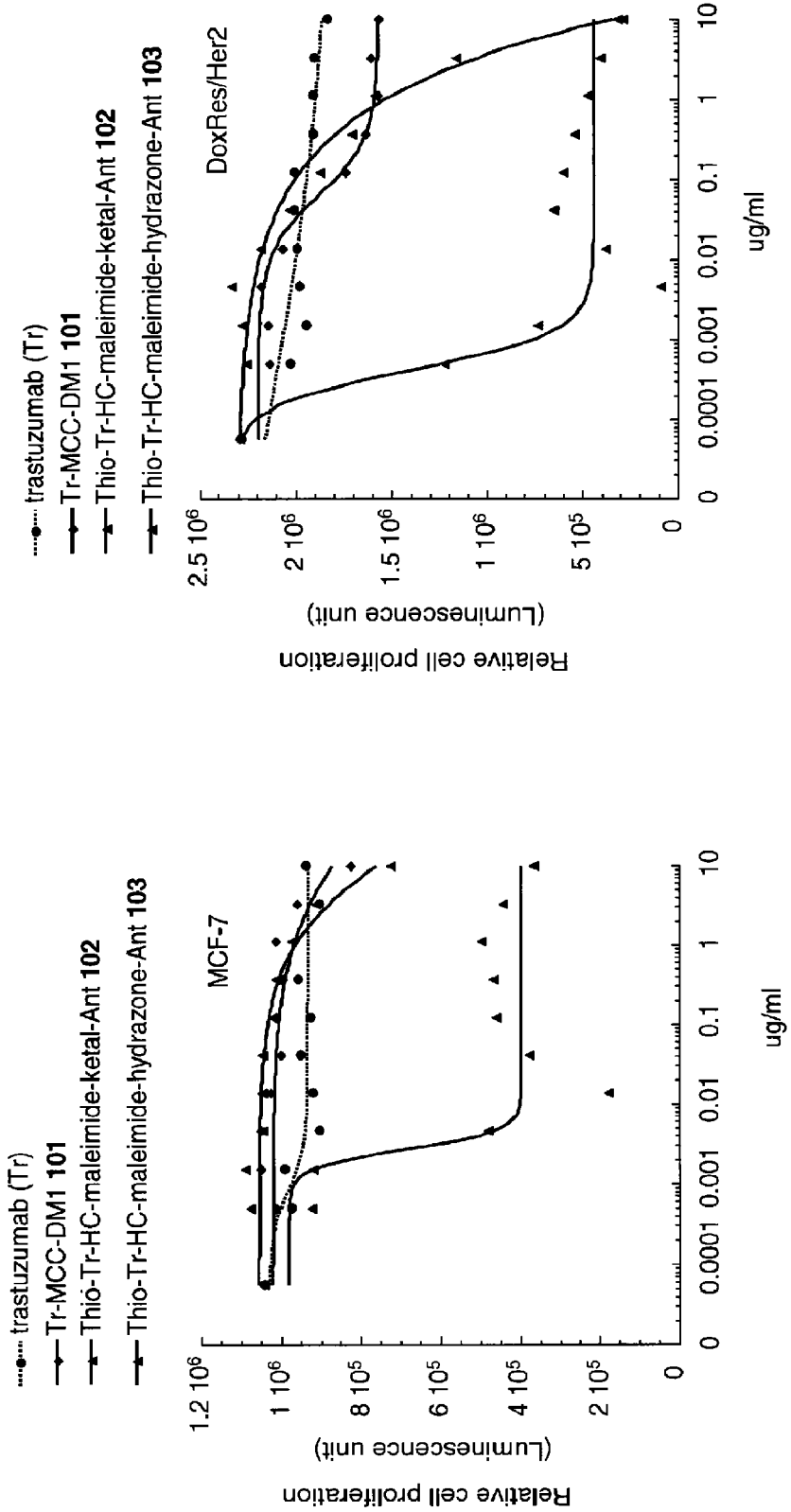
FIG._14
FIG._15

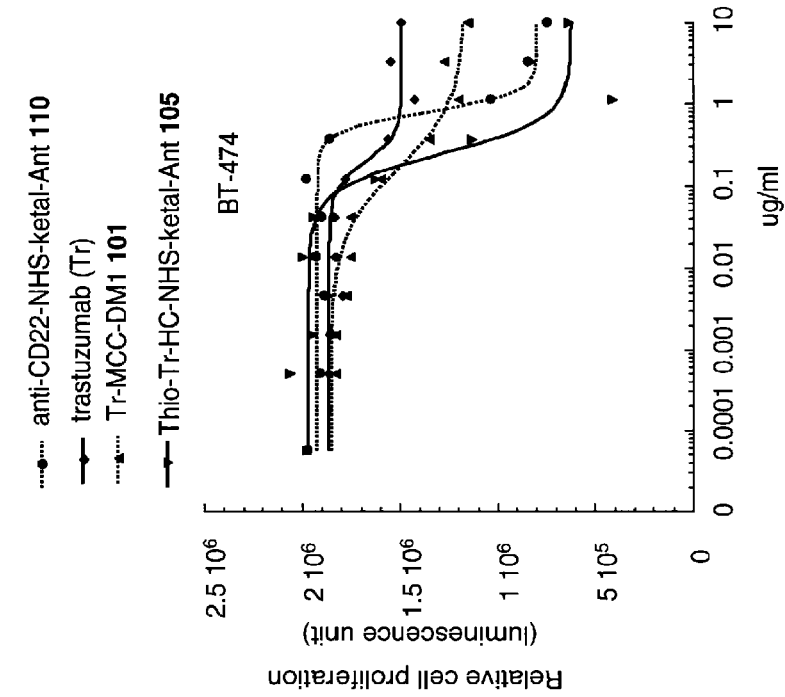
FIG._17
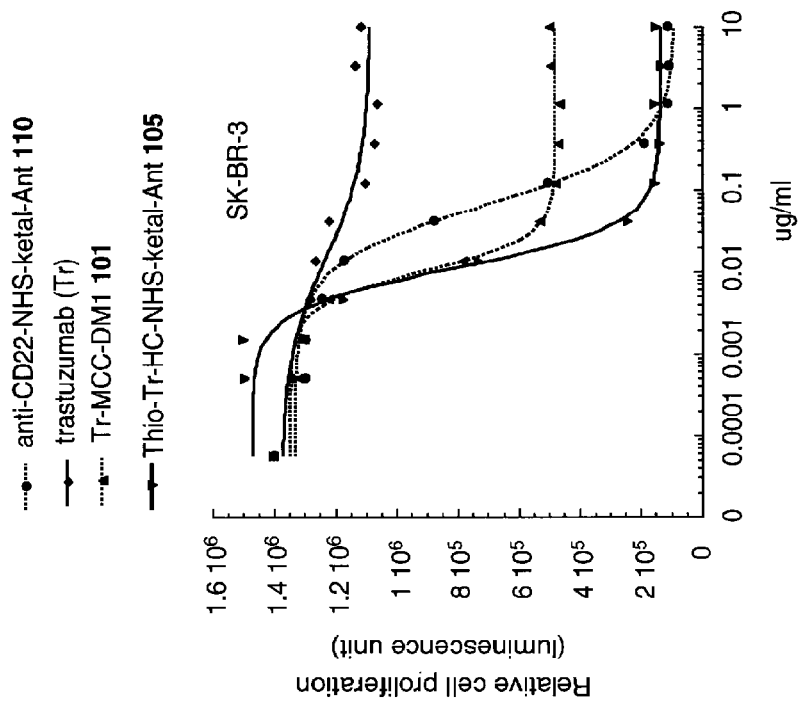
FIG._16

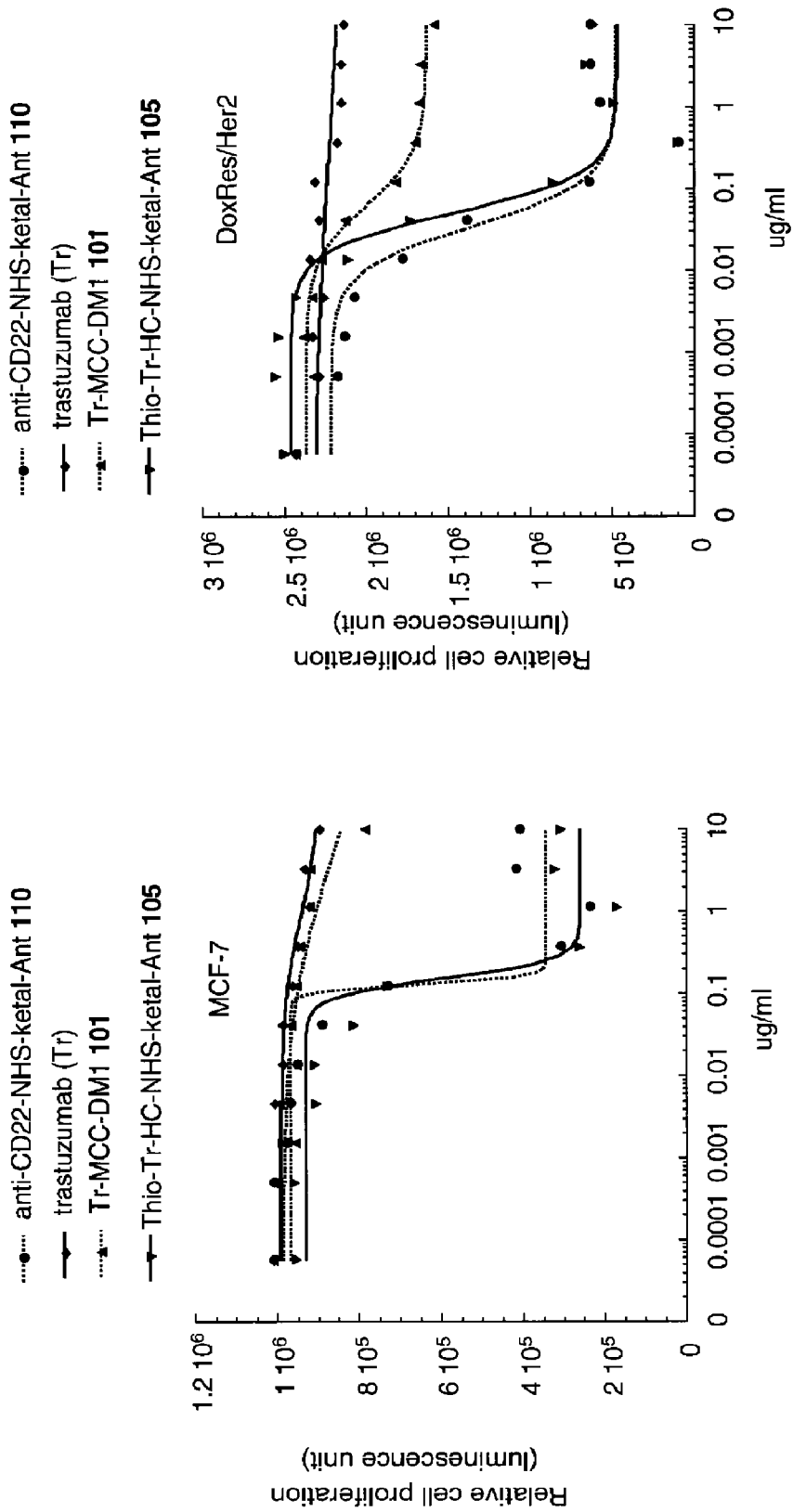
FIG._18
FIG._19

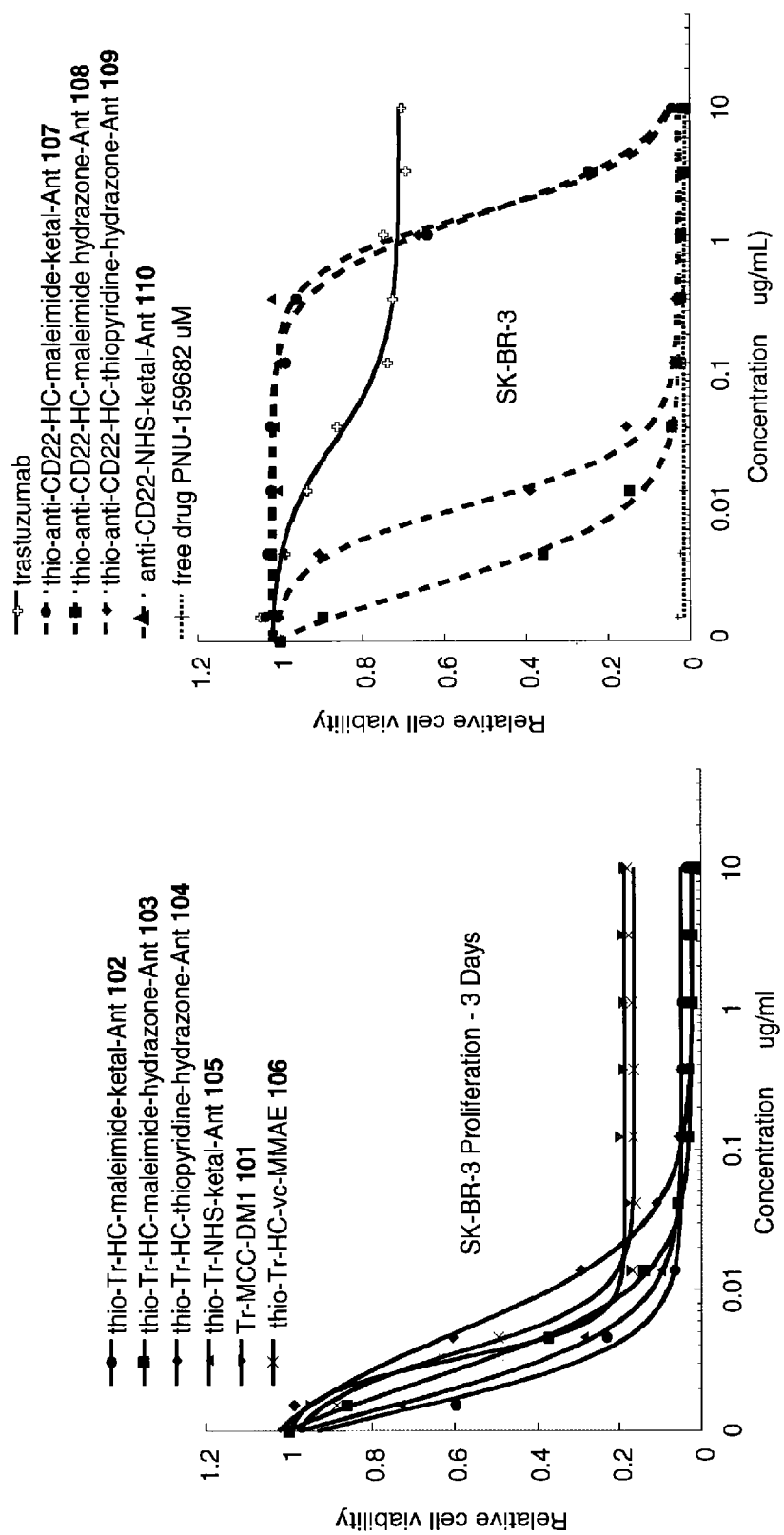
FIG._21
FIG._20

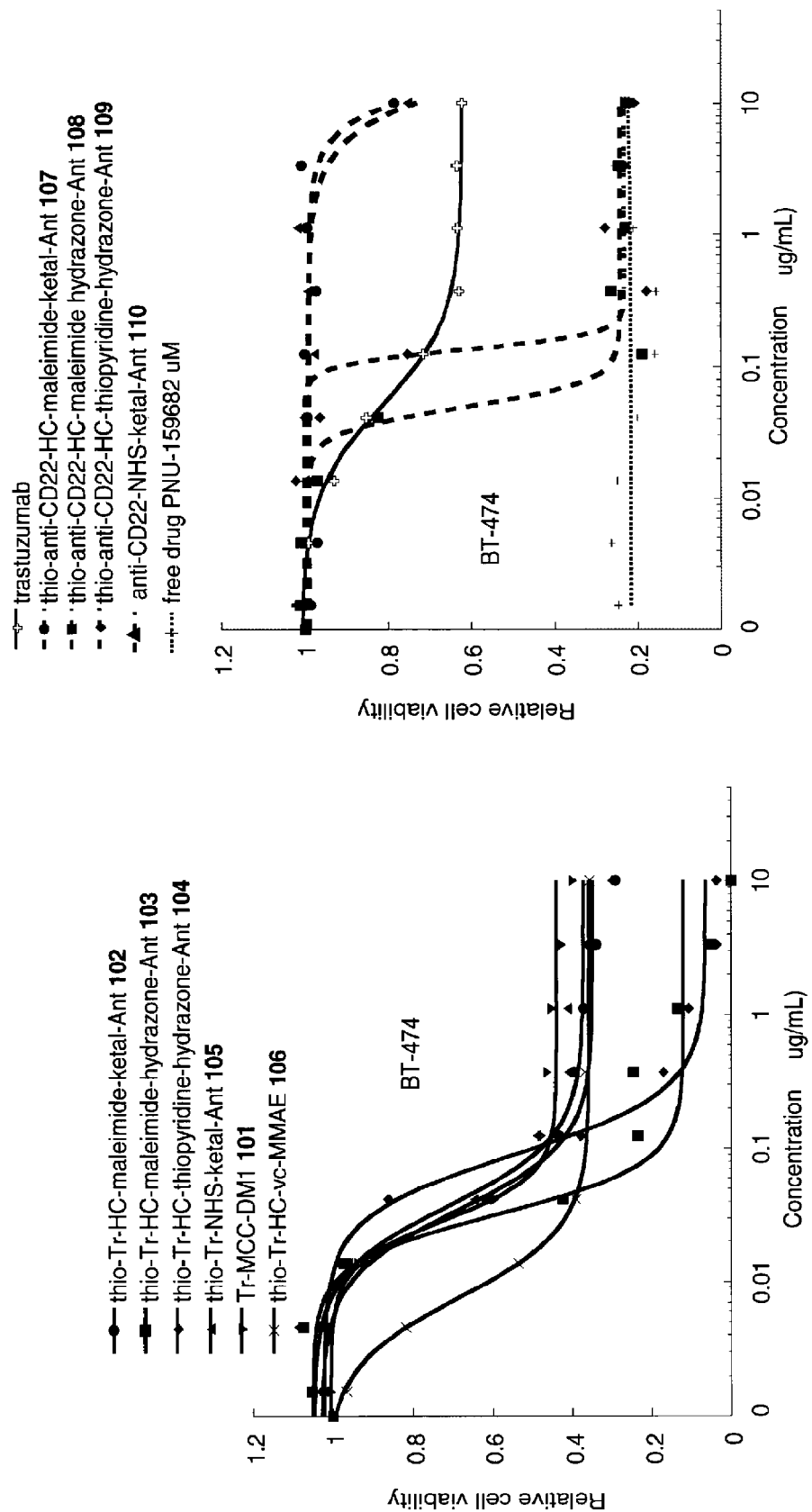
FIG._23
FIG._22

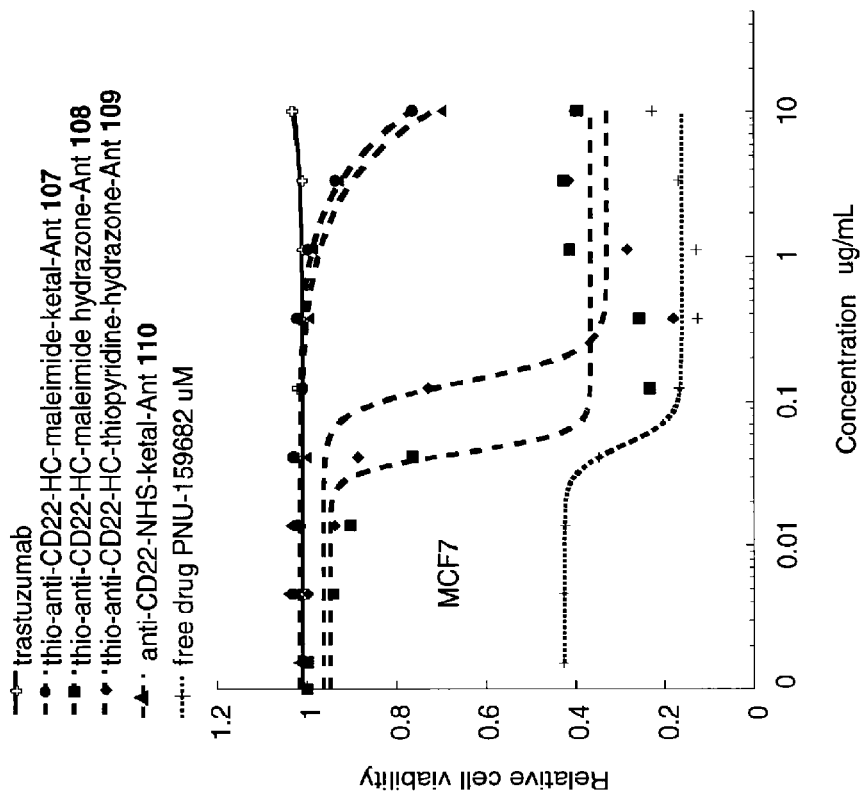
FIG._25
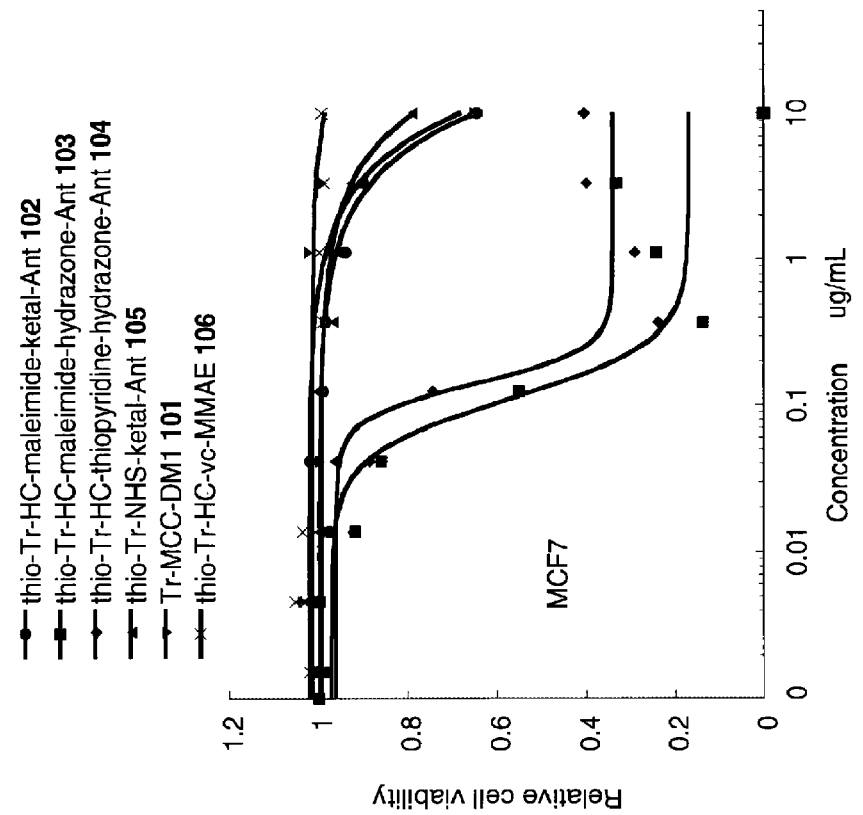
FIG._24

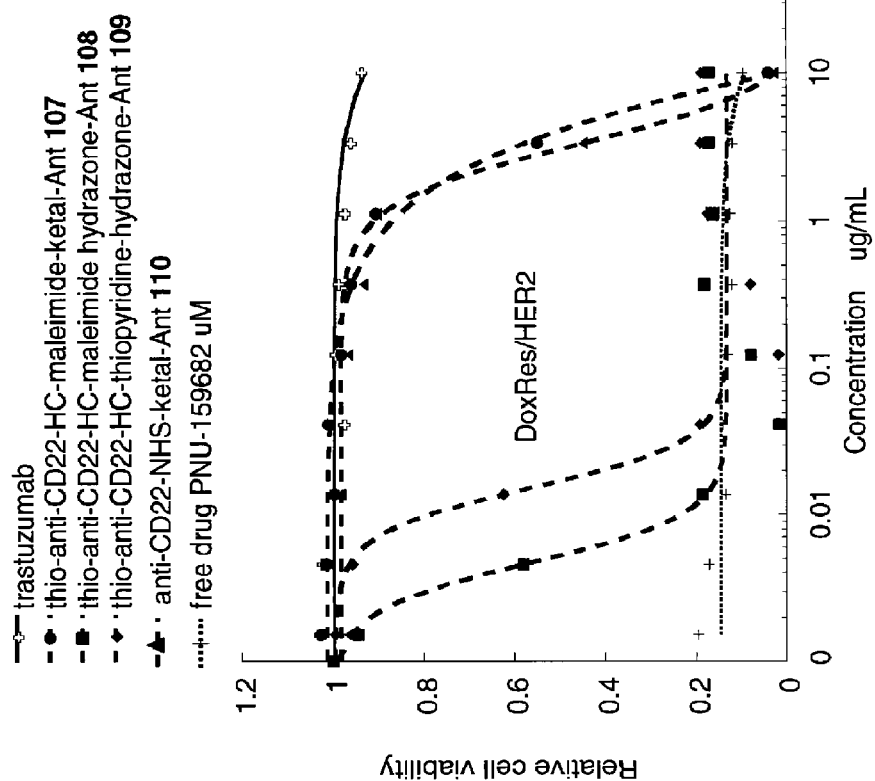
FIG._27
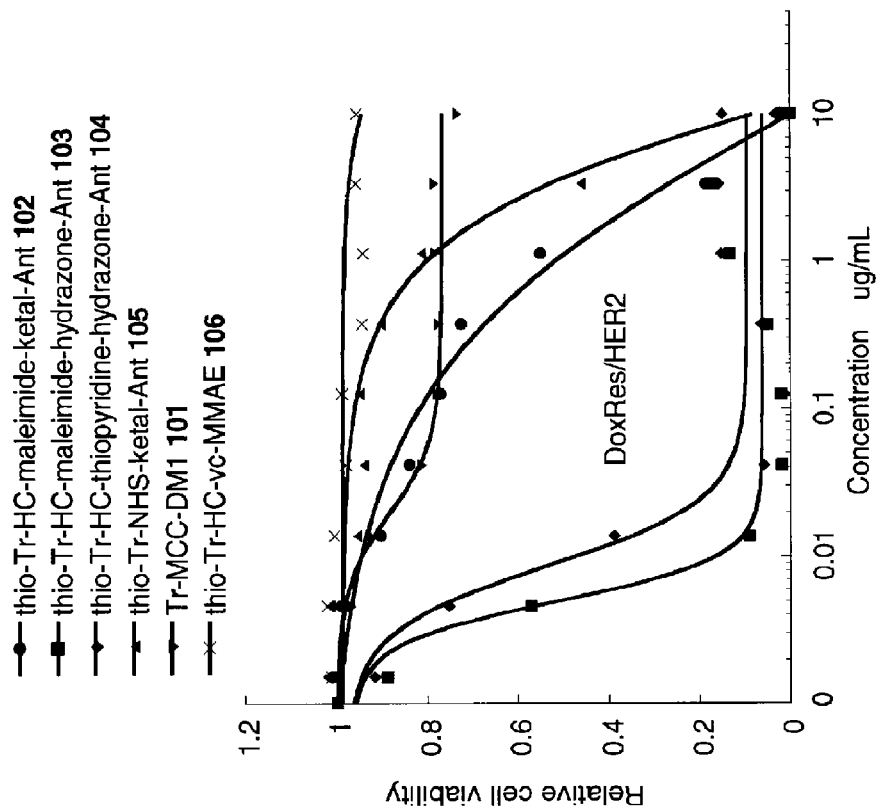
FIG._26

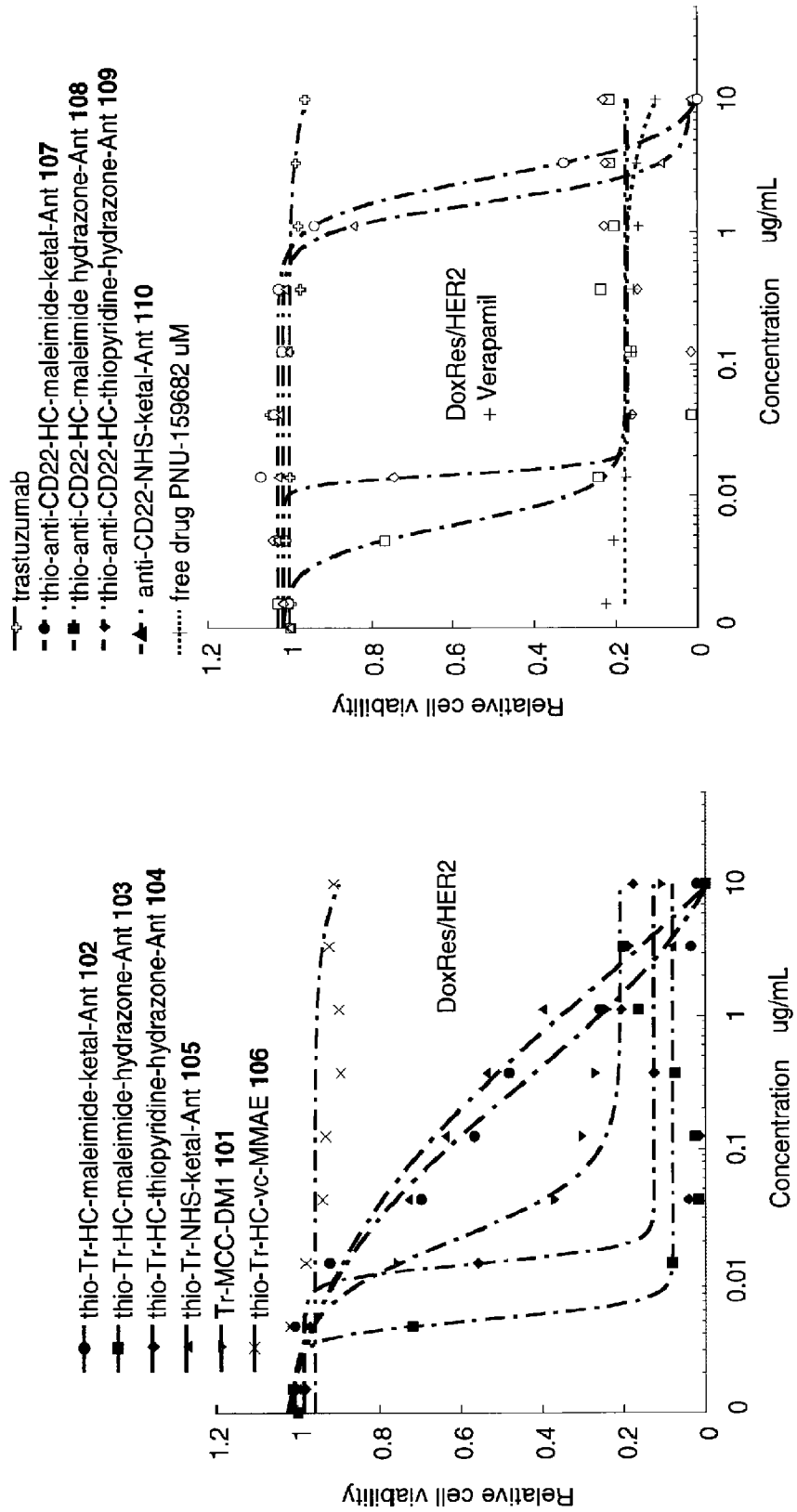
FIG._29
FIG._28

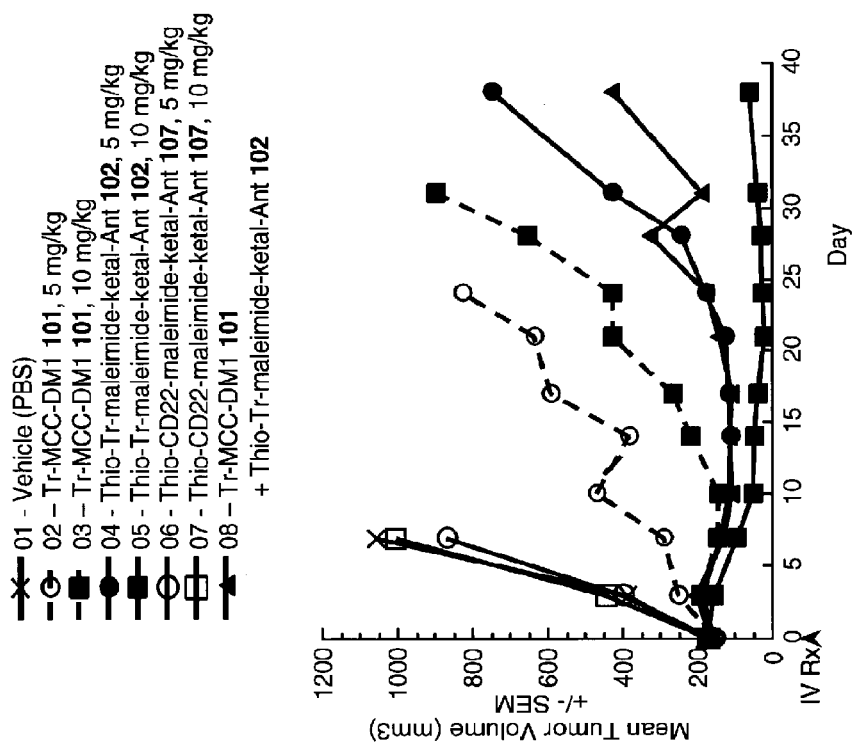
FIG._31
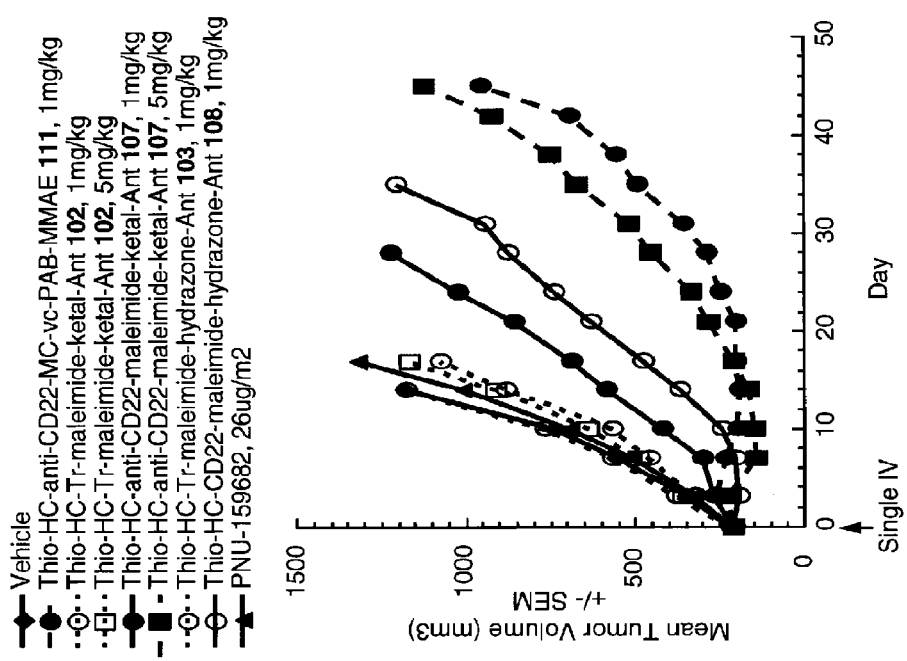
FIG._30

ANTHRACYCLINE DERIVATIVE CONJUGATES, PROCESS FOR THEIR PREPARATION AND THEIR USE AS ANTITUMOR COMPOUNDS

CROSS REFERENCE TO RELATED APPLICATIONS

This application is a continuation of U.S. Ser. No. 12/502,433 filed on 14 Jul. 2009, and also claims the benefit under 35 USC §119(e) of U.S. Provisional Application Ser. No. 61/080,944 filed on 15 Jul. 2008, which is incorporated by reference in entirety.

FIELD OF THE INVENTION

The present invention relates to conjugates of therapeutically useful anthracyclines with carriers such as polyclonal and monoclonal antibodies, proteins or peptides of natural or synthetic origin; methods for their preparation, pharmaceutical composition containing them and use thereof in treating certain mammalian tumors. The invention also relates to new anthracycline derivatives and to their preparation.

BACKGROUND OF THE INVENTION

Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H-Wiernik, in *Anthracycline: Current Status And New Developments* p 11]. Commonly used anthracyclines include doxorubicin, epirubicin, idarubicin and daunomycin.

In the recent years many new highly cytotoxic anthracyclines have been synthesized. For example nemorubicin, the anthracycline derivative bearing a substituted morpholino ring linked to the C-3' position of the sugar moiety has shown promising antitumor activity on experimental murine tumors [see: J. W. Lown, Bioactive Molecules (1988) vol 6:55-101] and is currently under clinical phase trials for the treatment of hepatocellular carcinoma [see: C. Sessa, O. Valota, C. Geroni, Cardiovascular Toxicology (2007) 7(2):75-79]. Although these compounds may be useful in the treatment of neoplasm and other disease states wherein a selected cell population is sought to be eliminated, their therapeutic efficacy is often limited by the dose-dependent toxicity associated with their administration.

Attempts to improve the therapeutic effect of these compounds have been tried by linking the anthracycline to antibodies or to different carriers. An example of an anthracycline conjugated with antibodies is reported, for example, in EP 0328147 to Bristol Myers, in WO 9202255 to Farmitalia Carlo Erba or in U.S. Pat. No. 5,776,458 to Pharmacia & Upjohn.

Other interesting tricyclic morpholino anthracycline derivatives, characterized by high activity, were described and claimed in the International patent application WO 98/02446 (1997) of M. Caruso et al. Among these derivatives, a particularly active compound is PNU-159682, described by Quintieri, L., Geroni, C. et al. in Clinical Cancer Research (2005) 11(4):1608-1617. Compound PNU-159682 has the formula (IIA) as defined herein below, and the following chemical names:

5,12-naphthacenedione, 7,8,9,10-tetrahydro-6,8,11-trihydroxy-8-(hydroxyacetyl)-1-methoxy-10-[[(1S,3R,4aS,9S,9aR,10aS)-octahydro-9-methoxy-1-methyl-1H-pyrano[4',3':4,5]oxazolo[2,3-c][1,4]oxazin-3-yl]oxy]-, (8S,10S)-(9CI);

5,12-naphthacenedione, 7,8,9,10-tetrahydro-6,8,11-trihydroxy-8-(hydroxyacetyl)-1-methoxy-10-[(octahydro-9-methoxy-1-methyl-1H-pyrano[4',3':4,5]oxazolo[2,3-c][1,4]oxazin-3-yl)oxy]-, [1S-[1α,3β(8R*,10R*),4aβ,9α,9aα,10aβ]] or (8S,10S)-6,8,1'-trihydroxy-8-(hydroxyacetyl)-1-methoxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione.

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells as well as the tumor cells sought to be eliminated (Xie et al (2006) Expert. Opin. Biol. Ther. 6(3):281-291; Kovtun et al (2006) Cancer Res. 66(6):3214-3121; Law et al (2006) Cancer Res. 66(4):2328-2337; Wu et al (2005) Nature Biotech. 23(9):1137-1145; Lambert J. (2005) Current Opin. in Pharmacol. 5:543-549; Hamann P. (2005) Expert Opin. Ther. Patents 15(9):1087-1103; Payne, G. (2003) Cancer Cell 3:207-212; Trail et al (2003) Cancer Immunol. Immunother. 52:328-337; Syrigos and Epenetos (1999) Anticancer Research 19:605-614). Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (McDonagh (2006) Protein Eng. Design & Sel.; Doronina et al (2006) Bioconj. Chem. 17:114-124; Erickson et al (2006) Cancer Res. 66(8):1-8; Sanderson et al (2005) Clin. Cancer Res. 11:843-852; Jeffrey et al (2005) J. Med. Chem. 48:1344-1358; Hamblett et al (2004) Clin. Cancer Res. 10:7063-7070). Drug moieties may impart their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

The anthracycline analog, doxorubicin (ADRIAMYCIN®) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al (2007) Cardiovasc. Toxicol. 7:75-

79). Immunoconjugates and prodrugs of daunorubicin and doxorubicin have been prepared and studied (Kratz et al (2006) Current Med. Chem. 13:477-523; Jeffrey et al (2006) Bioorganic & Med. Chem. Letters 16:358-362; Torgov et al (2005) Bioconj. Chem. 16:717-721; Nagy et al (2000) Proc. Natl. Acad. Sci. 97:829-834; Dubowchik et al (2002) Bioorg. & Med. Chem. Letters 12:1529-1532; King et al (2002) J. Med. Chem. 45:4336-4343; U.S. Pat. No. 6,630, 579). The antibody-drug conjugate BR96-doxorubicin reacts specifically with the tumor-associated antigen Lewis-Y and has been evaluated in phase I and II studies (Saleh et al (2000) J. Clin. Oncology 18:2282-2292; Ajani et al (2000) Cancer Jour. 6:78-81; Tolcher et al (1999) J. Clin. Oncology 17:478-484).

Morpholino analogs of doxorubicin and daunorubicin, formed by cyclization on the glycoside amino group, have greater potency (Acton et al (1984) J. Med. Chem. 638-645; U.S. Pat. No. 4,464,529; U.S. Pat. No. 4,672,057; U.S. Pat. No. 5,304,687). Nemorubicin is a semisynthetic analog of doxorubicin with a 2-methoxymorpholino group on the glycoside amino of doxorubicin and has been under clinical evaluation (Grandi et al (1990) Cancer Treat. Rew. 17:133; Ripamonti et al (1992) Brit. J. Cancer 65:703), including phase II/III trials for hepatocellular carcinoma (Sun et al (2003) Proceedings of the American Society for Clinical Oncology 22, Abs1448; Quintieri (2003) Proceedings of the American Association of Cancer Research, 44:1st Ed, Abs 4649; Pacciarini et al (2006) Jour. Clin. Oncology 24:14116)

Nemorubicin is named as (8S,10S)-6,8,11-trihydroxy-10-((2R,4S,5S,6S)-5-hydroxy-4-((S)-2-methoxymorpholino)-6-methyltetrahydro-2H-pyran-2-yloxy)-8-(2-hydroxy-acetyl)-1-methoxy-7,8,9,10-tetrahydrotetracene-5,12-dione, with CAS Reg. No. 108852-90-0, and has the structure:

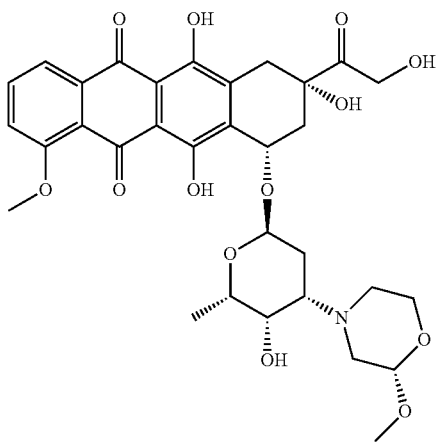 [SMILES: COc1cccc2c1C(=O)c1c(O)c3c(c(O)c1C2=O)C[C@@](O)(C(=O)CO)C[C@@H]3O[C@H]1C[C@H](N2CCO[C@H](OC)C2)[C@H](O)[C@H](C)O1]

Several metabolites of nemorubicin (MMDX) from liver microsomes have been characterized, including PNU-159682, (Quintieri et al (2005) Clinical Cancer Research, 11(4):1608-1617; Beulz-Riche et al (2001) Fundamental & Clinical Pharmacology, 15(6):373-378; EP 0889898; WO 2004/082689; WO 2004/082579). PNU-159682 was remarkably more cytotoxic than nemorubicin and doxorubicin in vitro, and was effective in vivo tumor models. PNU-159682 (formula (IIA) is named as 3'-deamino-3",4'-anhydro-[2"(S)-methoxy-3"(R)-oxy-4"-morpholinyl]doxorubicin, and has the structure:

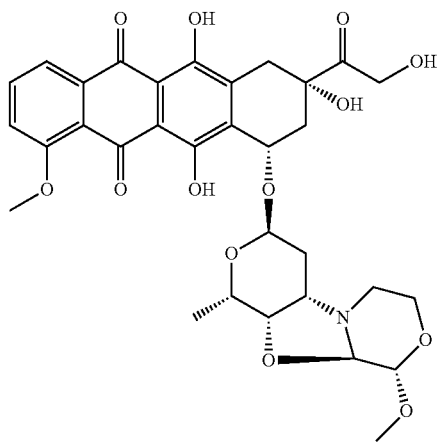

Certain PNU-159682 antibody-drug conjugates have been described ("NEMORUBICIN METABOLITE AND ANALOG ANTIBODY-DRUG CONJUGATES AND METHODS", PCT/US2009/031199, filed 16 Jan. 2009).

SUMMARY OF THE INVENTION

An aspect of the present invention is to provide new anthracycline derivative conjugates with carriers such as monoclonal or polyclonal antibodies reactive with a selected cell population, proteins, peptides or other carriers of synthetic origin reactive with receptor tissues.

Another aspect is a process for the preparation of such conjugates as well as useful intermediates.

The conjugates of the present invention are characterized by the formula (I)

[Ant-L-Z-]$_m$-T    (I)

wherein
Ant is anthracycline derivative residue,
L is a linker,
Z is a spacer,
m is an integer of from 1 to 30 and
T is carrier such as a protein, peptide, monoclonal or polyclonal antibody or a chemically modified derivative thereof suitable to be attached to the [Ant-L-Z-] moiety or moieties, or a polymeric carrier;
characterized in that the anthracycline derivative residue that Ant represents can be released to give an anthracycline derivative of formula (II):

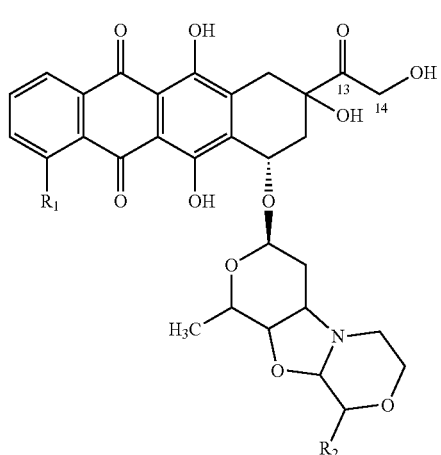

wherein $R_1$ is hydrogen atom, hydroxy or methoxy group and $R_2$ is a $C_1$-$C_5$ alkoxy group, or a pharmaceutically acceptable salt thereof.

The anthracycline derivative residue is tethered to the carrier through a linker spacer [L-Z-], and the bond between the anthracycline derivative and the linker arm can be cleaved under physiological conditions so that to release an anthracycline derivative of formula (II) as defined above, that is the bioactive agent.

For example, conjugates wherein the bond between the anthracycline derivative and the linker is sensitive to acid conditions or to reducing conditions can release the anthracycline derivative in the conditions typically encountered within the cell, e.g., in lysosomal vesicles.

A preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The anthracycline derivative conjugates of the formula (I) can be prepared through a process consisting of standard synthetic transformations; such process and the intermediates used in such process are also provided by the present invention.

The present invention also provides a pharmaceutical composition comprising an anthracycline derivative conjugate of the formula (I) or a pharmaceutically acceptable salt thereof and a pharmaceutically acceptable excipient or diluent.

An aspect of the invention is an anthracycline derivative of formula (IIc)

Ant-L-(Z)$_m$—X  (IIc)

wherein Ant is an anthracycline derivative selected from the structures:

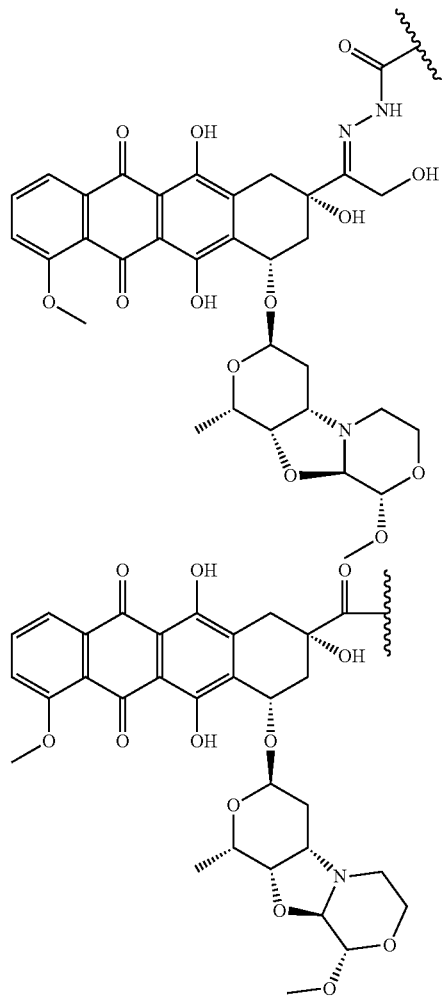

where the wavy line indicates the attachment to linker L; Z is an optional spacer; m is 0 or 1; X is a reactive functional group; and n is an integer from 1 to 6.

An aspect of the invention is an antibody-drug conjugate (ADC) compound comprising an antibody covalently attached by a linker L and an optional spacer Z to one or more anthracycline derivative drug moieties D, the compound having formula (Ic)

Ab-(L-Z$_m$-D)$_p$  (Ic)

or a pharmaceutically acceptable salt thereof, wherein p is an integer from 1 to 8.

BRIEF DESCRIPTION OF THE DRAWINGS

FIG. 1 shows in a graph form the stability of the compound 2 shown in Table 1 at pH 5.2 wherein in (Y) axis there is the percentage amount of the compound of the formula (IIA) as defined below, and in (X) axis the time in hours. This graph demonstrates the acid-sensitivity of the acetalic bound of the invention as indicated by the increased release of the free compound of the formula (IIA) from the conjugate under acid pH.

FIG. 2 shows an exemplary process to prepare Formula Ia compounds by reacting anthracycline derivative Formula II with vinyl ether compounds (X) or (IX) to give acetal compound (XI), hydrolysis to a carboxy compound (XII), and activation to form an N-hydroxy succinimide (NHS) ester (XIII), ready for conjugation with a carrier compound.

FIG. 3a shows an exemplary process to prepare Formula Ia compounds by reaction of activated N-hydroxy succinimide (NHS) ester (XIII) with amino-thiol reagent (XXI) to give XXII which can be reacted with pyridyl-disulfide carrier (T) intermediate (VI) to give disulfide linked anthracycline derivative conjugate (Ia), or reacted with maleimide carrier (T) intermediate (XXII) to give maleimide linked anthracycline derivative conjugate (Ia).

FIG. 4 shows an exemplary process to react an anthracycline derivative (II) with an acyl hydrazide derivative (XXV) to form hydrazone (XXVI) followed by conjugation with a carrier T reagent to give anthracycline derivative conjugate (Ib).

FIG. 5b shows an exemplary process: (2c) reacting an anthracycline derivative hydrazone (XXVI) with reagent (XXIX), followed by deprotection and coupling with amino-carrier T compound to give anthracycline derivative conjugate (Ib)

FIG. 6 shows an exemplary process to react an anthracycline derivative (II) with a acyl hydrazide, pyridyl disulfide (XXVIII) to form pyridyl disulfide hydrazone (XXXIV) followed by conjugation with a carrier T reagent to give anthracycline derivative conjugate (Ib).

FIG. 7a shows exemplary processeses: (3a) reacting an anthracycline derivative (XXXIV) with a thiol-carrier (XIV) to give anthracycline derivative conjugate (Ib); (3b) reacting an anthracycline derivative (XXXIV) with a thiol compound (XXXV) to give amine disulfide compound (XXXVI) which is coupled with a carboxyl-carrier T reagent to give anthracycline derivative conjugate (Ib); and (3d) condensation of deprotected (XXXVI) with aldehyde-carrier T compound (XX) to give anthracycline derivative conjugate (Ib).

FIG. 7b shows an exemplary process (3c) reacting an anthracycline derivative (XXXIV) with thiol ester (XXXVII), followed deprotection to carboxyl disulfide compound (XXXVIII), and coupling with amino-carrier T (XIV) to give anthracycline derivative conjugate (Ib).

FIG. 7c shows exemplary processes: (3e) reacting an anthracycline derivative (XXXIV) thiol reagent (XXXIX) to give disulfide thiol (XL), (3e') coupling disulfide thiol (XL) with pyridyl disulfide carrier compound (VI) to give anthracycline derivative conjugate (Ib); and coupling disulfide thiol (XL) with maleimide carrier compound (V) to give anthracycline derivative conjugate (Ib).

FIG. 8 shows a plot of SK-BR-3 in vitro cell viability at 3 days versus nM concentrations of: free drug PNU-159682 continuous exposure, PNU-159682 1 hr incubation, NHS-ketal-Ant 50, maleimide-ketal-Ant 51, maleimide-hydrazone-Ant 52, and thiopyridine-hydrazone-Ant 53.

FIG. 9 shows a plot of BT-474 in vitro cell viability at 3 days versus nM concentrations of: free drug PNU-159682 continuous exposure, PNU-159682 1 hr incubation, NHS-ketal-Ant 50, maleimide-ketal-Ant 51, maleimide-hydrazone-Ant 52, and thiopyridine-hydrazone-Ant 53.

FIG. 10 shows a plot of BT-474 in vitro cell viability at 3 days versus nM concentrations of: free drug PNU-159682 continuous exposure, PNU-159682 1 hr incubation, NHS-ketal-Ant 50, maleimide-ketal-Ant 51, maleimide-hydrazone-Ant 52, and thiopyridine-hydrazone-Ant 53.

FIG. 11 shows a plot of doxorubicin-resistant (DoxRes) Her2 in vitro cell viability at 3 days versus nM concentrations of: free drug PNU-159682 continuous exposure, PNU-159682 1 hr incubation, NHS-ketal-Ant 50, maleimide-ketal-Ant 51, maleimide-hydrazone-Ant 52, and thiopyridine-hydrazone-Ant 53. The DoxRes Her2 cell line is also known as "AdrRes Her2".

FIG. 12 shows a plot of SK-BR-3 in vitro cell viability at 3 days versus concentrations of: trastuzumab, trastuzumab-MCC-DM1 101, thio-trastuzumab (HC A114C)-maleimide ketal-Ant 102, thio-trastuzumab (HC A114C)-maleimide hydrazone-Ant 103. (Heavy chain antibody number by Kabat numbering scheme)

FIG. 13 shows a plot of BT-474 in vitro cell viability at 3 days versus concentrations of: trastuzumab, trastuzumab-MCC-DM1 101, thio-trastuzumab (HC A114C)-maleimide ketal-Ant 102, thio-trastuzumab (HC A114C)-maleimide hydrazone-Ant 103.

FIG. 14 shows a plot of MCF-7 in vitro cell viability at 3 days versus concentrations of: trastuzumab, trastuzumab-MCC-DM1 101, thio-trastuzumab (HC A114C)-maleimide ketal-Ant 102, thio-trastuzumab (HC A114C)-maleimide hydrazone-Ant 103.

FIG. 15 shows a plot of doxorubicin-resistant (DoxRes) Her2 in vitro cell viability at 3 days versus concentrations of: trastuzumab, trastuzumab-MCC-DM1 101, thio-trastuzumab (HC A114C)-maleimide ketal-Ant 102, thio-trastuzumab (HC A114C)-maleimide hydrazone-Ant 103.

FIG. 16 shows a plot of SK-BR-3 in vitro cell viability at 3 days versus concentrations of: anti-CD22 NHS ketal-Ant 110, trastuzumab, trastuzumab-MCC-DM1 101, thio-trastuzumab (HC A114C)-NHS-ketal-Ant 105.

FIG. 17 shows a plot of BT-474 in vitro cell viability at 3 days versus concentrations of: anti-CD22 NHS ketal-Ant 110, trastuzumab, trastuzumab-MCC-DM1 101, thio-trastuzumab (HC A114C)-NHS-ketal-Ant 105.

FIG. 18 shows a plot of MCF-7 in vitro cell viability at 3 days versus concentrations of: anti-CD22 NHS ketal-Ant 110, trastuzumab, trastuzumab-MCC-DM1 101, thio-trastuzumab (HC A114C)-NHS-ketal-Ant 105.

FIG. 19 shows a plot of doxorubicin-resistant (DoxRes) Her2 in vitro cell viability at 3 days versus concentrations of: anti-CD22 NHS ketal-Ant 110, trastuzumab, trastuzumab-MCC-DM1 101, thio-trastuzumab (HC A114C)-NHS-ketal-Ant 105.

FIG. 20 shows a plot of SK-BR-3 in vitro cell viability at 3 days versus concentrations (μg/ml) of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, thio-trastuzumab (HC A114C)-MC-vc-PAB-MMAE 106.

FIG. 21 shows a plot of SK-BR-3 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, PNU-159682 free drug.

FIG. 22 shows a plot of BT-474 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)—NHS-ketal-Ant 105, trastuzumab-MCC-DM1 101, thio-trastuzumab (HC A114C)-MC-vc-PAB-MMAE 106.

FIG. 23 shows a plot of BT-474 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, PNU-159682 free drug.

FIG. 24 shows a plot of MCF-7 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, thio-trastuzumab (HC A114C)-MC-vc-PAB-MMAE 106.

FIG. 25 shows a plot of MCF-7 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, PNU-159682 free drug.

FIG. 26 shows a plot of doxorubicin-resistant (DoxRes) Her2 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, thio-trastuzumab (HC A114C)-MC-vc-PAB-MMAE 106.

FIG. 27 shows a plot of doxorubicin-resistant (DoxRes) Her2 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, PNU-159682 free drug.

FIG. 28 shows a plot of doxorubicin-resistant (DoxRes) Her2 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, thio-trastuzumab (HC A114C)-MC-vc-PAB-MMAE 106.

FIG. 29 shows a plot of doxorubicin-resistant (DoxRes) Her2 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, PNU-159682 free drug, all plus verapamil.

FIG. 30 shows a plot of the in vivo mean tumor volume change over time in Burkitt's lymphoma Bjab-luc xenograft tumors inoculated into CB17 SCID mice after single intravenous (iv) dosing on day 0 with: (1) Vehicle, (2) thio-anti-CD22 (HC A114C)-MC-vc-PAB-MMAE 111 1 mg/kg, (3) thio-trastuzumab (HC A114C)-maleimide ketal-Ant 102 1 mg/kg, (4) thio-trastuzumab (HC A114C)-maleimide ketal-Ant 102 5 mg/kg, (5) thio-anti-CD22 (HC A114C)-maleimide ketal-Ant 107 1 mg/kg, (6) thio-anti-CD22 (HC A114C)-maleimide ketal-Ant 107 5 mg/kg, (7) thio-trastuzumab (HC A114C)-maleimide hydrazone-Ant 103 1 mg/kg, (8) thio-anti-CD22 (HC A114C)-maleimide hydrazone-Ant 108 1 mg/kg, (9) PNU-159682 free drug 8.77 ug/kg (26 ug/m2 exposure), matched to the drug dose of 1 mg/kg antibody-drug conjugates.

FIG. 31 shows a plot of the in vivo mean tumor volume change over time in MMTV-HER2Fo5 mammary allograft tumors inoculated into CRL nu/nu mice after single iv dosing on day 0 with: (1) Vehicle, (2) trastuzumab-MCC-DM1 101 5/mg/kg, (3) trastuzumab-MCC-DM1 101 10 mg/kg, (4) thio-trastuzumab (HC A114C)-maleimide ketal-Ant 102 5 mg/kg, (5) thio-trastuzumab (HC A114C)-maleimide ketal-Ant 102 10 mg/kg, (6) thio-anti-CD22 (HC A114C)-maleimide ketal-Ant 107 5 mg/kg, (7) thio-anti-CD22 (HC A114C)-maleimide ketal-Ant 107 10 mg/kg, (8) trastuzumab-MCC-DM1 101 5 mg/kg+thio-trastuzumab (HC A114C)-maleimide ketal-Ant 102 5 mg/kg.

DETAILED DESCRIPTION OF EXEMPLARY EMBODIMENTS

Figure 3B:
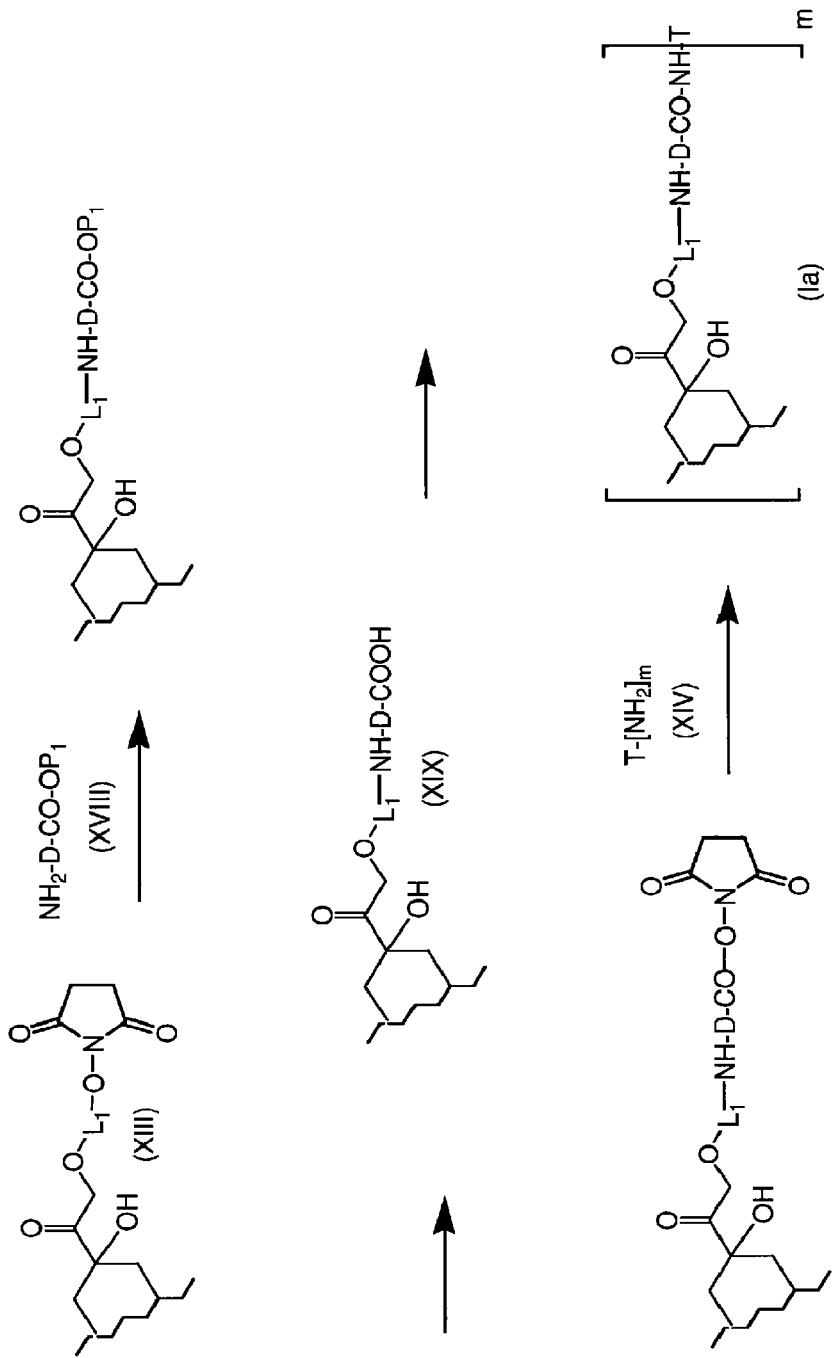
FIG. 3b shows exemplary processes to prepare Formula Ia compounds by reaction of activated N-hydroxy succinimide (NHS) ester (XIII) with amino-ester reagent (XVIII), followed by ester hydrolysis to give carboxy anthracycline derivative (XIX), which can be activated as an NHS ester and coupled with amino carrier T intermediate, e.g. an antibody, to give amide linked anthracycline derivative conjugate (Ia).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. Unless defined otherwise, technical and scientific terms used herein have the same meaning as commonly understood by one of ordinary skill in the art to which this invention belongs, and are consistent with: Singleton et al., (1994) *Dictionary of Microbiology and Molecular Biology, 2nd Ed.*, J. Wiley & Sons, New York, N.Y.; and Janeway, C., Travers, P., Walport, M., Shlomchik (2001) *Immuno Biology*, 5th Ed., Garland Publishing, New York.

DEFINITIONS

Unless stated otherwise, the following terms and phrases as used herein are intended to have the following meanings.

When trade names are used herein, applicants intend to independently include the trade name product formulation, the generic drug, and the active pharmaceutical ingredient(s) of the trade name product.

"Anthracycline derivative" is a nemorubicin metabolite, or analog compound, including but not limited to PNU-159682.

"Anthracycline derivative conjugate" is a compound comprised of an anthracycline derivative covalently attached through a linker to a carrier moiety, including antibodies, proteins or peptides. Anthracycline derivative conjugate compounds include antibody-drug conjugate (ADC) compounds.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2$H, 3H, $^{14}$C, $^{15}$N), protected forms, and racemic mixtures thereof.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g., Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

An "ErbB receptor" is a receptor protein tyrosine kinase which belongs to the ErbB receptor family which are important mediators of cell growth, differentiation and survival. The ErbB receptor family includes four distinct members including epidermal growth factor receptor (EGFR, ErbB1, HER1), HER2 (ErbB2 or $p185^{neu}$), HER3 (ErbB3) and HER4 (ErbB4 or tyro2). The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. The ErbB receptor may be native sequence human ErbB receptor. Accordingly, a "member of the ErbB receptor family" is EGFR (ErbB1), ErbB2, ErbB3, ErbB4 or any other ErbB receptor currently known or to be identified in the future. Sequence identity screening has resulted in the identification of two other ErbB receptor family members; ErbB3 (U.S. Pat. No. 5,183,884; U.S. Pat. No. 5,480,968; Kraus et al (1989) PNAS (USA) 86:9193-9197) and ErbB4 (EP 599274; Plowman et al (1993) Proc. Natl. Acad. Sci. USA, 90:1746-1750; and Plowman et al (1993) Nature 366:473-475). Both of these receptors display increased expression on at least some breast cancer cell lines. Anti-ErbB2 antibodies have been characterized (U.S. Pat. No. 5,677,171; U.S. Pat. No. 5,821,337; U.S. Pat. No. 6,054,297; U.S. Pat. No. 6,165,464; U.S. Pat. No. 6,407,213; U.S. Pat. No. 6,719,971; U.S. Pat. No. 6,800,738; Fendly et al (1990) Cancer Research 50:1550-1558; Kotts et al. (1990) In Vitro 26(3):59A; Sarup et al. (1991) Growth Regulation 1:72-82; Shepard et al. J. (1991) Clin. Immunol. 11(3):117-127; Kumar et al. (1991) Mol. Cell. Biol. 11(2):979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269(20): 14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all, or substantially all, of the FRs are those of a human immunoglobulin sequence. The humanized antibody optionally also will comprise at least a portion of an immunoglobulin constant region (Fc), typically that of a human immunoglobulin (Jones et al (1986) Nature, 321:522-525; Riechmann et al (1988) Nature 332:323-329; and Presta, (1992) Curr. Op. Struct. Biol., 2:593-596). Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®, trastuzumab) as described in Table 3 of U.S. Pat. No. 5,821,337 expressly incorporated herein by reference; humanized 520C9 (WO 93/21319) and humanized 2C4 antibodies.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "disorder" is any condition that would benefit from treatment of the present invention. This includes chronic and acute disorders or diseases including those pathological conditions which predispose the mammal to the disorder in question. Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders; and inflammatory, angiogenic and immunologic disorders. An exemplary disorder to be treated in accordance with the present invention is a solid, malignant tumor.

The term "therapeutically effective amount" refers to an amount of a drug effective to treat a disease or disorder in a mammal. In the case of cancer, the therapeutically effective amount of the drug may: (i) reduce the number of cancer cells; (ii) reduce the tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; and/or (vi) relieve to some extent one or more of the symptoms associated with the cancer. To the extent the drug may prevent growth and/or kill existing cancer cells, it may be cytostatic and/or cytotoxic. In animal models, efficacy may be assessed by physical measurements of the tumor during the course following administration of the ADC, and by determining partial and complete remission of tumor. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer which "overexpresses" a receptor, e.g. an ErbB receptor, is one which has significantly higher levels of the receptor, such as ErbB2, at the cell surface thereof, compared to a noncancerous cell of the same tissue type. Such overexpression may be caused by gene amplification or by increased transcription or translation. Receptor overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 98/45479), southern blotting, or polymerase chain reaction (PCR) techniques, such as real time quantitative PCR (RT-PCR). Overexpression of the receptor ligand, may be determined diagnostically by evaluating levels of the ligand (or nucleic acid encoding it) in the patient, e.g., in a tumor biopsy or by various diagnostic assays such as the IHC, FISH, southern blotting, PCR or in vivo assays described above. One may also study receptor overexpression by measuring a shed antigen (e.g., ErbB extracellular domain) in a biological fluid such as serum (see, e.g., U.S. Pat. No. 4,933,294; WO 91/05264; U.S. Pat. No. 5,401,638; and Sias et al (1990) J. Immunol. Methods 132: 73-80). Aside from the above assays, various other in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

The term "cytotoxic agent" as used herein refers to a substance that inhibits or prevents the function of cells and/or causes destruction of cells. The term is intended to include radioactive isotopes (e.g., $^{211}At$, $^{131}I$, $^{125}I$, $^{9}Y$, $^{186}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1 I, calicheamicin omega1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

The term "package insert" is used to refer to instructions customarily included in commercial packages of therapeutic products, that contain information about the indications, usage, dosage, administration, contraindications and/or warnings concerning the use of such therapeutic products.

"Alkyl" is $C_1$-$C_8$ hydrocarbon containing normal, secondary, tertiary or cyclic carbon atoms. Examples of alkyl radicals include, but not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$).

The term "alkylene" as used herein refers to a saturated linear or branched-chain divalent hydrocarbon radical of one to twelve carbon atoms (C$_1$-C$_{12}$), wherein the alkylene radical may be optionally substituted independently with one or more substituents described below. In another embodiment, an alkylene radical is one to eight carbon atoms (C$_1$-C8), or one to six carbon atoms (C$_1$-C$_6$). Examples of alkylene groups include, but are not limited to, methylene (—CH$_2$—), ethylene (—CH$_2$CH$_2$—), propylene (—CH$_2$CH$_2$CH$_2$—), and the like.

The term "alkenyl" refers to linear or branched-chain monovalent hydrocarbon radical of two to eight carbon atoms (C$_2$-C$_8$) with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkenylene" refers to linear or branched-chain divalent hydrocarbon radical of two to eight carbon atoms (C$_2$-C$_8$) with at least one site of unsaturation, i.e., a carbon-carbon, sp$^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH═CH—), allyl (—CH$_2$CH═CH—), and the like.

The term "alkynyl" refers to a linear or branched monovalent hydrocarbon radical of two to eight carbon atoms (C$_2$-C$_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "alkynylene" refers to a linear or branched divalent hydrocarbon radical of two to eight carbon atoms (C$_2$-C$_8$) with at least one site of unsaturation, i.e., a carbon-carbon, sp triple bond, wherein the alkynyl radical may be optionally. Examples include, but are not limited to, ethynylene (—C≡C—), propynylene (propargylene, —CH$_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms (C$_3$-C$_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms (C$_6$-C$_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms (C$_6$-C$_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Linker" or "link" means a divalent chemical moiety comprising a covalent bond or a chain of atoms that covalently attaches an antibody to a drug moiety. In various embodiments of formula I, a linker is specified as L.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an ADC. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

Anthracycline Derivatives and Anthracycline Derivative Conjugates

As stated before, in a first aspect the present invention relates to conjugates of an anthracycline derivative of the formula (I):

[Ant-L-Z-]$_n$-T (I)

wherein Ant, L, Z, m and T are as above defined, or a pharmaceutically acceptable salt thereof.

In a second aspect, there are provided anthracycline derivatives of the formula (I')

Ant-L-Z-Q (I')

wherein Ant, L and Z are as above defined, and Q is a hydrogen atom, a $C_1$-$C_6$ alkyl, $C_3$-$C_6$ cycloalkyl, phenyl or benzyl group, or a pharmaceutically salt thereof.

Preferably, the anthracycline derivative residue that Ant represents can be released to give an anthracycline derivative of formula (IIA):

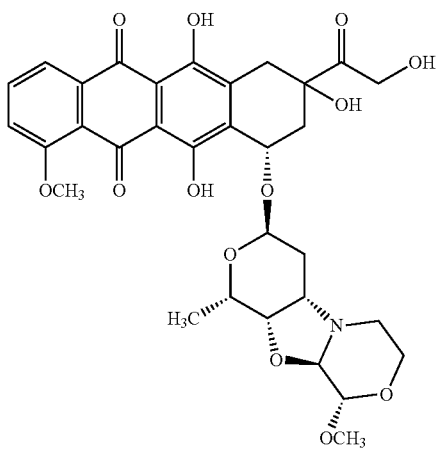

(IIA)

In another preferred aspect, the present invention provides an anthracycline derivative conjugate or a pharmaceutically salt thereof of the formula (Ia):

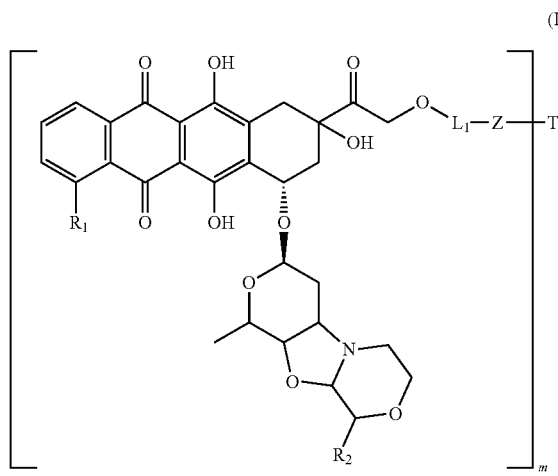

(Ia)

wherein:

$R_1$, $R_2$, Z, m and T are as defined above and $L_1$ is a linker of formula (III) or (IV):

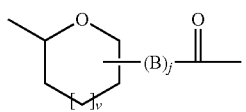

(III)

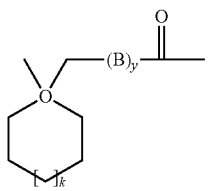

(IV)

wherein B is a $C_1$-$C_6$ alkylene moiety optionally hetero interrupted, and v, j, k and y are independently 0 or 1.

It is clear that in this instance, the anthracycline derivative residue which Ant represents is tether to the linker $L_1$ through an acetalic bond that involves the primary alcohol at the C-14 of the anthracycline skeleton.

As stated above, an anthracycline derivative conjugate or a pharmaceutically salt thereof of the formula (I) releases the desired free anthracycline derivative, as shown below for the preferred conjugates of the formula (Ia)

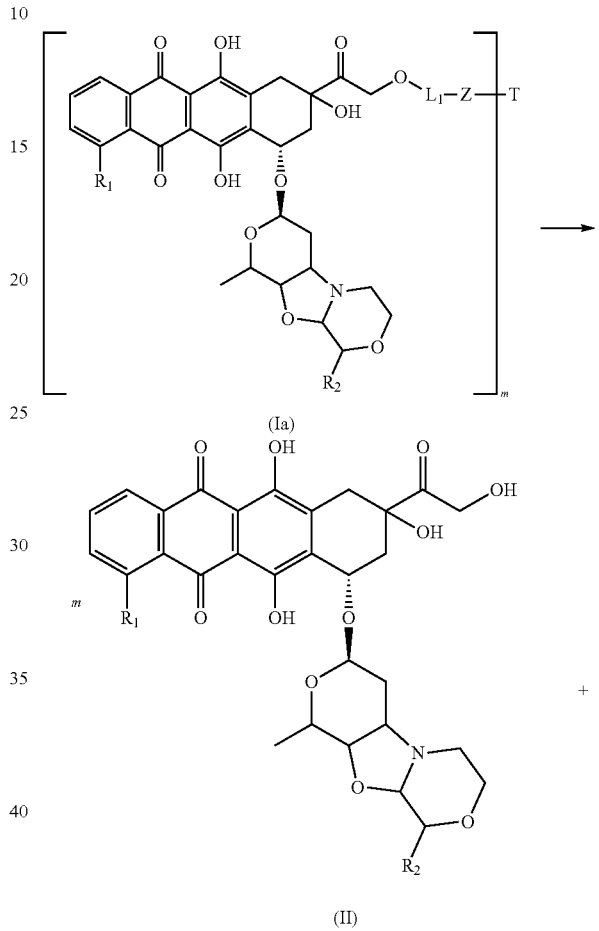

wherein $R_1$, $R_2$, $L_1$, Z, m and T are as above defined.

Preferably, Z is a spacer group like a) —NH—, b) —S—, c) aminoalkylene, thioalkylene, aminocycloalkylene or thiocycloalkylene bearing a further thiol or amino group or a carboxylic residue, d) a peptidic residue able to tether the $L_1$ linker to the T carrier by forming new bonds as e.g.; amide bonds, disulfide bonds.

T is preferably selected from a polyclonal antibody, or fragment thereof, comprising an antigen binding site, capable of binding to a tumor associated antigen; a monoclonal antibody, or fragment thereof comprising an antigen binding site, capable of binding to an antigen preferentially or selectively expressed on tumor cell populations; a peptide or protein capable optionally of preferentially or selectively binding to a tumor cell; or a chemically modified derivative thereof suitable to be attached to the [Ant-$L_1$-Z-] moiety or moieties, or a polymeric carrier.

Particularly preferred compounds of formula (Ia) are those wherein the spacer group which Z represents is:

i) —NH—, that is [—Z—]$_m$-T is derived from a carrier of the formula T-[NH$_2$]$_m$ wherein m is above defined;

ii) —S—, that is [—Z—]$_m$-T is derived from a carrier of the formula T-[SH]$_m$ wherein m is above defined;

iii) -NH-D-NH—CO— wherein -D- is a C$_1$-C$_6$ alkylene, C$_3$-C$_6$ cycloalkylene or -D-NH— is a peptide residue constituted from 1 to 4 amino acids having at least one free amino group, that is [—Z—]$_m$T is derived from a carrier of formula T-[COOH]$_m$ wherein m is above defined;

iv) —NH-D-CO—NH— wherein -D- is as defined above or -D-CO— is a peptide residue constituted from 1 to 4 amino acids having at least one free carboxylic group, that is [—Z—]$_m$-T is derived from a carrier of formula T-[NH$_2$]$_m$ wherein m is above defined;

v) —NH-D-N=CH— wherein -D- is as defined above and -D-N— is as defined above for -D-NH, that is [—Z—]$_m$-T is derived from a carrier of formula T-[CHO]$_m$ wherein m is above defined;

vi) —NH-D-S—CH— wherein -D- is as defined above or -D-S— is a peptide residue constituted from 1 to 4 amino acids having at least one free thiol group, that is [—Z—]$_m$-T is derived from a carrier derivative of formula (V);

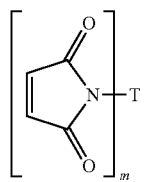

(V)

wherein m is above defined;

vii) -NH-D-S—S— wherein -D- and -D-S— are as defined above, that is [—Z—]$_m$-T is derived from a carrier derivative of formula (VI):

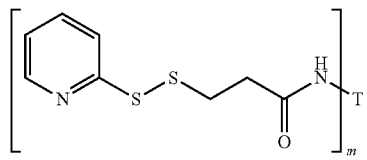

(VI)

wherein m is above defined.

In a further preferred aspect, the present invention provides an anthracycline derivative conjugate or a pharmaceutically salt thereof of the formula (Ib):

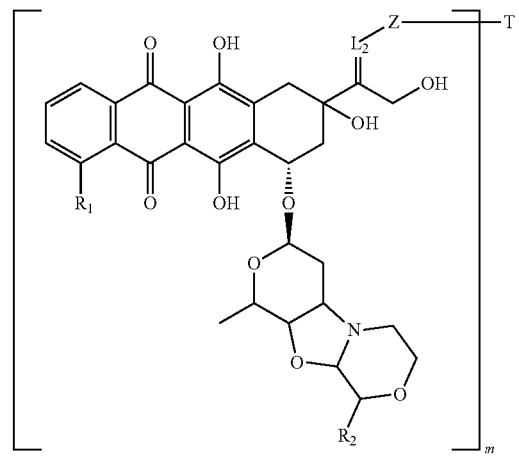

(Ib)

wherein R$_1$ and R$_2$, Z and T are as defined above and L$_2$ is a linker of formula (VII) or (VIII):

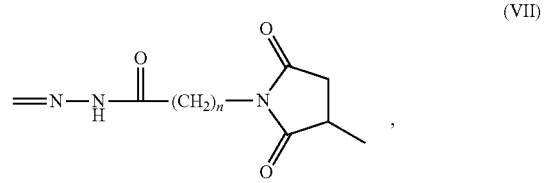

(VII)

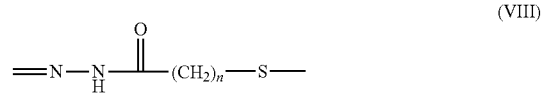

(VIII)

wherein n is an integer from 1 to 9.

In this case, the release of the desired free anthracycline derivative can be schematically illustrated as follows from the preferred conjugates of the formula (Ib):

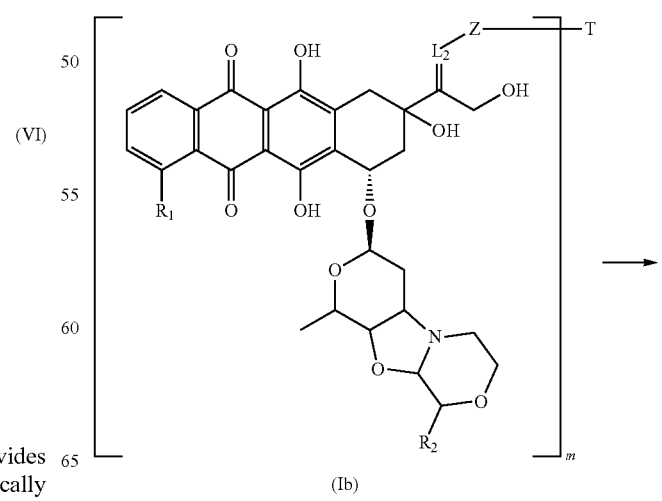

(Ib)

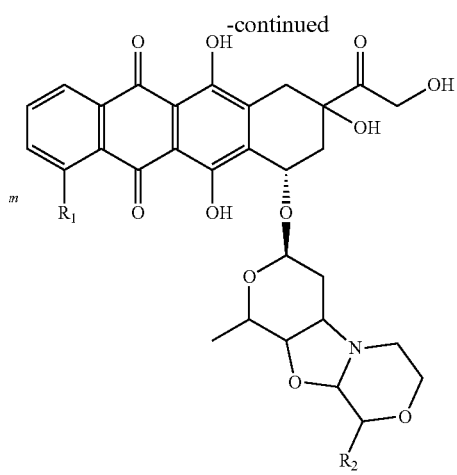

and

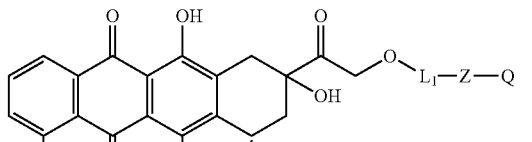

(I'a)

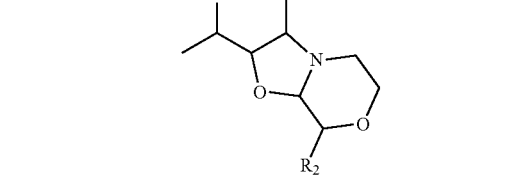

(I'b)

(II)

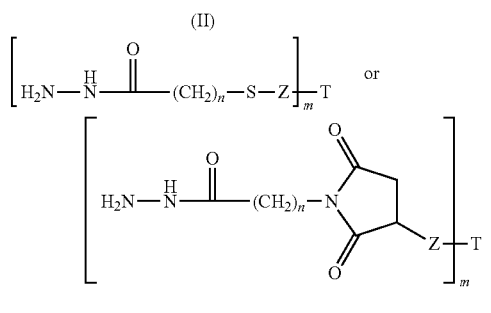

Particularly preferred compounds of the formula (Ib) are those wherein:

a) $L_2$ is a linker of formula (VII) as defined above and Z is a spacer group which is:
   viii) as defined above under point i);
   ix) as defined above under point ii);
   x) as defined above under point iii);
   xi) as defined above under point iv);
   xii) as defined above under point v);
   xiii) as defined above under point vi);
   xiv) as defined above under point vii);
   xv) —S-D-NH—CO— wherein -D-NH—CO— is as defined above under point iii);
   xvi) —S-D-CO—NH— wherein -D-CO—NH is as defined above under point iv);
   xvii) —S-D-N═C— wherein D and D-N— are as defined above under point v);
   xviii) S-D-S—CH— wherein D and -D-S— are as defined above under point vi);
   xix) —S-D-S—S— wherein D and -D-S— are as defined above under point vii).

Other particularly preferred compounds of the formula (Ib) are those wherein:

b) $L_2$ is a linker of formula (VIII) as above defined and Z is a spacer group which is:
   xx) as defined above under point ii)
   xxi) as defined above under point xv);
   xxii) as defined above under point xvi);
   xxiii) as defined above under point xvii);
   xxiv) as defined above under point xviii);
   xxv) as defined above under point xix).

Another particularly preferred object of the present invention are the compounds of the formula (I' a) and (I' b):

wherein $L_1$, $L_2$, $R_1$ and $R_2$ are as defined above, Z is —NH— or a peptidic residue constituted from 1 to 3 amino acids and Q is hydrogen atom, $C_1$-$C_6$ alkyl, $C_3$-$C_6$ cycloalkyl, phenyl or benzyl group.

Also in this case, the compounds of the formula (I' a) and (I' b) can be released in appropriate condition giving a compound of the formula (II) as defined above.

Another particularly preferred class of compounds are the compound of formula (I) or (I') wherein L is:
a residue of formula (IIIa) or (IVa),

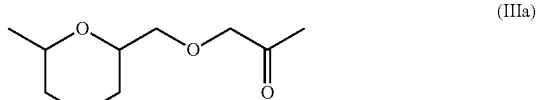

(IIIa)

(IVa)

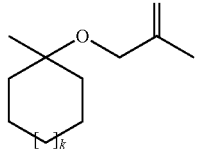

wherein v and k are as defined above;
or a residue of formula (VII) or (VIII) as defined above, characterized in that n is an integer from 2 to 5.

Linkers and Spacers

The linker L and spacer Z units attach the carrier, e.g. antibody, to the anthracycline derivative drug moiety D through covalent bond(s). The linker is a bifunctional or multifunctional moiety which can be used to link one or more drug moiety (D) and an antibody unit (Ab) to form antibody-drug conjugates (ADC) of formula Ic. The linker (L) may be stable outside a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety and to the antibody. A cysteine thiol, or an amine, e.g. N-terminus or amino acid side chain such as lysine, of the antibody (Ab) can form a bond with a functional group of a linker or spacer reagent, drug moiety (D) or drug-linker reagent (D-L).

Many positions on anthracycline derivative compounds may be useful as the linkage position, depending upon the type of linkage. For example, ester, amide, thioamide, thiocarbamate, or carbamate linkages may be formed from the hydroxyl group of the hydroxymethyl ketone at C14; ketal and hydrazone linkages may be formed from the C13 carbonyl group on the drug moiety; amide, carbamate, and urea linkages may be formed from an amino group on the drug moiety D; and various alkyl, ether, thioether, disulfide, and acyl linkages may be formed from the phenyl and aryl rings on the drug moiety by Friedel-Crafts type alkylation and acylation reactions.

The linkers and spacers are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targetted site; and (iv) maintain a cytotoxic, cell-killing effect or a cytostatic effect of the anthracycline derivative drug moiety. Stability of the ADC may be measured by standard analytical techniques such as mass spectroscopy, HPLC, and the separation/analysis technique LC/MS.

Covalent attachment of the antibody and the drug moiety requires the linker, and optional spacer, to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

In another embodiment, the linker or spacer may be substituted with groups which modulate solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). US 2007/0092940 teaches engineering antibodies by introduction of reactive cysteine amino acids.

In some embodiments, a Linker has a reactive nucleophilic group which is reactive with an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydroxyl, hydrazine, thiosemicarbazone, hydrazine carboxylate, and arylhydrazide. The electrophilic group on an antibody provides a convenient site for attachment to a Linker.

Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Spacers (Z) can be peptidic, comprising one or more amino acid units. Peptide linker reagents may be prepared by solid phase or liquid phase synthesis methods (E. Schroder and K. Lübke, *The Peptides*, volume 1, pp 76-136 (1965) Academic Press) that are well known in the field of peptide chemistry, including t-BOC chemistry (Geiser et al "Automation of solid-phase peptide synthesis" in *Macromolecular Sequencing and Synthesis*, Alan R. Liss, Inc., 1988, pp. 199-218) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

Exemplary amino acid linkers include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Amino acid side chains include those occurring naturally, as well as minor amino acids and non-naturally occurring amino acid analogs, such as citrulline. Amino acid side chains include hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3$-

NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl, as well as the following structures:

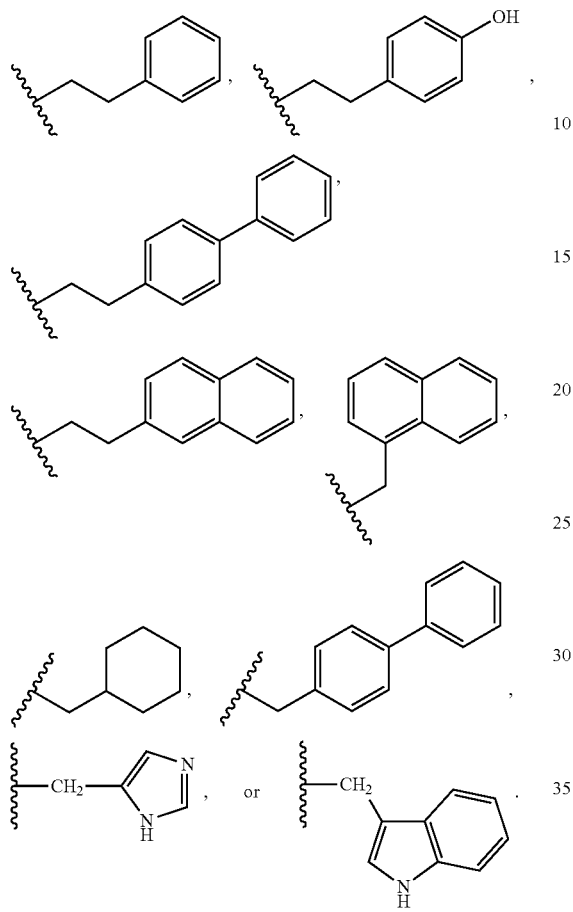

When the amino acid side chains include other than hydrogen (glycine), the carbon atom to which the amino acid side chain is attached is chiral. Each carbon atom to which the amino acid side chain is attached is independently in the (S) or (R) configuration, or a racemic mixture. Drug-linker reagents may thus be enantiomerically pure, racemic, or diastereomeric.

In exemplary embodiments, amino acid side chains are selected from those of natural and non-natural amino acids, including alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, norleucine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit).

Drug-Linker Intermediates

The invention includes drug-linker intermediates useful for conjugation to proteins, peptides, and antibodies. Such drug-linker intermediates include an anthracycline derivative of formula (IIc):

Ant-L-(Z)$_m$—X    (IIc)

wherein Ant is selected from the structures:

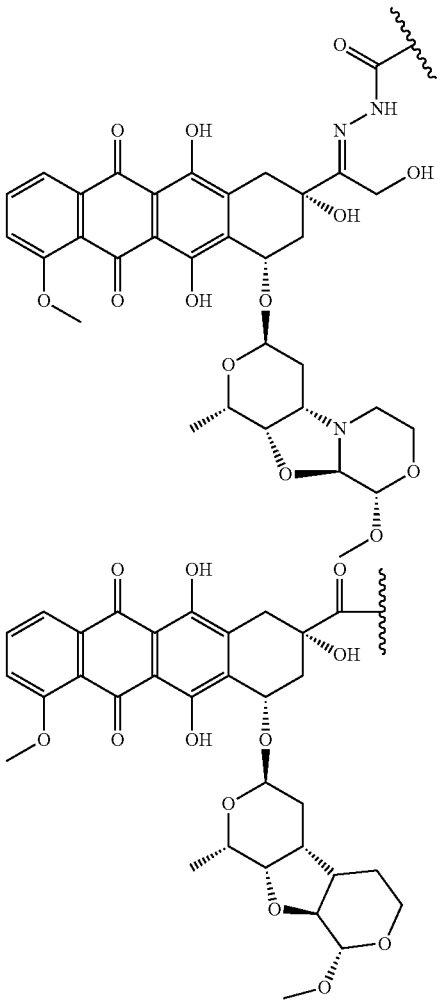

where the wavy line indicates the attachment to L;
L is a linker selected from —N(R)—, —N(R)$_m$(C$_1$-C$_{12}$ alkylene)-, —N(R)$_m$(C$_2$-C$_8$ alkenylene)-, —N(R)$_m$(C$_2$-C$_8$ alkynylene)-, —N(R)$_m$(CH$_2$CH$_2$O)$_n$—, and the structures:

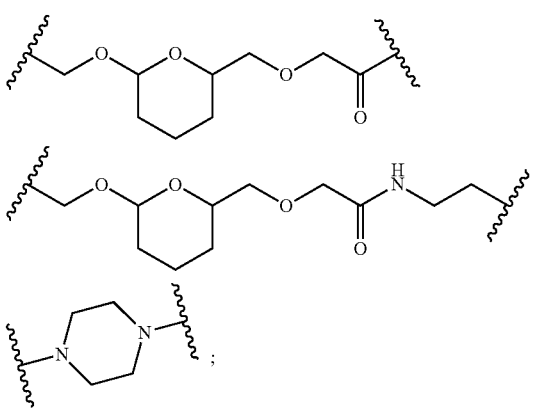

where the wavy lines indicate the attachments to Ant and Z; and
Z is an optional spacer selected from —CH$_2$C(O)—, —CH$_2$C(O)NR(C$_1$-C$_{12}$ alkylene)-, and the structures:

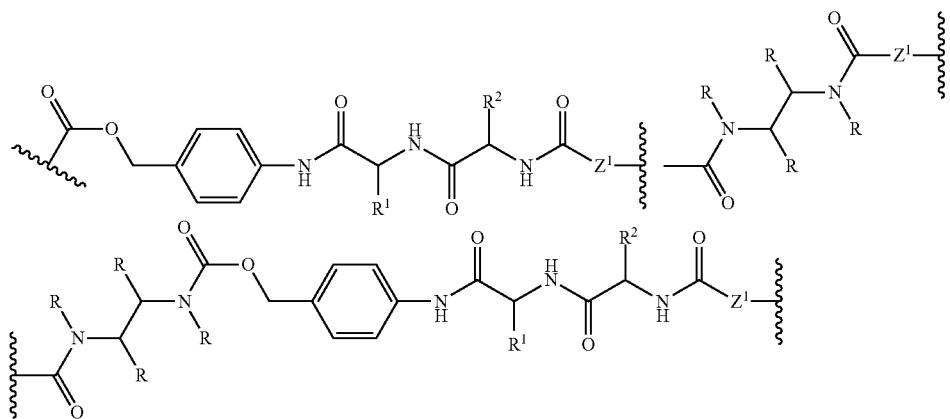

X is a reactive functional group selected from maleimide, thiol, amino, bromide, p-toluenesulfonate, iodide, hydroxyl, carboxyl, pyridyl disulfide, and N-hydroxysuccinimide;

R is H, $C_1$-$C_{12}$ alkyl, or $C_6$-$C_{20}$ aryl;

$R^1$ and $R^2$ are independently selected from an amino acid side chain;

$Z^1$ is selected from —($C_1$-$C_{12}$ alkylene)-, —($C_2$-$C_8$ alkenylene)-, —($C_2$-$C_8$ alkynylene)-, and —($CH_2CH_2O)_n$—, m is 0 or 1; and n is 1 to 6.

Anthracycline derivatives of formula IIc include the structures:

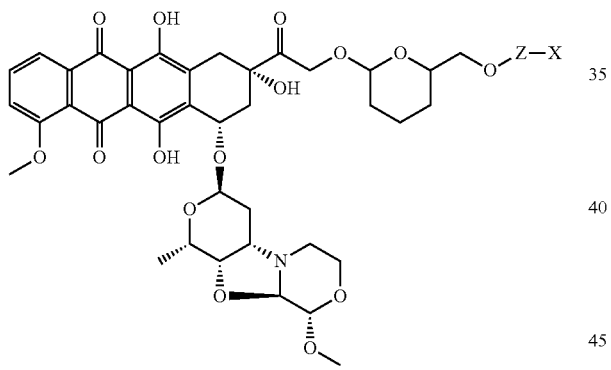

wherein Z—X is selected from:

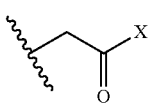

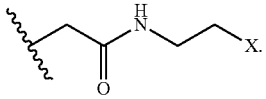

Exemplary drug-linker intermediate embodiments of formula IIc comprising an anthracycline drug moiety and a linker-spacer unit include compounds 50-53:

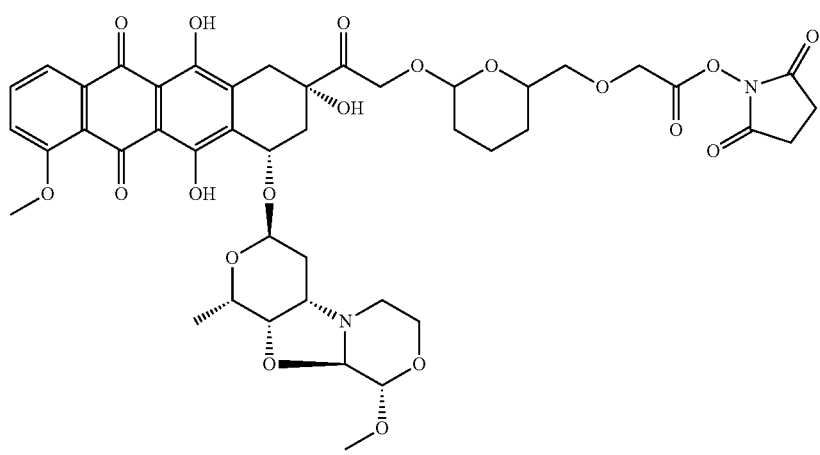

50

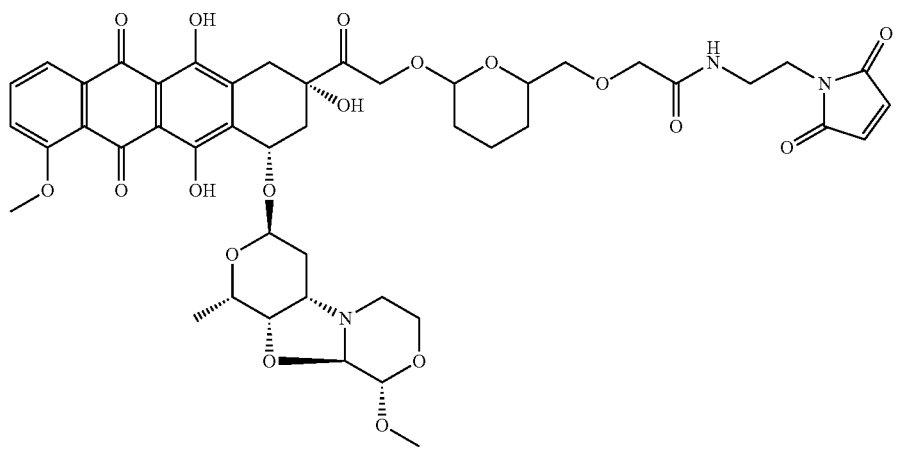
51
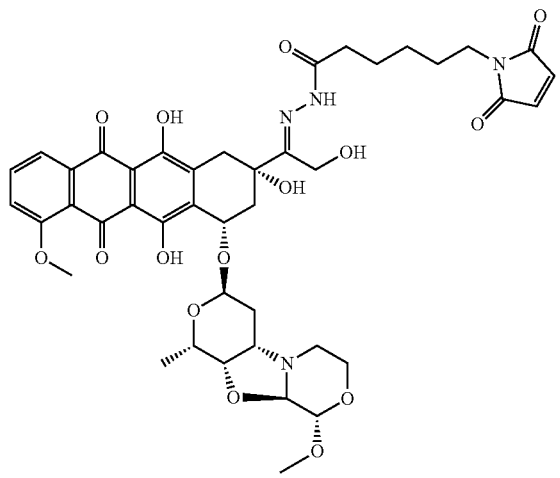
52
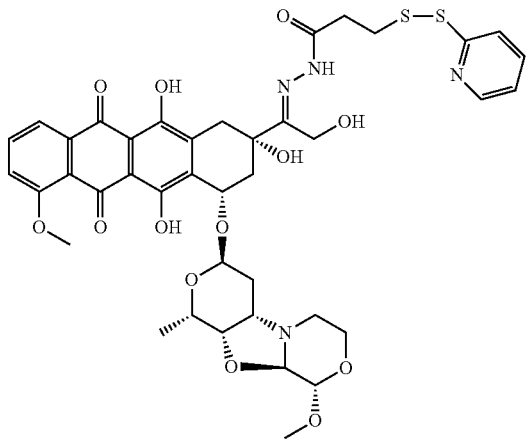
53
Anthracycline derivatives of formula IIc include the structure:
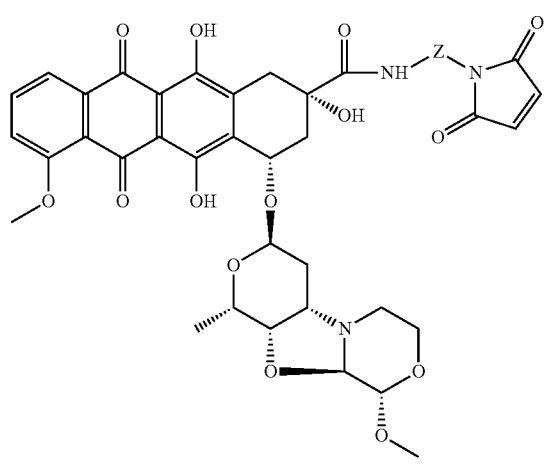
where Z is $C_1$-$C_{12}$ alkylene.
Exemplary drug-linker intermediate embodiments of formula IIc comprising an anthracycline drug moiety and a linker-spacer unit include compound 54 (Example 3a):
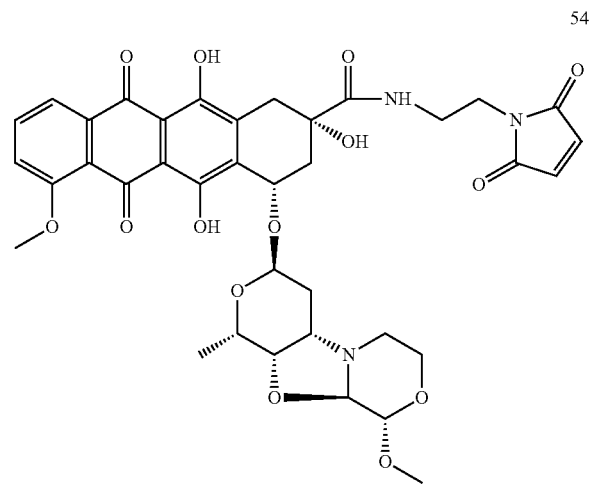 [SMILES: COc1cccc2c1C(=O)c1c(O)c3c(c(O)c1C2=O)C[C@@](O)(C(=O)NCCN1C(=O)C=CC1=O)C[C@@H]3O[C@H]1C[C@H]2[C@H](O[C@@H]3[C@@H](OC)OCCN32)[C@H](C)O1]
54

Anthracycline derivatives of formula IIc include the structures:

and where X is malemide:

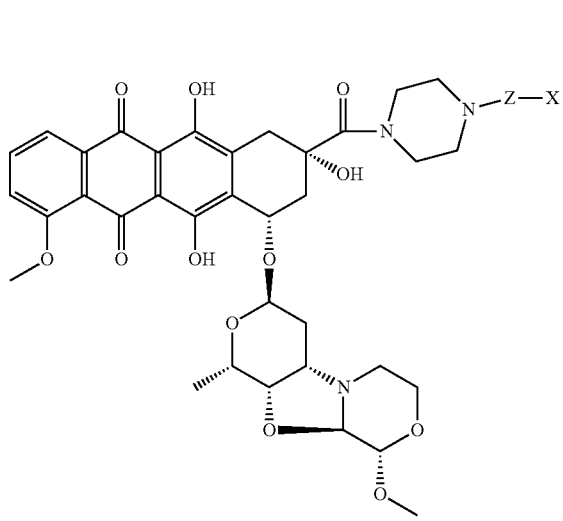

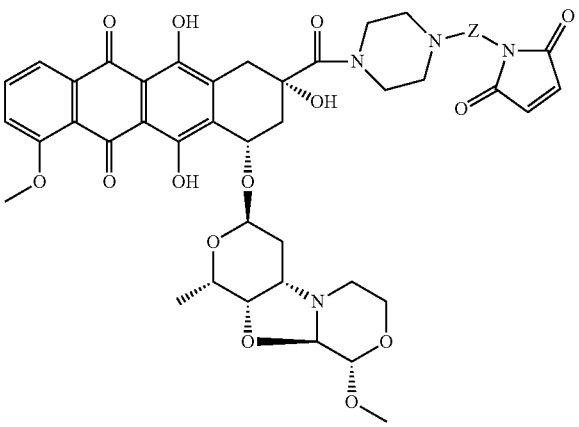

Figure 7D:
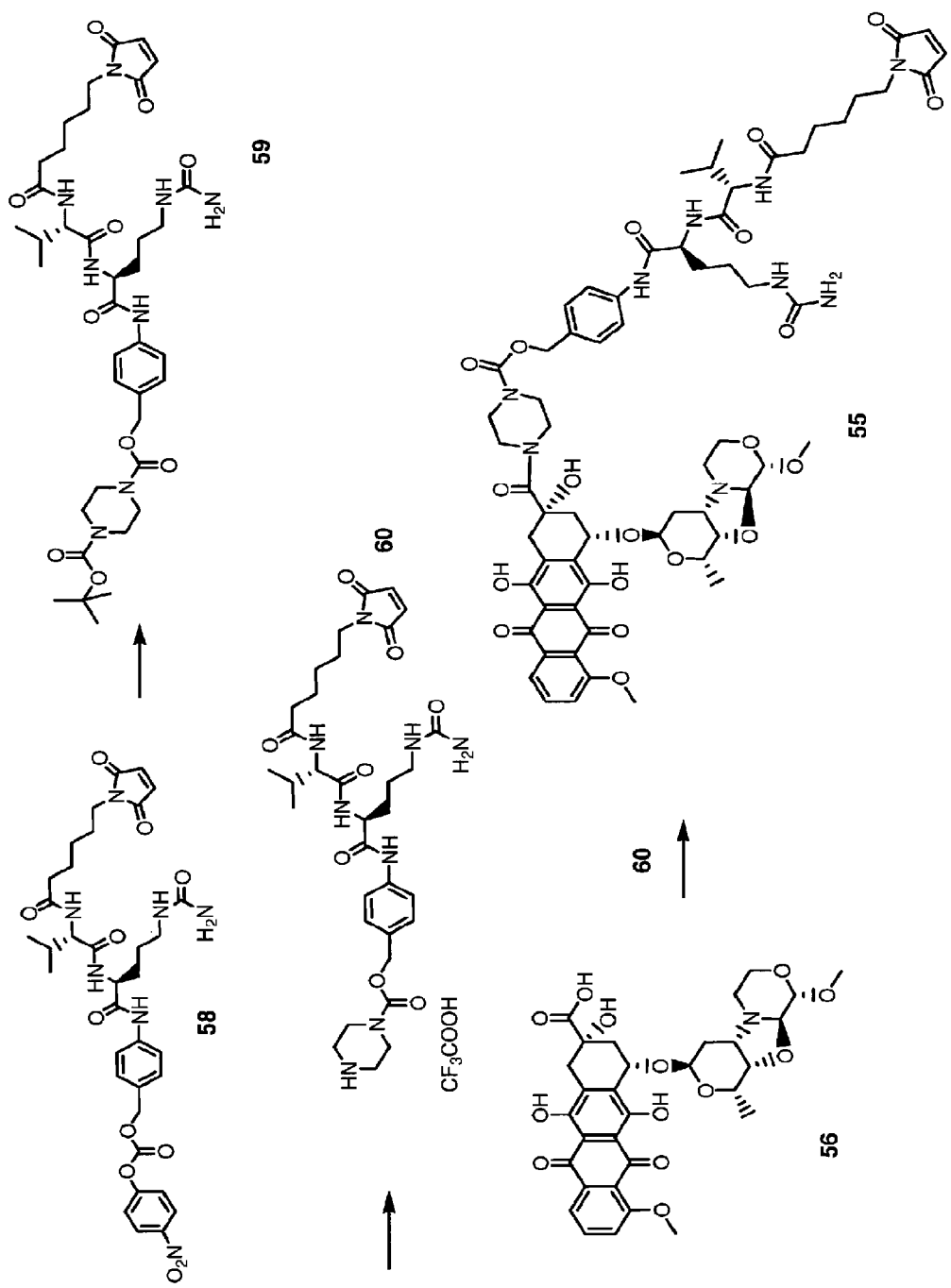
FIG. 7d shows a synthetic route to drug-linker intermediate N-[6-(2,5-dioxo-2,5-dihydro-1H-pyrrol-1-yl)hexanoyl]-L-valyl-$N^5$-carbamoyl-N-[4-({[(4-{[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]carbonyl}piperazin-1-yl)carbonyl]oxy}methyl)phenyl]-L-ornithinamide 55

Exemplary drug-linker intermediate embodiments of formula IIc comprising an anthracycline drug moiety and a linker-spacer unit include compound 55 (Example 3b). A synthetic route to drug-linker intermediate 55 from PNU-159682 C-14 carboxyl derivative 56 and linker-spacer intermediate 60 is shown in FIG. 7d.

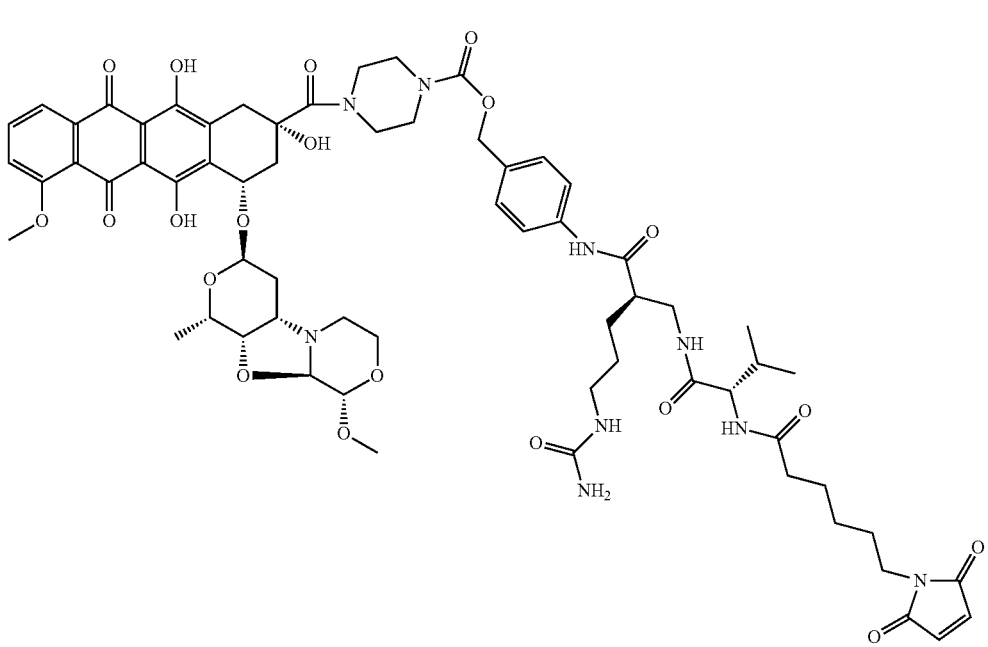

55

Anthracycline derivatives of formula IIc include the structures:

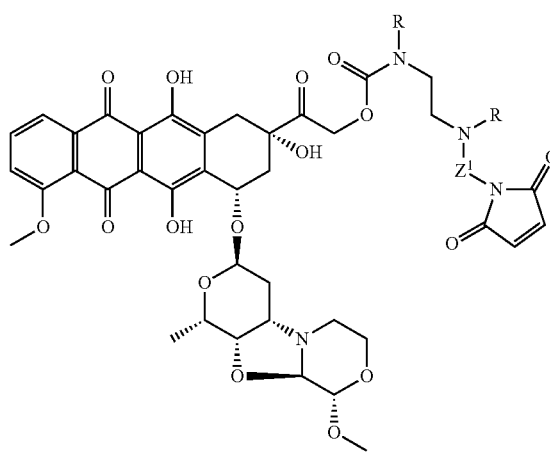

and where $Z^1$ is —($C_1$-$C_{12}$ alkylene)-.

Exemplary drug-linker intermediate embodiments of formula IIc comprising an anthracycline drug moiety and a linker-spacer unit include the compound:

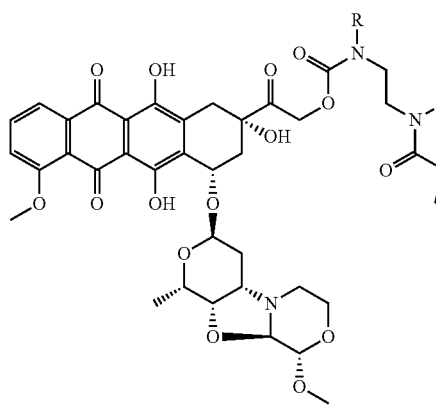

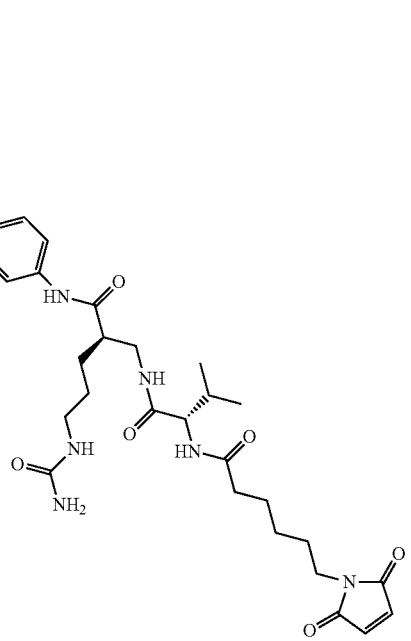

where Q is $C_1$-$C_8$ alkyl, —O—($C_1$-$C_8$ alkyl), -halogen, —$NO_2$ or —CN; and m is an integer ranging from 0-4.

An exemplary phe-lys(Mtr) dipeptide linker reagent having a maleimide stretcher unit and a p-aminobenzyl self-immolative Spacer unit can be prepared according to Dubowchik, et al. (1997) Tetrahedron Letters, 38:5257-60, and has the structure:

Linker and Spacer Reagents

Beta-glucuronide linkers between the antibody and the drug moiety by are substrates for cleavage by beta-glucuronidase (Jeffrey et al (2006) Bioconjugate Chem. 17:831-840; WO 2007/011968). The acetal linkage of beta-glucuronide releases a phenolic hydroxyl on the aryl ring, potentiating "self-immolation" and 1,6-elimination of the benzyloxycarbonyl group.

An exemplary valine-citrulline (val-cit or vc) dipeptide linker reagent having a maleimide stretcher and a para-aminobenzylcarbamoyl (PAB) self-immolative spacer has the structure:

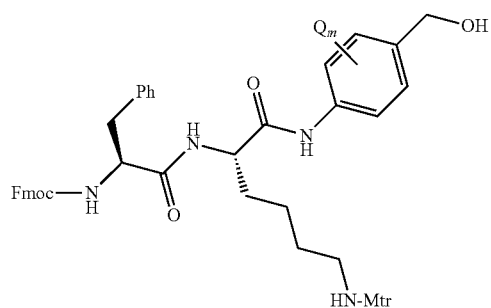

where Mtr is mono-4-methoxytrityl, Q is $C_1$-$C_8$ alkyl, —O—($C_1$-$C_8$ alkyl), -halogen, —$NO_2$ or —CN; and m is an integer ranging from 0-4.

The "self-immolative linker", PABC or PAB (para-aminobenzyloxycarbonyl), attaches the drug moiety to the antibody in the conjugate (Carl et al (1981) J. Med. Chem. 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. No. 6,218,519; U.S. Pat. No. 6,835,807; U.S. Pat. No. 6,268,488; US20040018194; WO98/13059; US20040052793; U.S. Pat. No. 6,677,435; U.S. Pat. No. 5,621,002; US20040121940; WO2004/032828). Other examples of self-immolative spacers besides PAB include, but are not limited to: (i) aromatic compounds that are electronically similar to the PAB group such as 2-aminoimidazol-5-methanol derivatives (Hay et al. (1999) Bioorg. Med. Chem. Lett. 9:2237), thiazoles US 2005/0256030), multiple, elongated PAB units (de Groot et al (2001) J. Org. Chem. 66:8815-8830; and ortho or para-aminobenzylacetals; and (ii) homologated styryl PAB analogs (U.S. Pat. No. 7,223,837). Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacers useful in ADC.

Linker reagents useful for the antibody drug conjugates of the invention include, but are not limited to: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, 1,8-bis-maleimidodiethyleneglycol (BM(PEO)$_2$), and 1,11-bis-maleimidotriethyleneglycol (BM(PEO)$_3$), which are commercially available from Pierce Biotechnology, Inc., ThermoScientific, Rockford, Ill., and other reagent suppliers. Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, anthracycline derivative drug moiety, or linker intermediate include iodoacetamide, bromoacetamide, vinyl pyridine, disulfide, pyridyl disulfide, isocyanate, and isothiocyanate.

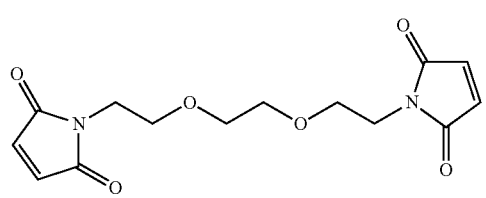

BM(PEO)$_2$

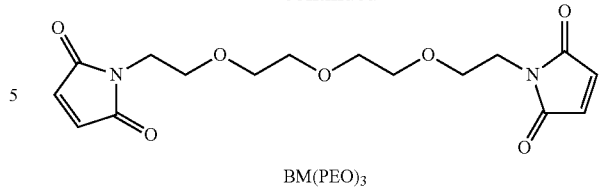

BM(PEO)$_3$

Other linker reagents are: N-succinimidyl-4-(2-pyridylthio)pentanoate (SPP), N-succinimidyl-3-(2-pyridyldithio) propionate (SPDP, Carlsson et al (1978) Biochem. J. 173:723-737), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345; WO 02/088172; US 2003130189; US2003096743; WO 03/026577; WO 03/043583; and WO 04/032828.

The Linker may be a dendritic type linker for covalent attachment of more than one drug moiety through a branching, multifunctional linker moiety to an antibody (US 2006/116422; US 2005/271615; de Groot et al (2003) Angew. Chem. Int. Ed. 42:4490-4494; Amir et al (2003) Angew. Chem. Int. Ed. 42:4494-4499; Shamis et al (2004) J. Am. Chem. Soc. 126:1726-1731; Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic or branched linker.

Carrier

The carrier moiety of anthracycline derivative conjugates is derived from polyclonal and monoclonal antibodies, proteins or peptides of natural or synthetic origin. Carrier compounds T-$NH_2$, T-COOH, T-CHO, T-SH, (V) or (VI) are suitable for conjugation with anthracycline derivative compounds. Carrier moieties may be derived from polyclonal antibodies raised against tumor associated antigens; or from monoclonal antibodies binding to antigens preferentially or selectively expressed on tumor cell populations; or from natural or recombinant peptides or proteins or growth factors preferentially or selectively binding to tumor cells; or from natural or synthetic polymeric carriers such as polylysine, polyglutamic acid, polyaspartic acid and their analogues and derivatives, or such as dextran or other polymeric carbohydrate analogues and their derivatives; or from synthetic copolymers such as those derived from N-(2-hydroxypropyl) methacrylamide (HPMA) see: J. Kopecek, Macromolecules. H. Benoit & P. Rempp, Ed.: 505-520 (1982) Pergamon Press. Oxford, England; or from poly(aminoacid) copolymers such as poly(GluNa, Ala, Tyr) which are useful as targetable drug-carriers for lung tissue R. Duncan et al., Journal of Bioactive and Compatible Polymers, Vol 4, July 1989. The carrier portion may be also derived from portions of the above mentioned peptides or proteins obtained through recombinant DNA techniques.

Antibodies

Representative examples of the above mentioned antibodies and of respective possible therapeutic applications are: anti-T-cell antibody T101 (Royston, I. et al., J. Immunol. 1980, 125:725); anti-CD5 antibody OKT1 (Ortho) ATCC CRL 8000 cronic lymphocytic leukemias); anti-CD20 antibody IgG1 ibritumomab, (Theuer, C. P. et al. Biotechnology Annual Review 2004 non-hodgkin's lymphoma); anti-CD33 antibody huCD33, (Drug of the future 2000 25(7):686 acute myeloid leukemia); anti-transferrin receptor antibody OKT9 (Ortho) ATCC CRL 8021 ovarian and other tumors; anti-melanoma antibody MAb 9.2.27 (Bumol, T. F. et al., Proc. Natl. Acad. Sci. USA 1982, 79:1245 melanomas); anti-carcinoma markers antibody such as: anti-CEA 1116 NS-3d ATCC CRL 8019), anti-alpha-fetoprotein OM 3-1.1 ATCC HB 134 also hepatomas), 791T/36 (Embleton, M. J. et al., Br. J. Cancer 1981, 43, 582 also osteogenic sarcoma), B 72.3 (U.S. Pat. No. 4,522,918 colorectal carcinomas and other tumors), anti-ovarian carcinoma antibody OVB 3 ATCC HB 9147, anti-breast carcinoma antibody HMGF antigen (Aboud-Pirak, E. et al., Cancer Res. 1988, 48:3188), anti-bladder carcinoma 1G3.10 (Yu, D. S. et al., Eur. J. Urol. 1987, 13:198), anti-CanAg antibody huC242 antibody (Olcher, Anthony W. et al., Journal of Clinical Oncology 2003, 21(2): 211-222 colon, pancreas, gastric), anti-prostate antibody MLN591 (Henry, Michael D. et al., Cancer Research 2004 advanced hormone-refractory prostate cancer).

Representative examples of the above mentioned growth factors and proteins of natural or recombinant origin are FGF, EGF, PDGF, TGF-ALPHA, ALPHA -MS, Interleukins, Interferons, TNF, melanotropin (MSH), Mcm2 etc. The carrier T-CHO is preferably derived from polyclonal or monoclonal antibodies having the carbohydrate moiety, preferentially located in the Fc region, selectively oxidized to aldehyde groups by means of chemical or enzymatic methods, as described in U.S. Pat. No. 4,671,958.

The antibody unit (Ab) of Formula IIc includes any unit, type, or class of antibody that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified. In one aspect, the antibody unit acts to deliver the anthracycline derivative drug moiety to the particular target cell population with which the antibody unit reacts. Such antibodies include, but are not limited to, large molecular weight proteins such as, full-length antibodies and antibody fragments. The antibodies of Formula I allow attaining high concentrations of active metabolite molecules in cancer cells. Intracellular targeting may be achieved by methods and compounds which allow accumulation or retention of biologically active agents inside cells. Such effective targeting may be applicable to a variety of therapeutic formulations and procedures.

In one embodiment, the ADC specifically binds to a receptor encoded by an ErbB gene, such as EGFR, HER2, HER3 and HER4. The ADC may specifically bind to the extracellular domain of the HER2 receptor. The ADC may inhibit growth of tumor cells which overexpress HER2 receptor.

In another embodiment, the antibody (Ab) of Formula IIc is a humanized antibody such as huMAb4D5-1, huMAb4D5-2, huMAb4D5-3, huMAb4D5-4, huMAb4D5-5, huMAb4D5-6, huMAb4D5-7 or huMAb4D5-8 (trastuzumab).

The antibodies of the invention include cysteine-engineered antibodies where one or more amino acids of any form of wild-type or parent antibody is replaced with a cysteine amino acid. The engineered cysteine amino acid is a free cysteine acid and not part of an intrachain or interchain disulfide unit. Any form, type, or variant of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. The cysteine engineered antibodies of the invention include monoclonal antibodies, humanized or chimeric monoclonal antibodies, antigen-binding fragments of antibodies, fusion polypeptides and analogs that preferentially bind cell-associated polypeptides.

Cysteine-engineered antibodies have been designed as Fab antibody fragments (thioFab) and expressed as full-length, IgG monoclonal (thioMab) antibodies (U.S. Pat. No. 7,521, 541, the contents of which are incorporated by reference). ThioFab and ThioMab antibodies have been conjugated through linkers at the newly introduced cysteine thiols with thiol-reactive linker reagents and drug-linker reagents to prepare antibody-drug conjugates (Thio ADC), including anti-HER2 (U.S. Pat. No. 7,521,541), anti-CD22 (US 2008/0050310), and anti-steap1 (WO 2008/052187), as well as other cysteine engineered antibodies and antibody-drug conjugates.

Antibodies comprising the antibody-drug conjugates of Formula IIc preferably retain the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antibody of the invention is capable of binding may be a member of a subset of one of the above-mentioned categories, wherein the other subset(s) of said category comprise other molecules/antigens that have a distinct characteristic (with respect to the antigen of interest).

In one embodiment, the antibody of antibody-drug conjugates (ADC) of Formula IIc specifically binds to a receptor encoded by an ErbB gene. The antibody may bind specifically to an ErbB receptor selected from EGFR, HER2, HER3 and HER4. The ADC may specifically bind to the extracellular domain (ECD) of the HER2 receptor and inhibit the growth of tumor cells which overexpress HER2 receptor. The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-

5, huMAb4D5-6, huMAb4D5-7 or huMAb4D5-8 (trastuzumab). The antibody may be an antibody fragment, e.g. a Fab fragment.

Antibodies in Formula IIc antibody-drug conjugates (ADC) and which may be useful in the treatment of cancer include, but are not limited to, antibodies against cell surface receptors and tumor-associated antigens (TAA). Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to the Tumor-Associated Antigens (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, Genbank accession no. NM_001203); ten Dijke, P., et al Science 264 (5155):101-104 (1994), Oncogene 14 (11): 1377-1382 (1997)); WO2004063362 (Claim 2); WO2003042661 (Claim 12); U52003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377(Page 349-350); WO200230268 (Claim 27; Page 376); WO200148204 (Example; FIG. 4); NP_001194 bone morphogenetic protein receptor, type IB/pid=NP_001194.1; Cross-references: MIM:603248; NP_001194.1; AY065994 (2) E16 (LAT1, SLC7A5, Genbank accession no. NM_003486); Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); US 20050107595; US 20050106644; NP_003477 solute carrier family 7 (cationic amino acid transporter, y+system), member 5/pid=NP_003477.3—*Homo sapiens*; Cross-references: MIM:600182; NP_003477.3; NM_015923; NM_003486_1

(3) STEAP1 (six transmembrane epithelial antigen of prostate, Genbank accession no. NM_012449); Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate; Cross-references: MIM:604415; NP_036581.1; NM_012449_1

(4) 0772P(CA125, MUC16, Genbank accession no. AF361486); J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); US2003091580 (Claim 6); WO200206317 (Claim 6; Page 400-408); Cross-references: GI:34501467; AAK74120.3; AF361486_1

(5) MPF (MPF, MSLN, SMR, megakaryocyte potentiating factor, mesothelin, Genbank accession no. NM_005823); Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424); J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP_006415.1; NM_006424_1

(7) Sema 5b (F1110372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878); Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC:10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5);

EP1347046 (Claim 1); WO2003025148 (Claim 20); Cross-references: GI:37182378; AAQ88991.1; AY358628_1

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004.

(10) MSG783 (RNF124, hypothetical protein F1120315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GI:22655488; AAN04080.1; AF455138_1

(12) TrpM4 (BR22450, F1120041, TRPM4, TRPM4B, transient receptor potential cation channel, subfamily M, member 4, Genbank accession no. NM_017636); Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212); Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO2002088170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004); Fujisaku et al (1989) J. Biol. Chem. 264 (4): 2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIG. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674); Proc. Natl. Acad. Sci. U.S.A. (2003) 100 (7): 4126-4131, Blood (2002) 100 (9):3068-3076, Muller et al (1992) Eur. J. Immunol. 22 (6):1621-1625); WO2004016225 (Claim 2, FIG. 140); WO2003087768, US2004101874 (Claim 1, page 102); WO2003062401 (Claim 9); WO200278524 (Example 2); US2002150573 (Claim 5, page 15); U.S. Pat. No. 5,644,033; WO2003048202 (Claim 1, pages 306 and 309); WO 99/558658, U.S. Pat. No. 6,534,482 (Claim 13, FIG. 17A/B); WO200055351 (Claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130); Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1

Figure 5A:
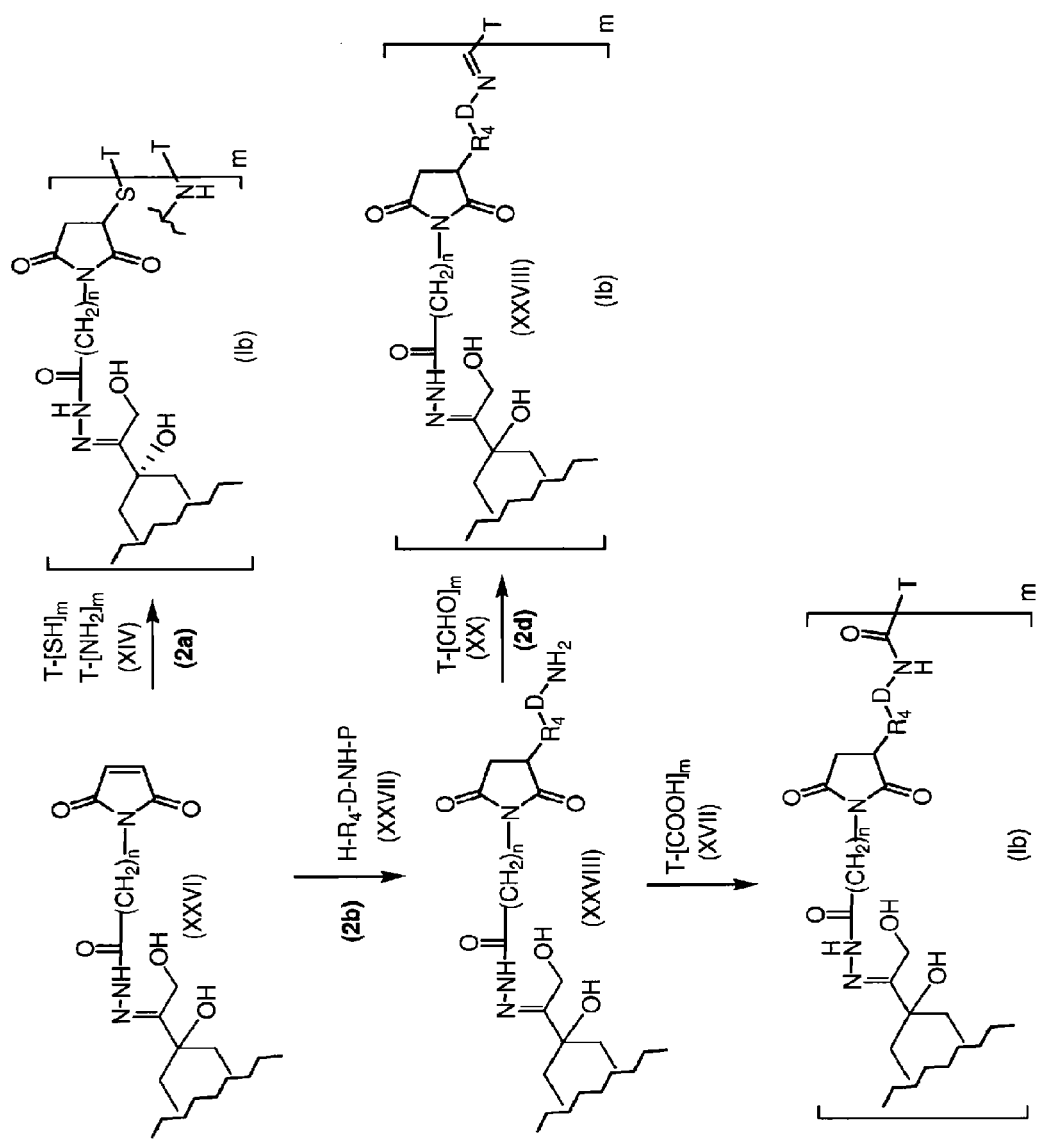
FIG. 5a shows exemplary processes: (2a) reacting an anthracycline derivative hydrazone (XXVI) with a thiol- or amino-carrier T compound (XIV) to give an anthracycline derivative conjugate (Ib); (2b) reacting an anthracycline derivative hydrazone (XXVI) with reagent (XXVII), followed by deprotection to (XXVIII) and coupling with carboxyl-carrier T compound (XVII) to give an anthracycline derivative conjugate (Ib); and (2d) condensation of deprotected (XXVIII) with aldehyde-carrier T compound (XX) to give anthracycline derivative conjugate (Ib).
Figure 5C:
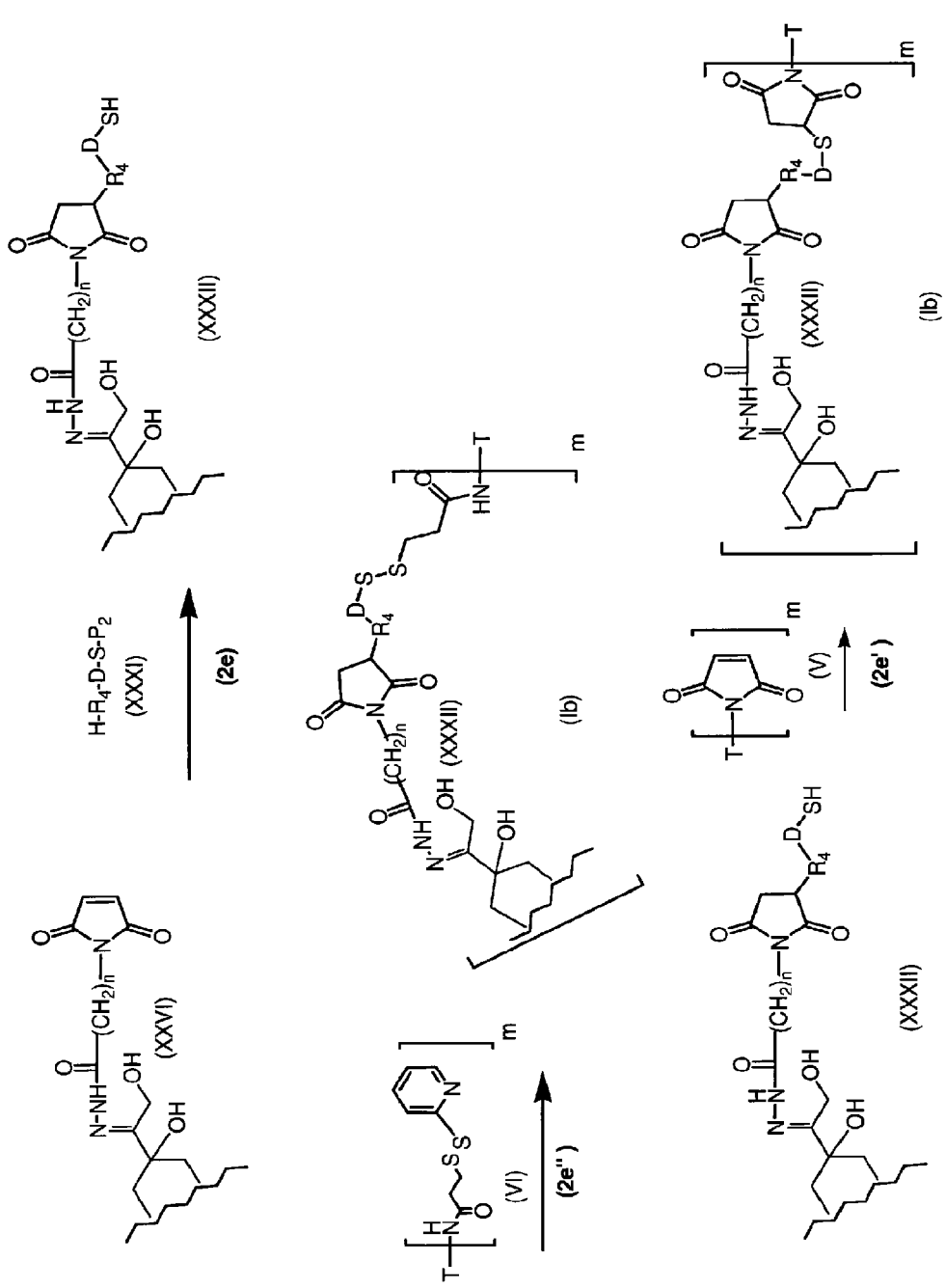
FIG. 5c shows exemplary processes: (2e) reacting an anthracycline derivative hydrazone (XXVI) with reagent (XXXI) to give (XOCH), followed by (2e") coupling with pyridyl disulfide carrier compound (VI) to give anthracycline derivative conjugate (Ib), and (2e') coupling (XXXII) with maleimide carrier compound (V) to give anthracycline derivative conjugate (Ib).

(17) HER2 (ErbB2, Genbank accession no. M11730); Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709;

WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728

(19) MDP (DPEP1, Genbank accession no. BC017023); Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: □9UHF4; Q6UWA9; Q96SH8; EMBL; AF184971; AAF01320.1.

(21) Brevican (BCAN, BEHAB, Genbank accession no. AF229053); Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, HekS, EPHT3, Tyro5, Genbank accession no. NM_004442); Chan, J. and Watt, V. M., Oncogene 6 (6), 1057-1061 (1991) Oncogene 10 (5):897-905 (1995), Annu Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

(23) ASLG659 (B7h, Genbank accession no. AX092328); US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436); Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: 043653; EMBL; AF043498; AAC39607.1.

(25) GEDA (Genbank accession No. AY260763); AAP14954 lipoma HMGIC fusion-partner-like protein/pid=AAP14954.1 *Homo sapiens* (human); WO2003054152 (Claim 20); WO2003000842 (Claim 1); WO2003023013 (Example 3, Claim 20); US2003194704 (Claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens*; Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM:606269; NP_443177.1; NM_052945_1; AF132600

(27) CD22 (B-cell receptor CD22-β isoform, BL-CAM, Lyb-8, Lyb8, SIGLEC-2, FLJ22814, Genbank accession No. AK026467); Wilson et al (1991) J. Exp. Med. 173:137-146; WO2003072036 (Claim 1; FIG. 1); Cross-references: MIM: 107266; NP_001762.1; NM_001771_1

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation); 226 aa), pI: 4.84, MW: 25028 TM: 2 [P] Gene Chromosome: 19q13.2, Genbank accession No. NP_001774.10); WO2003088808, US20030228319; WO2003062401 (Claim 9); US2002150573 (Claim 4, pages 13-14); WO9958658 (Claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa), pI: 8.54 MW: 41959 TM: 7 [P] Gene Chromosome: 11q23.3, Genbank accession No. NP_001707.1); WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (Claim 1, page 38); U.S. Pat. No. 5,440,021 (Example 2, col 49-52); WO9428931 (pages 56-58); WO9217497 (Claim 7, FIG. 5); Dobner et al (1992) Eur. J. Immunol. 22:2795-2799; Barella et al (1995) Biochem. J. 309:773-779

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession No. NP_002111.1); Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci. USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); US6011146 (col 145-146); Kasahara et al (1989) Immunogenetics 30(1):66-68; Larhammar et al (1985) J. Biol. Chem. 260(26):14111-14119

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2); Le et al (1997) FEBS Lett. 418(1-2):195-199; WO2004047749; WO2003072035 (Claim 10); Touchman et al (2000) Genome Res. 10:165-173; WO200222660 (Claim 20); WO2003093444 (Claim 1); WO2003087768 (Claim 1); WO2003029277 (page 82)

(32) CD72 (B-cell differentiation antigen CD72, Lyb-2); 359 aa), pI: 8.66, MW: 40225 TM: 1 [P] Gene Chromosome: 9p13.3, Genbank accession No. NP_001773.1); WO2004042346 (Claim 65); WO2003026493 (pages 51-52, 57-58); WO200075655 (pages 106); Von Hoegen et al (1990) J. Immunol. 144(12):4870-4877; Strausberg et al (2002) Proc. Natl. Acad. Sci. USA 99:16899-16903

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa), pI: 6.20, MW: 74147 TM: 1 [P] Gene Chromosome: 5q12, Genbank accession No. NP_005573.1); US2002193567; WO9707198 (Claim 11, pages 39-42); Miura et al (1996) Genomics 38(3):299-304; Miura et al (1998) Blood 92:2815-2822; WO2003083047; WO9744452 (Claim 8, pages 57-61); WO200012130 (pages 24-26)

(34) FcRH1 (Fc receptor-like protein 1, a putative receptor for the immunoglobulin Fc domain that contains C2 type Ig-like and ITAM domains, may have a role in B-lymphocyte differentiation); 429 aa), pI: 5.28, MW: 46925 TM: 1 [P] Gene Chromosome: 1q21-1q22, Genbank accession No. NP_443170.1); WO2003077836; WO200138490 (Claim 6, FIG. 18E-1-18-E-2); Davis et al (2001) Proc. Natl. Acad. Sci. USA 98(17):9772-9777; WO2003089624 (Claim 8); EP1347046 (Claim 1); WO2003089624 (Claim 7)

(35) IRTA2 (FcRH5, Immunoglobulin superfamily receptor translocation associated 2, a putative immunoreceptor with possible roles in B cell development and lymphomagenesis; deregulation of the gene by translocation occurs in some B cell malignancies); 977 aa), pI: 6.88 MW: 106468 TM: 1 [P] Gene Chromosome: 1q21, (Genbank accession No. Human:AF343662, AF343663, AF343664, AF343665, AF369794, AF397453, AK090423, AK090475, AL834187, AY358085; Mouse:AK089756, AY158090, AY506558; NP 112571.1); WO2003024392 (Claim 2, FIG. 97); Nakayama et al (2000) Biochem. Biophys. Res. Commun. 277(1):124-127; WO2003077836; WO200138490 (Claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; (Genbank accession No. AF179274; AY358907, CAF85723, CQ782436); WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; U.S. Pat. No. 6,410,506; US 66420061; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. Oct 15; 94(2):178-84.

Further preferred compounds are the compounds of formula (Ia), (Ib), (I' a) and (I' b) reported as Compounds 1-14 in the Table 1 below:

TABLE 1

[Ant-L—Z—]$_m$—T (I)

Ant-L—Z—Q (I')

| Comp | Formula | Ant | L | Z | M | Q | T |
|---|---|---|---|---|---|---|---|
| 1 | I' | IIa | (cyclohexyl-O-CH2-C(=O)- linker) | —NH— | — | H | — |
| 2 | I' | IIa | (cyclohexyl-O-CH2-C(=O)- linker) | —NH— | — | CH$_3$ | — |

TABLE 1-continued
[Ant-L—Z—]$_m$—T  (I)
Ant-L—Z—Q  (I')
| Comp | Formula | Ant | L | Z | M | Q | T |
|---|---|---|---|---|---|---|---|
| 3 | I' | IIa | 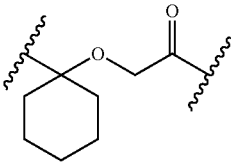 [SMILES: *C(=O)COC1(*)CCCCC1] | —NH— | — | 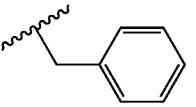 | — |
| 4 | I' | IIa | 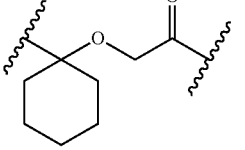 | 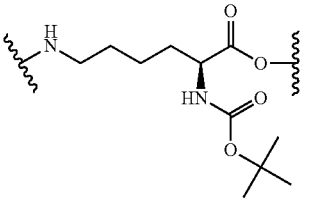 [SMILES: *NCCCC[C@H](NC(=O)OC(C)(C)C)C(=O)O*] | — | H | — |
| 5 | I | IIa | 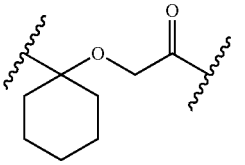 [SMILES: *C(=O)COC1(*)CCCCC1] | —NH— | 6 | — | Mcm2 |
| 6 | I' | IIa | 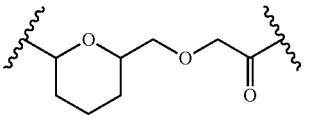 [SMILES: *C(=O)COCC1CCCC(*)O1] | —NH— | — | H | — |
| 7 | I' | IIa | 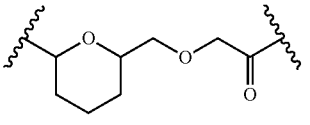 [SMILES: *C(=O)COCC1CCCC(*)O1] | —NH— | — | CH$_3$ | — |
| 8 | I' | IIa | 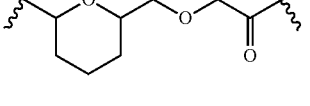 | —NH— | — | 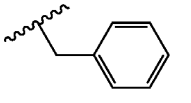 [SMILES: *Cc1ccccc1] | — |
| 9 | I' | IIb | 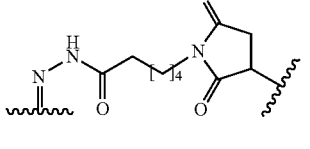 | 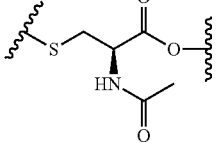 | — | H | — |
| 10 | I' | IIb | 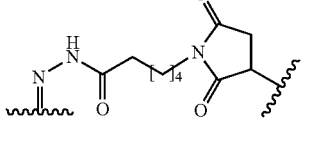 | 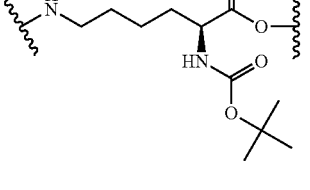 | — | H | — |

TABLE 1-continued

[Ant-L—Z—]$_m$—T (I)

Ant-L—Z—Q (I')

| Comp | Formula | Ant | L | Z | M | Q | T |
|---|---|---|---|---|---|---|---|
| 11 | I | IIb | (structure) | NH | 6 | — | Mcm2 |
| 12 | I' | IIb | (structure) | (structure) | — | H | — |
| 13 | I | IIb | (structure) | S | 1 | — | Mcm2 |
| 14 | I | IIa | (structure) | NH | 6 | — | Mcm2 | wherein the [Ant] residue is represented by a compound of the formula (10a) or (1%) below, that is [Ant] is a residue of an anthracycline of formula IIA as defined above,

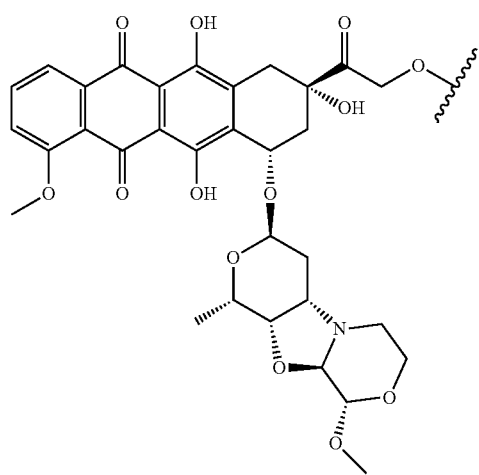

(IIa)

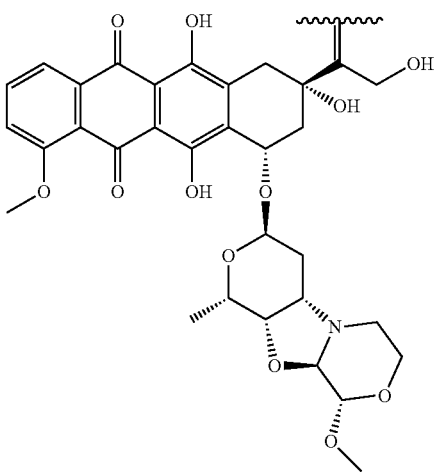

(IIb)

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Pharmaceutically acceptable salts of an anthracycline derivative of the formula (I') or of a conjugate of anthracycline derivatives of the formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, malonic, malic, maleic, fumaric, tartaric, citric, benzoic, cinnamic, mandelic, methanesulphonic, isethionic and salicylic acid. Preferably, the acid addition salt of the compounds of the invention is the hydrochloride or mesylate salt.

Pharmaceutically acceptable salts of an anthracycline derivative of the formula (I') or of a conjugate of anthracycline derivatives of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

As used herein, unless otherwise specified, with the term $C_1$-$C_6$ alkyl means a group such as, for instance, methyl, ethyl, n-propyl, isopropyl, n-butyl, isobutyl, sec-butyl, tert-butyl, n-pentyl, neopentyl, n-hexyl, isohexyl, and the like.

With the term $C_3$-$C_6$ cycloalkyl group means, for instance, cyclopropyl, cyclobutyl, cyclopentyl, cyclohexyl, cyclopentenyl, cyclohexenyl, and the like.

With the term $C_1$-$C_6$ alkylene group means a divalent residue such as, for instance, methylene, ethylene, n-propylene, isopropylene, n-butylene, isobutylene, sec-butylene, tert-butylene, n-pentylene, neopentylene, n-hexylene, isohexylene, and the like.

The term $C_3$-$C_6$ cycloalkylene group means a divalent residue such as, for instance, cyclopropylene, cyclobutylene, cyclopentylene, cyclohexylene, cyclopentenylene, cyclohexenylene, and the like.

It is clear to the skilled man that any of the groups or substituents herein defined may be construed from the names of the groups from which they originate.

As an example, unless specifically noted otherwise, in the $C_1$-$C_5$ alkoxy group, the alkyl moiety includes, for instance, methyl, ethyl, n-propyl, isopropyl, n-butyl, isobutyl, sec-butyl, tert-butyl, n-pentyl, neopentyl and the like. Exemplary $C_1$-$C_5$ alkoxy groups are methoxy (—$OCH_3$), ethoxy (—$OCH_2CH_3$), propyloxy, isopropyloxy, n-butyloxy, isobutyloxy, sec-butyloxy, tert-butyloxy, n-pentyloxy, neopentyloxy and the like.

"A peptide residue constituted from 1 to 4 amino" means a peptide comprising a sequence from one to four natural or synthetic amino acids.

The present invention also provides processes for the preparation of a compound of the formula (I) as defined above.

A compound of the formula (Ia) as defined above and the pharmaceutically acceptable salts thereof may be prepared as depicted in FIG. 2.

Processes for Preparing Anthracycline Derivative Conjugates Formula (Ia)

Accordingly, a first process of the present invention for preparing a compound of the formula (Ia) as defined above and the pharmaceutically acceptable salts thereof, which process comprises the following steps:

Step 1 reacting a compound of formula (II) as defined above with a compound of formula (IX) or (X):

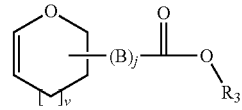

(IX)

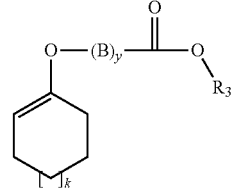

(X)

wherein v, j, k, y, and B are as defined above and $R_3$ is a $C_1$-$C_3$ alkyl group;

Step 2 hydrolyzing the resultant ester intermediate (XI):

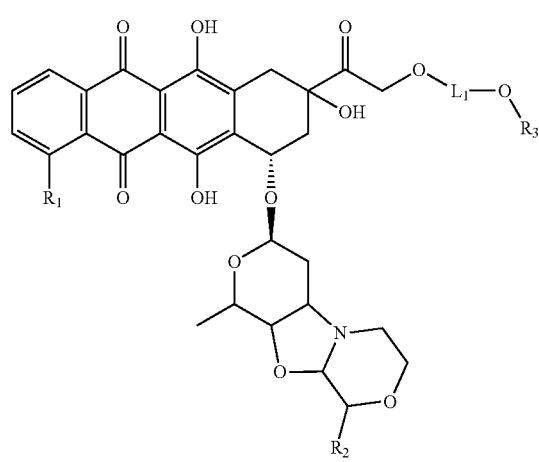

(XI)

wherein $R_1$, $R_2$, $R_3$ are as defined above and $L_1$ is a group of formula (III) or (IV) as defined above;

Step 3 activating the resultant acid of formula (XII):

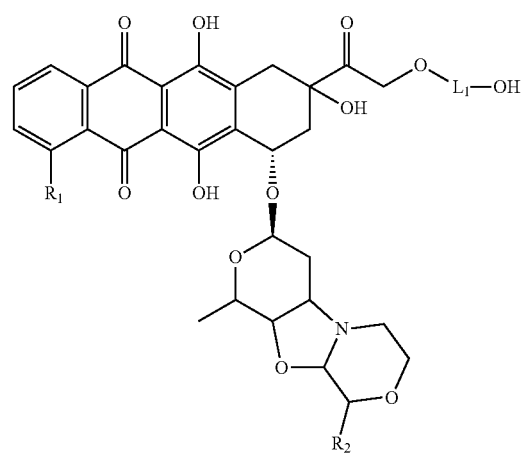

(XII)

wherein $R_1$, $R_2$, and $L_1$ are as defined above and

Step 4 linking the resultant activated compound of formula (XIII):

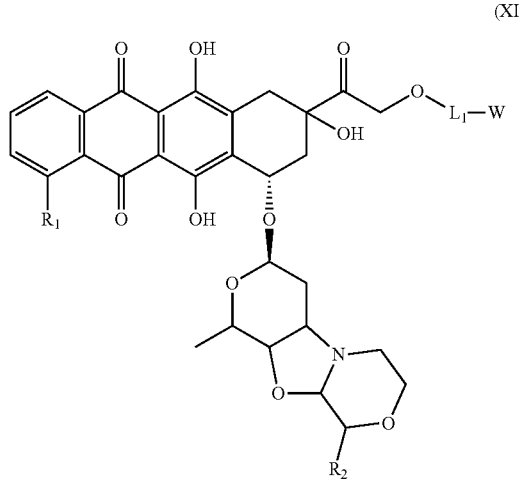

(XIII)

wherein $R_1$, $R_2$, and $L_1$ are as defined above and W is an activating group of the acid group, such as N-oxysuccinimido, N-oxysulfosuccinimido or 2,4-dinitrophenoxy or 2,3,4,5,6-pentafluorophenoxy or t-butoxy carbonyloxy to the desired carrier so to yield compound of formula (Ia), and optionally converting the resultant compound into a pharmaceutically acceptable acid.

The compounds of the formula (XI), (XII) and (XIII) as defined above are also objects of the present invention.

The reaction of step 1 is carried out in a organic solvent e.g. dimethoxyethane or preferably N,N-dimethylformamide (DMF) and in the presence of p-toluenesulfonic acid at a temperature ranging from 0° C. to 80° C. and for a time ranging from 1 hour to 24 hours.

The reaction of step 2 was performed under basic hydrolytic conditions, preferably with a strong base like NaOH, at a temperature of from 0° C. to room temperature from a time ranging from 1 to 48 hours.

The reaction of step 3 was carried out following well known methods, for example the N-oxysuccinimido derivative may be prepared by reaction of the acid (XII) with N-hydroxysuccinimide or its water soluble 3-substituted sodium sulfonate salt in the presence of N,N'-dicyclohexyl-carbodiimide in a solvent such as dichloromethane or N,N-dimethylformamide at a temperature of from 0° C. to 50° C. for a time of from 1 to 24 hours.

Figure 3C:
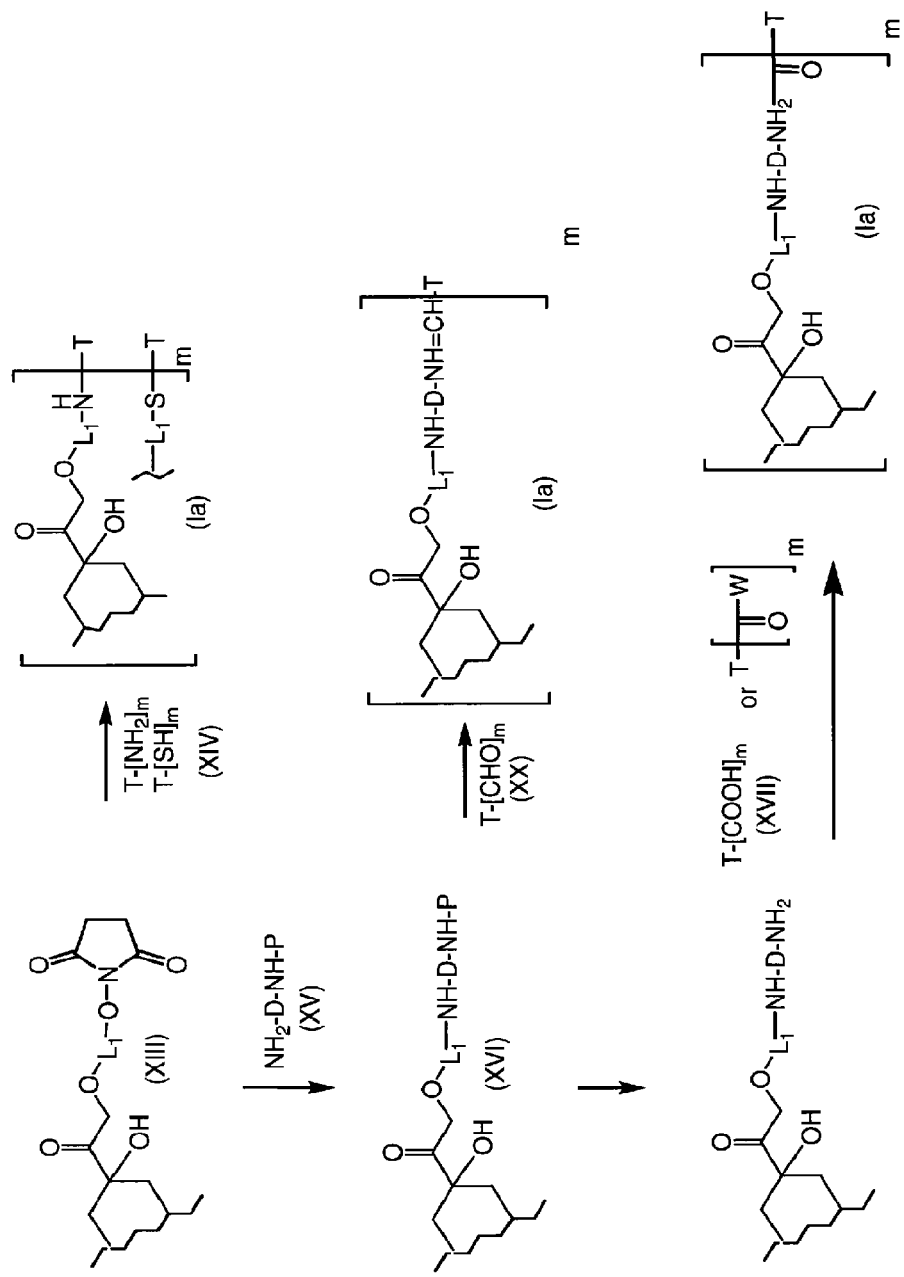
FIG. 3c shows exemplary processeses to prepare Formula Ia compounds by reaction of activated N-hydroxy succinimide (NHS) ester (XIII) with amino or thiol group of carrier T (XIV), e.g. antibody to give amide or thioamide linked anthracycline derivative conjugate (Ia)

The reaction of step 4 can be carried out following one of methods summarized in FIGS. 3a, 3b, 3c, depending on the desired compound of the formula (Ia) as defined above to be obtained:

In particular, the final condensation for preparing a compound of the formula (Ia) as defined above comprises reacting a compound of formula (XIII) as define above with: Ia) a compound of formula T-[X]$_m$ (XIV) wherein X is —NH$_2$ or —SH and m is as defined above, to obtain a compound of the formula (Ia) as defined above under point i) or ii) respectively.

The condensation is carried out in conditions capable of creating covalent linkages of amidic type or thioester type and compatible with the structure of the carrier. Preferred conditions encompass use of buffered aqueous solutions at pH 7-9.5, temperatures from 4° C. to 37° C., for times from some hours to several days.

For example, conditions for the condensation between the compounds of formula (XIII) and antibodies T-NH$_2$ are: aqueous 0.1M sodium phosphate and aqueous 0.1M sodium chloride at pH 8 containing a monoclonal antibody at 1 mg/ml, treated with a 30 fold molar excess of a 10% w/v solution of 6 in N,N-dimethylformamide, for 24 hours at 20 (degree) C. The conjugate is purified by gel filtration on a SEPHADEX G-25 column (Pharmacia Fine Chemical, Piscataway, N.J.), eluting with PBS (phosphate-buffered saline).

Another condensation for preparing a compound of the formula (Ia) as defined above comprises reacting a compound of formula (XIII) as define above with:

1b) a compound of formula (XV) NH$_2$-D-NH—P wherein -D- or -D-NH— are as defined above and P is hydrogen atom or preferably a protecting group 1b') deprotecting the NH function, if necessary, of the resultant compound of formula (XVI):

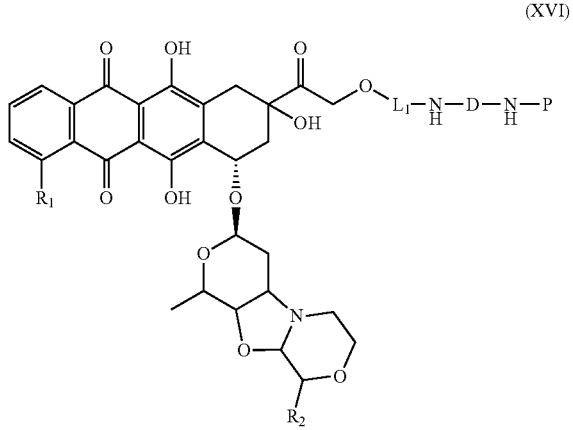

(XVI)

wherein $R_1$, $R_2$, $L_1$ and D are as above reported and P is a protecting group, and then 1"b) coupling the resultant compound of the formula (XVI):

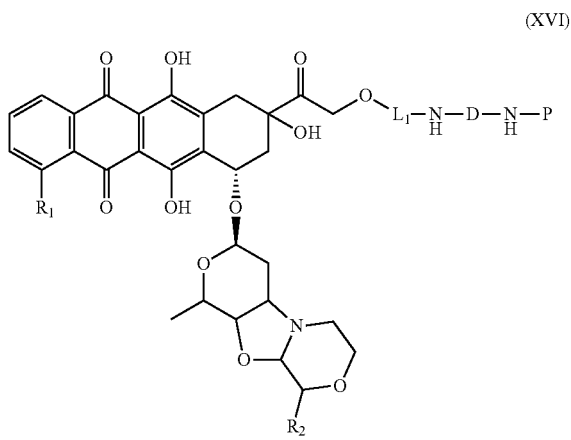

(XVI)

wherein $R_1$, $R_2$, $L_1$ and D are as above reported and P is hydrogen atom, with a carrier residue of formula T-[COOH]$_m$ (XVII) wherein T and m are as defined above, so to obtain compound of formula (Ia) as defined under the point (iii) above wherein [T-Z]— is —NH-D-NHCO-T, $R_1$, $R_2$, $L_1$ and T are as defined above.

The reaction of step 1b is carried out in conditions capable of creating covalent linkages of amidic type and well known in literature and compatible with the structure of the spacer. Preferred conditions encompass use of buffered aqueous solutions pH 7-9.5, or organic solvents such as, e.g. N,N-dimethylformamide, dichloromethane, tetrahydrofuran or ethyl acetate, temperature ranging from 4° C. to 50° C. and for times from some hours to several days.

The optional deprotection of step 1' b is carried out using well known method reported in the literature [see, e.g. Green T. W., Wuts P. G. M in *Protective Groups in Organic Chemistry*]. The coupling reaction of step 1"b is carried out in an organic solvent, preferably N,N-dimethylformamide in the presence of a condensing agent such as e.g. 1-ethyl-3-(3-dimethylaminopropyl)carbodiimide hydrochloride 1,3-di-tert-butylcarbodiimide, N-(3-dimethylaminopropyl)-n'-ethylcarbodiimide, 1-(3-dimethylaminopropyl)-3-ethylcarbodiimide hydrochloride, or preferably N,N'-dicyclohexyl-carbodiimide. The reaction is carried out at a temperature ranging from 5° C. to 50° C. and for a time ranging from 1 hour to 24 hours.

In an alternative way, the compound of formula (XVII) can be activated with a suitable activating acid group W as described above in step 3 above and then coupled with the deprotected amine using the same conditions reported above.

Another condensation for preparing a compound of the formula (Ia) as defined above comprises reacting a compound of formula (XIII) as define above with:

1c) a compound of formula (XVIII) $NH_2$-D-COO—$P_1$ wherein D or D-CO— are as defined above and $P_1$ is a suitable protecting acid group e.g. alkylester that is removed after the coupling reaction to yield the acid compound of formula (XIX):

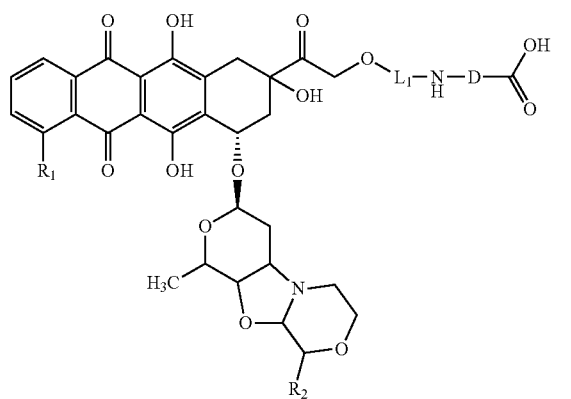

(XIX)

wherein $R_1$, $R_2$, $L_1$ and D are as described above.

The resultant compound of formula (XIX) can be used as such, or preferably activated through a suitable activating acid group as described above in step 3, and then coupled with the carrier residue of formula (XIV) T-[X]$_m$ wherein X is $NH_2$ and m and T are as defined above so to prepare compound of formula (Ia) defined at the point (iv) wherein [T-Z]— is —NH-D-CONH-T, $R_1$, $R_2$, $L_1$ and T are as defined above.

Preferred reaction conditions to couple a compound of the formula (XIII) with a compound of formula (XVIII) as defined above are the same that reported in step 1b above. Removal of the acid protecting group is carried out using well reviewed methods [see, e.g. Green T. W., Wuts P. G. M in *Protective Groups in Organic Chemistry*] for example when the acid function is protected as ethyl ester derivative the deprotection can be carried out under basic hydrolytic conditions preferably using NaOH and at a temperature ranging from 0° C. to room temperature and from a time ranging from 1 hour to 48 hours. Reaction of a compound of the formula (XIX) with compound of formula (XIV) is carried out in organic solvent preferably N,N-dimethylformamide in the presence of a condensing agent such as e.g. 1-ethyl-3-(3-dimethylaminopropyl)carbodiimide hydrochloride 1,3-di-tert-butylcarbodiimide, N-(3-dimethylaminopropyl)-n'-ethylcarbodiimide, 1-(3-dimethylaminopropyl)-3-ethylcarbodiimide hydrochloride, or preferably N,N'-dicyclohexyl-carbodiimide. The reaction is carried out at a temperature ranging from 5° C. to 50° C. and for a time ranging from 1 hour to 24 hours or in an alternative synthetic way activating the acid (XIX) with a suitable activating group as reported in step 3 of the process and then coupling the activated acid with a compound of the formula (XIV) under the synthetic conditions reported above in step 1.

Another condensation for preparing a compound of the formula (Ia) as defined above comprises reacting a compound of formula (XIII) as define above with:

1d) a compound of the formula (XV) as described above, and then coupling the resultant intermediate of the formula (XVI) as defined above wherein P is hydrogen atom, with a carrier residue of the formula T-[CHO]$_m$ (XX), wherein m and T are as defined above, so to obtain a compound of the formula (Ia) described under point (v) above wherein the [T-Z]— residue represents —NH-D-N=CH-T.

Conjugation of deprotected amino derivative of formula (XVI) with a carrier of formula (XX) can be carried out in conditions capable of creating covalent linkages of hydrazone type and compatible with the structure of the carrier. Preferred conditions encompass use of buffered aqueous solutions at pH 4-7.5, alcohols or a mixture thereof, at a temperature of from 4° C. to 37° C., for times from some hours to several days. Conditions for the coupling between the compounds of deprotected derivative of formula (XVI) and antibodies T-CHO are: aqueous 0.1M sodium acetate and aqueous 0.1M sodium chloride at pH 6 containing a monoclonal antibody at 1 mg/ml, treated with a 30 fold molar excess of a 5% w/v solution of 8 in the same buffer, for 24 hours at 20° C. The conjugate is purified by gel filtration as above described.

Another condensation for preparing a compound of the formula (Ia) as defined above comprises reacting a compound of formula (XIII) as define above with:

1e) a compound of the formula (XXI) $NH_2$-D-SH wherein D is as defined above, under the same reaction condition reported in step 1 of the process and then coupling the resultant compound of formula (XXII):

(XXII)

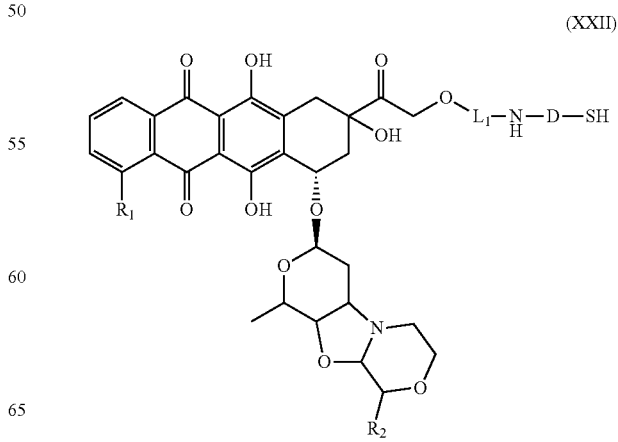

wherein $R_1$, $R_2$, $L_1$ and D are as reported below, either with:

1e') a carrier residue of the formula (V):

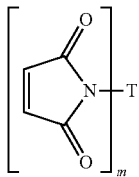

(V)

wherein T and m are as defined above, so to obtain after Michael addition a compound of the formula (Ia) described at the point (vi) wherein [T-Z]— is a residue of the formula (XXIII):

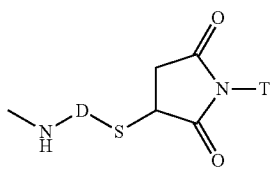

(XXIII)

wherein D and T are as defined above; or

1e") with a carrier residue of the formula (VI):

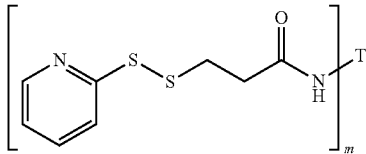

(VI)

wherein T and m are as defined above, so to obtain, after displacement of the pyridine-2-thiol group, a compound of the formula (Ia) defined under point (vii) above wherein [T-Z]— is a residue of formula (XXIV)

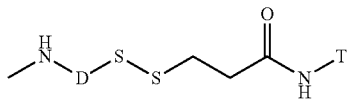

(XXIV)

wherein D and T are as defined above.

The reaction of a compound of the formula (XXII) as defined above with a compound of the formula (V) as defined above can be carried out in buffered aqueous solutions at pH 7-9.5, alcohols or a mixture thereof, at a temperature of from 4° C. to room temperature and for a period of from 1 to 6 hours [see e.g. Willner D. et al, Bioconjugate Chem. (1993) 4:521-527]. Coupling of compound (XXII) with compound (VI) is performed preferably in a mixture of methanol and phosphate buffered solution, at pH 7.2 with from 1 to 1.5 equivalents of a compound of formula (XXII) as defined above for each reacting group of a compound (VI) as defined above. The reaction is incubated preferably at a temperature of from 4° C. to room temperature [see, e.g., EP328147].

A compound of the formula (Ib) as defined above and the pharmaceutically acceptable salts thereof may be prepared as depicted in FIG. 4.

Processes for Preparing Anthracycline Derivative Conjugates Formula (Ib)

Accordingly, the present invention provides a process of for preparing a compound of the formula (Ib) as defined above and the pharmaceutically acceptable salts thereof, which process comprises the following steps:

Step 1 reacting a compound of formula (II) as defined above with an acyl hydrazide derivative of formula (XXV):

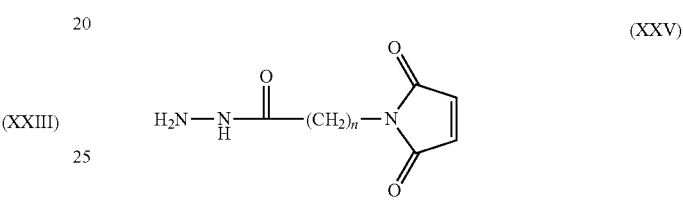

(XXV)

in conditions capable of creating covalent linkages of acyl hydrazone type and compatible with the structure of the carrier; and Step 2 converting the resultant compound of the formula (XXVI):

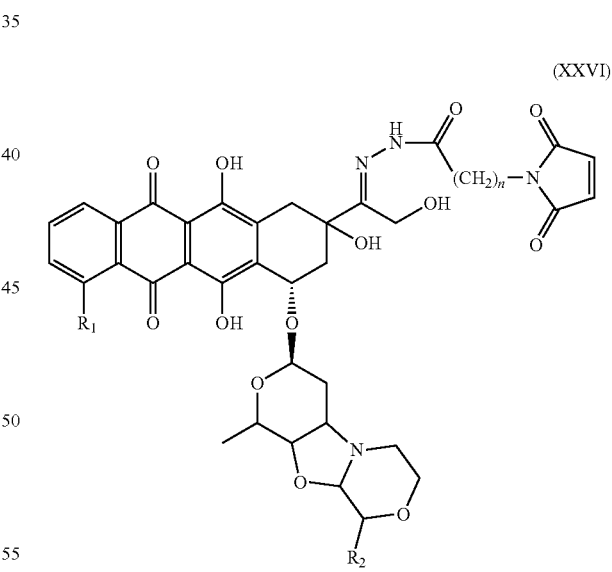

(XXVI)

into a final compound of the formula (Ib) as defined above by an appropriate method.

Another condensation for preparing a compound of the formula (Ib) as defined above comprises reacting a compound of formula (XXVI) as define above with:

2b) a compound of the formula (XXVII) H—$R_4$-D-NH—P wherein D is as defined above, $R_4$ is —NH— or —S— and P is hydrogen atom or, preferably, an amino protecting group that is removed after the coupling reaction, and then 2'b) coupling the resultant acylhydrazone derivative of the formula (XXVIII):

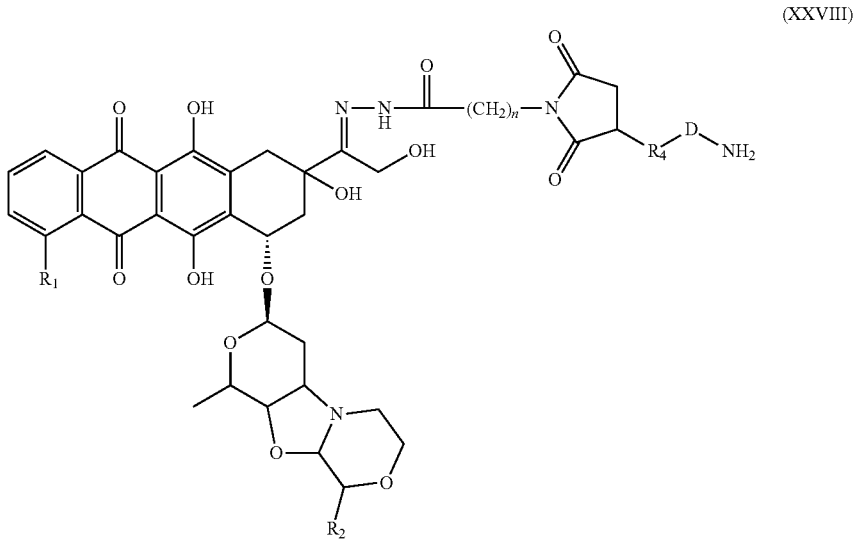

(XXVIII)

wherein $R_1$, $R_2$, $R_4$ and D are as defined above, with a carrier derivative of the formula (XVII) T-[COOH]$_m$, wherein T and m are as defined above, so to yield a compound of formula (Ib) defined at the point (x) and (xv) wherein the [T-Z]— residue is —NH-D-NHCO-T or —S-D-NHCO-T and $R_1$, $R_2$, $L_2$, T are as defined above. Conjugation reaction is carried out using the same conditions reported under point 1b above.

Another condensation for preparing a compound of the formula (Ib) as defined above comprises reacting a compound of formula (XXVI) as define above with:

2c) a compound of the formula (XXIX) H—$R_4$-D-CO—$P_1$ wherein $R_4$, D, D-CO— and $P_1$ are as defined above, and removing the protecting group, if present; and 2'c) coupling the resultant acylhydrazone derivative of the formula (XXX):

wherein $R_1$, $R_2$, $R_4$ and D are as defined above, preferably after activation with a suitable activating acid group W, wherein W is as reported above, with a carrier of the formula (XIV) T-[X]$_m$, wherein X is NH$_2$, and T and m are as defined above, so to yield a compound of the formula (Ib) as defined under points (xi) and (xvi) above wherein the [T-Z]-residue is —NH-D-CONH-T or —S-D-CONH-T and $L_2$, $R_1$, $R_2$, T are as defined above. Conjugation reaction is carried out using the same conditions reported in point (1c) of the process.

Another condensation for preparing a compound of the formula (Ib) as defined above comprises:

2d) coupling the compound of formula (XXVIII) obtained as described above with a carrier of the formula (XX) T-[CHO]$_m$, so as to yield a compound of the formula (Ib) as defined under points (xii) and (xvii) above, wherein the [T-Z]— residue is —NH-D-N=C-T or —S-D-N=C-T and $L_2$, $R_1$, $R_2$, T are as defined above, using the same reaction conditions reported under point 1d above;

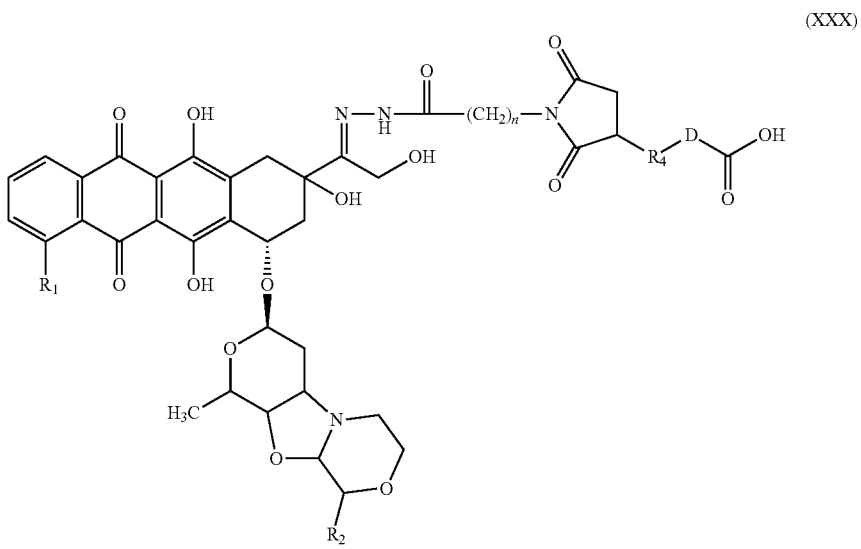

(XXX)

Another condensation for preparing a compound of the formula (Ib) as defined above comprises reacting a compound of formula (XXVI) as define above with:

2e) a compound of the formula (XXXI) H—R$_4$-D-S—P$_2$ wherein R$_4$ and D are as defined above and P$_2$ is hydrogen atom or, preferably, a thiol protecting group, then coupling the resultant compound of the formula (XXXII):

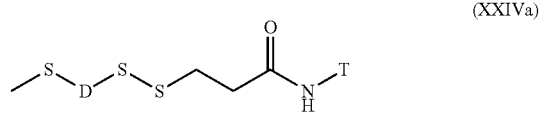

(XXIVa)

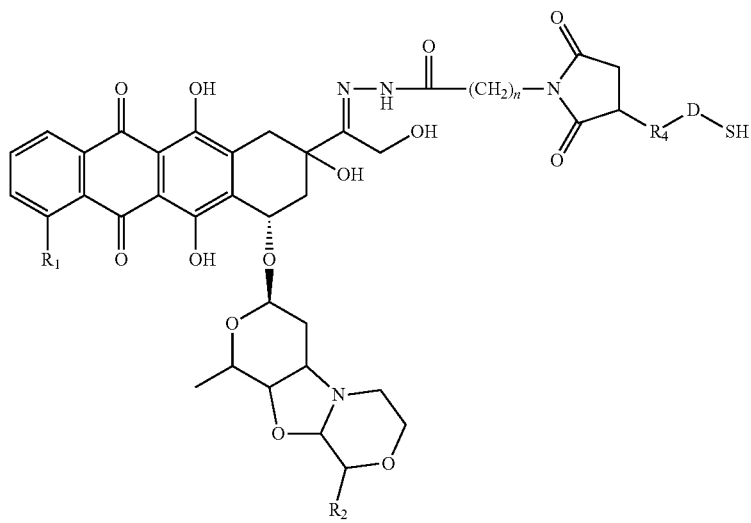

(XXXII)

wherein n, R$_1$, R$_2$, R$_4$ and D are as defined above, after the removal of the thiol protecting group, if present, with either:

2e') a carrier derivative of the formula (V) as defined above, so as to yield a compound of the formula (Ib) as defined under points (xiii) and (xviii) above wherein L$_2$, R$_1$, R$_2$, D, are as defined above and [T-Z]— is a residue of formula (XXIII) as defined above, or (XXIIIa) or,

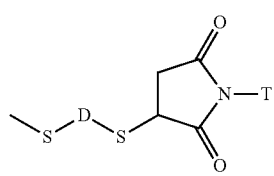

(XXIIIa)

2e'') a carrier derivative of the formula (VI) as defined above, so to yield compound of formula (Ib) defined under points (xiv) and (xix) above wherein L$_2$, R$_1$, R$_2$, D are as defined above and [T-Z]— is a residue of the formula (XXIV) as defined above or (XXIVa).

Conjugation reaction is carried out using the same conditions reported in point (1e) of the process while removal of the selected thiol protecting group can be carried out under the condition reported in the literature [see, e.g. Green T. W., Wuts P. G. M in *Protective Groups in Organic Chemistry*]

A compound of the formula (Ib) wherein L$_2$ is a spacer of formula (VIII) and the pharmaceutically acceptable salts may be obtained by a process depicted in FIG. 6, wherein G is a carbon or nitrogen atom, preferably a nitrogen atom, R$_5$ is halogen or hydrogen atom, preferably hydrogen atom, and n, R$_1$ and R$_2$ are as defined above.

Accordingly, the present invention provides a process for preparing a compound of the formula (Ib) as defined above wherein L$_2$ is a spacer of formula (VIII) and the pharmaceutically acceptable salts thereof, which process comprises the following steps:

Step 1 reacting a compound of the formula (II) as defined above with an acyl hydrazide derivative of formula (XXXIII):

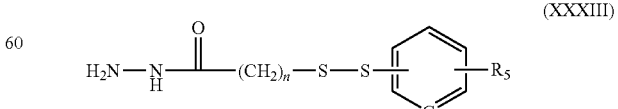

(XXXIII)

wherein G and R$_5$ are as above defined, using the same conditions reported in step 1 as described above in the process for preparing a compound of the formula (Ib), and Step 2 converting the resultant acylhydrazone derivative of the formula (XXXIV):

(XXXIV)

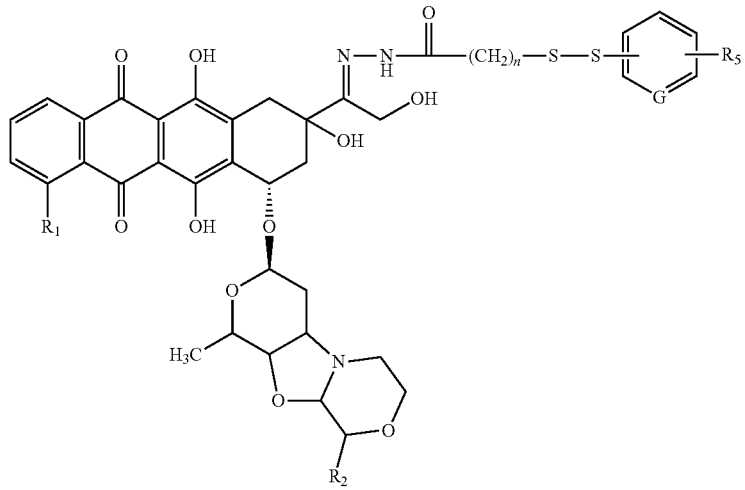

wherein n, $R_1$, $R_2$, and G are as defined above, into a final compound of the formula (Ib) by an appropriate method.

The compound of the formula (XXXIV) as defined above is also object of the present invention.

The final conversion can be carried out following one of the methods summarized in FIGS. 7a, 7b, 7c, wherein n, m, T, D, P, $P_1$, $P_2$ and $R_4$ are as defined above. In particular, the final condensation for preparing a compound of the formula (Ib) as defined above comprises reacting a compound of formula (XXXIV) as defined above with:

(3a) a carrier derivative of the formula (XIV) T-[X]$_m$ wherein X is —SH and m is as defined above, so to yield a compound of the formula (Ib) as defined under point (xx) above, wherein $L_2$ is a linker of the formula (VIII) as defined above, $R_1$ and $R_2$ are as defined above and [T-Z] is —S-T wherein T is as defined above. Reaction conditions to tether the carrier to compound of formula (XXXIV) are the same described under point (1e''') above.

Another condensation for preparing a compound of the formula (Ib) as defined above comprises reacting a compound of formula (XXXIV) as define above with:

(3b) a compound of formula (XXXV) SH-D-NH—P wherein D and P are as defined above under the same conditions described under point 1e' above, and (3'b) coupling the resultant acylhydrazone derivative of the formula (XXXVI), after removal of the amino protecting group, if present:

(XXXVI)

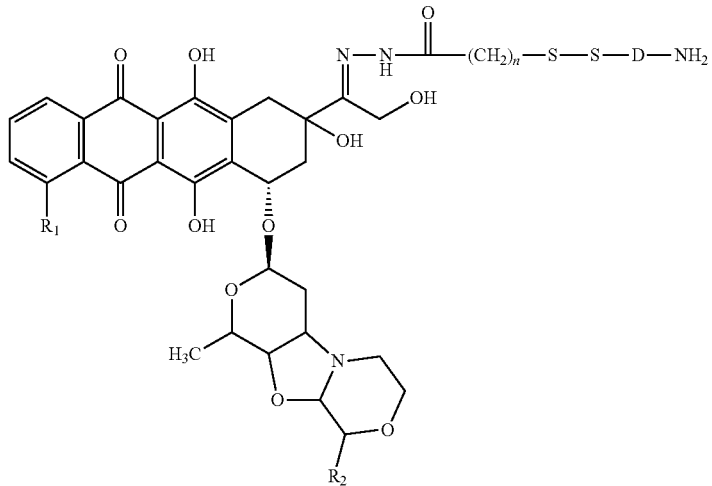

wherein n, $R_1$, $R_2$, and D are as defined above, with a carrier derivative of the formula (XVII) T-[COOH]$_m$, wherein T and m are as defined above, so as to yield a compound of the formula (Ib) as defined under point (xxi) above wherein $L_2$ is as defined above and the [T-Z]— residue is —S-D-NHCO-T. The reaction is carried out using the same conditions that has been used to generate the final compounds under point (1b) above.

Another condensation for preparing a compound of the formula (Ib) as defined above comprises reacting a compound of formula (XXXIV) as define above with:

(3c) a compound of formula (XXXVII) HS-D-CO-0P$_1$ wherein D, and $P_1$ are as defined above, under the same reaction conditions reported under point 1e' and, after removal of the amino protecting group, if present;

(3'c) coupling the resultant acylhydrazone derivative of the formula (XXXVIII), preferably activated by reaction of a suitable activating acid group W, wherein W is a group defined above:

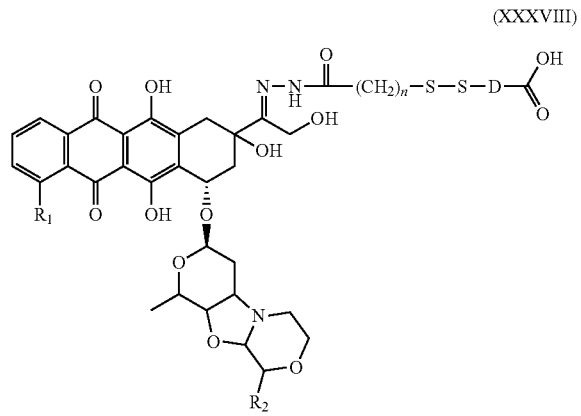

(XXXVIII)

wherein n, $R_1$, $R_2$, and D are as defined above, with a carrier of the formula (XIV) T-[X]$_m$, wherein X is NH$_2$, and T and m are as defined above, so as to yield a compound of formula (Ib) as defined under point (xxii) above wherein the [T-Z]— residue is —S-D-CONH-T and $L_2$, $R_1$, $R_2$, T are as defined, using the same conditions reported under point 1c above.

Another condensation for preparing a compound of the formula (Ib) as defined above comprises:

(3d) coupling a compound of formula (XXXVI) obtained as described above with a carrier derivative of the formula (XX) T-[CHO]$_m$, wherein T and m are as defined above, so as to yield a compound of the formula (Ib) as defined under point (xxiii) above wherein the [T-Z]— residue is —S-D-N=C-T and D, $L_2$, $R_1$, $R_2$, T are as defined above. The reaction conditions are the same reported under point 1d above.

Another condensation for preparing a compound of the formula (Ib) as defined above comprises reacting a compound of formula (XXXIV) as defined above with:

(3e) a compound of the formula (XXXIX) HS-D-S—P$_2$ wherein D and $P_2$ are as defined above, and $P_2$ is preferably a thiol protecting group, under the same conditions reported under point 1e' above, and, after removal of the protecting group, if present, using conditions known in the literature and coupling the resultant acylhydrazone derivative of the formula (XL):

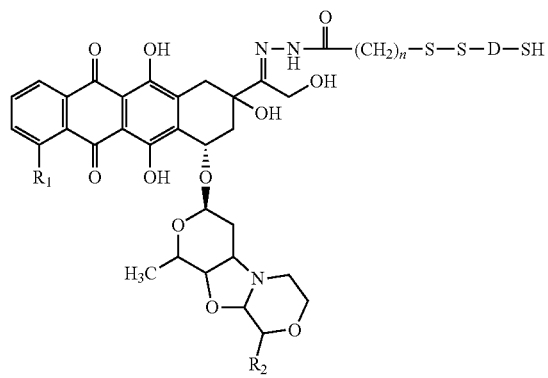

(XL)

wherein n, $R_1$, $R_2$, and D are as defined above, with either:

(3'e) a carrier of the formula (V) as defined above so as to yield a compound of the formula (Ib) as defined under point (xiv) above wherein $L_2$, $R_1$, $R_2$, D, are as defined above and [T-Z]— is a residue of formula (XXIIIa) as defined above, or (3"e) a carrier of the formula (VI) as defined above so as to yield a compound of the formula (Ib) as defined under point (xxv) above wherein $L_2$, $R_1$, $R_2$ and D are as defined above and [T-Z]— is a residue of the formula (XXIVa) as defined above.

The reactions between a compound (XL) as defined above with compound of formula (VII) or (VIII) as defined above are carried out as under the same conditions reported at the point 1e' and 1e" respectively.

The compounds of the present invention of the formula (I') as defined above, wherein L is $L_1$, and the pharmaceutically acceptable salts thereof, may be obtained by a process depicted below in schemes 7-10, wherein all the symbols have the same meanings as defined above.

Scheme 7

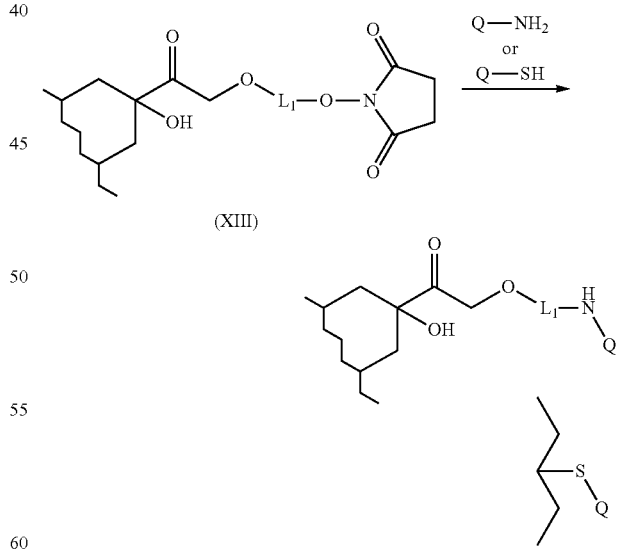

By reacting a compound of the formula (XIII) with a compound of the formula Q-NH$_2$ or Q-SH, wherein Q is as defined above, there are obtained compounds of formula (I') wherein L is $L_1$ and $R_1$, $R_2$, Q and $L_1$ are as defined above. Coupling reaction conditions are the same described above under the point 1a.

Scheme 8

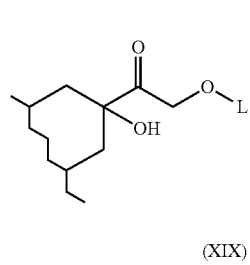

(XIX)

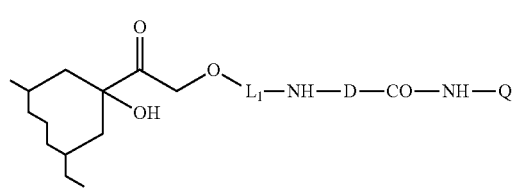

By reacting a compound of the formula (XIX) with a compound of the formula Q-NH$_2$ as defined above there are obtained compounds of the formula (I') wherein L is L$_1$ and R$_1$, R$_2$, Q and D are as defined above. Coupling reaction conditions are the same described above under the point 1c.

Scheme 9

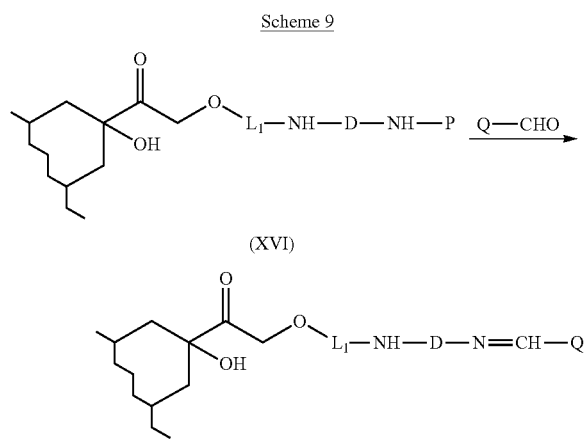

By reacting a compound of the formula (XVI) wherein P is hydrogen atom with a compound of the formula Q-CHO, wherein Q is as defined above, there are obtained compounds of the formula (I') wherein L is L$_1$ and R$_1$, R$_2$, Q, L$_1$ and D are as defined above. Coupling reaction conditions are the same described above under point 1d.

Scheme 10

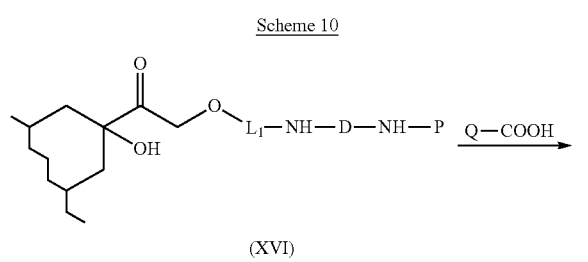

(XVI)

By reacting a compound of the formula (XVI) wherein P is hydrogen atom and L$_1$ and D are as defined above, with a compound of the formula Q-COOH wherein Q is as defined above, there are obtained compounds of formula (I') wherein L is L$_1$ and L$_1$, R$_1$, R$_2$, Q and D are as defined above.

Coupling reaction conditions are the same described above under point 1b. The compounds of the present invention of the formula (I') as defined above, wherein L is L$_2$, and the pharmaceutically acceptable salts thereof, may be obtained by a process depicted below in Schemes 11-15, wherein all the symbols have the same meanings as defined above.

Scheme 11

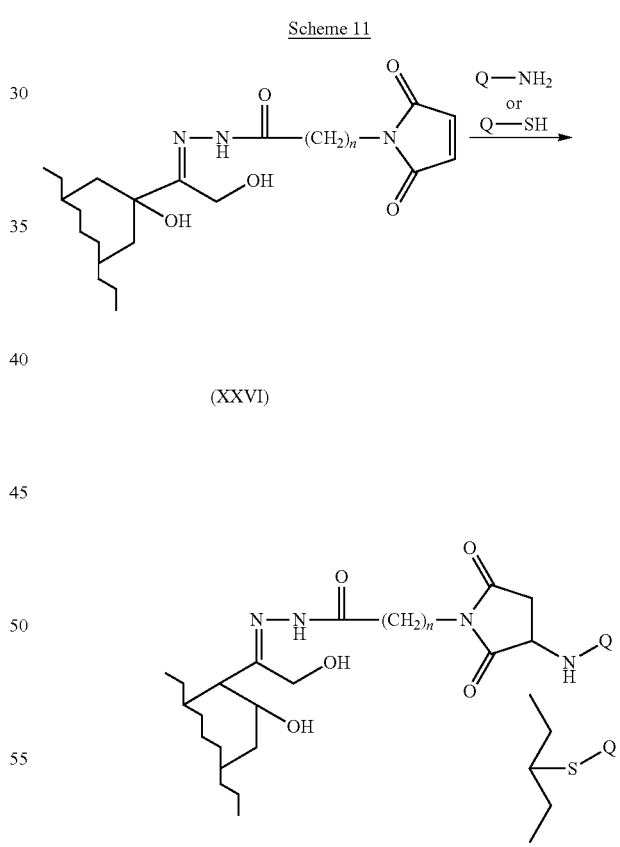

By reacting a compound of the formula (XXVI) with a compound of the formula Q-NH$_2$ or Q-SH as defined above, there are obtained compounds of the formula (I') wherein L is L$_2$, and L$_2$ is of the formula (VII) as defined above and R$_1$, R$_2$, Q are as defined above.

Scheme 12
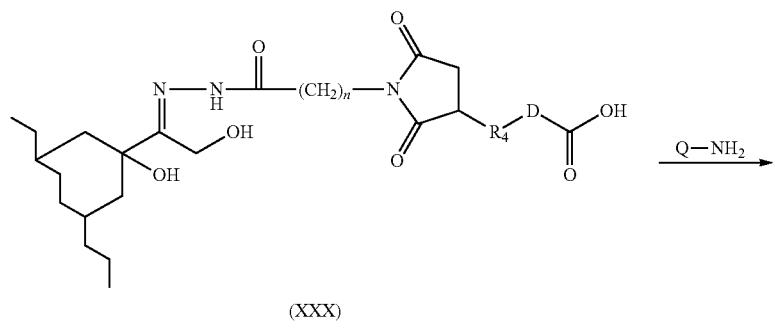
(XXX)
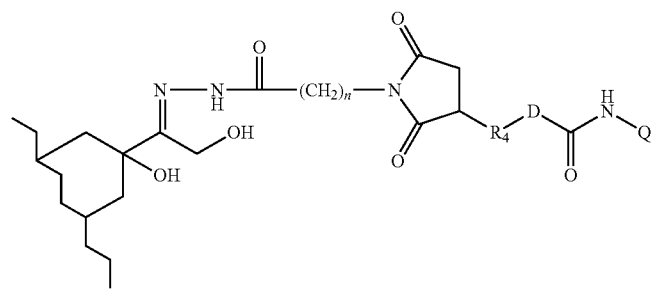
By reacting an acid compound of the formula (XXX) with a compound of the formula Q-NH$_2$ as defined above, there are obtained compounds of the formula (I') wherein L is L$_2$ and L$_2$ is a linker of formula (VII) as defined above and R$_1$, R$_2$, R$_4$, D, Q are as defined above.
Scheme 13
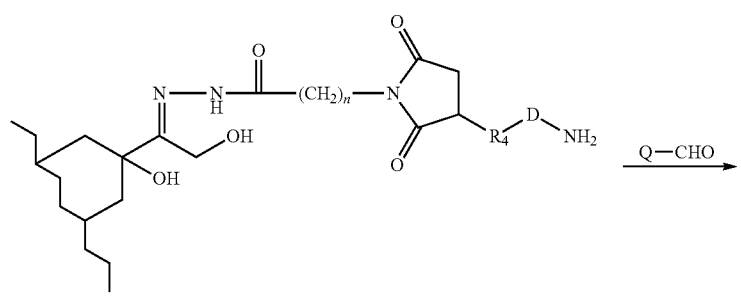
(XXVIII)
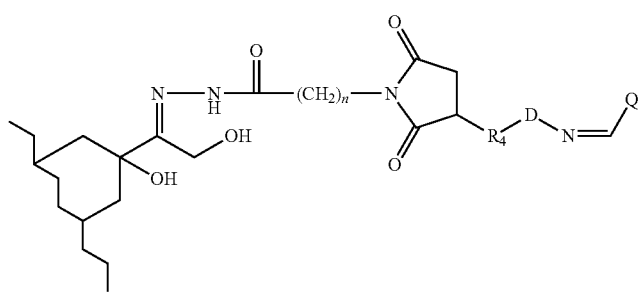

By reacting an acid compound of the formula (XXVIII) with a compound of the formula Q-CHO as defined above, there are obtained compounds of the formula (I') wherein $L_2$ is a linker of formula (VII) as defined above and $R_1$, $R_2$, $R_4$, D, Q are as defined above.

Scheme 14

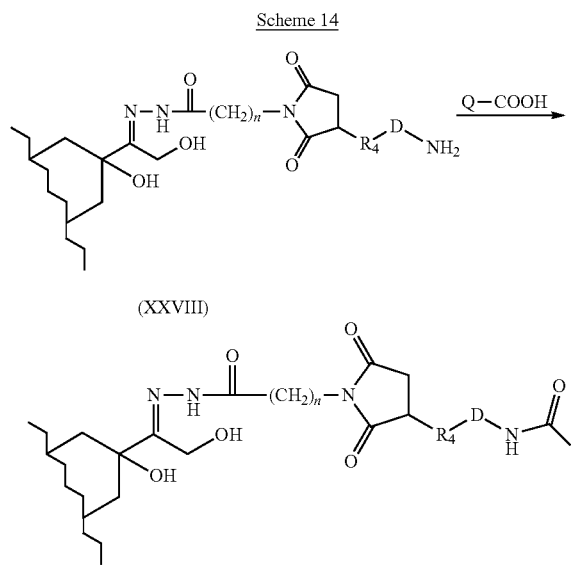

(XXVIII)

By reacting an acid compound of the formula (XXVIII) with a compound of the formula Q-COOH as defined above, there are obtained compounds of the formula (I') wherein L is $L_2$, $L_2$ is a linker of the formula (VII) as defined above and $R_1$, $R_2$, $R_4$, D, Q are as defined above. Coupling reaction conditions described above are the same described under point 1e'.

Scheme 15

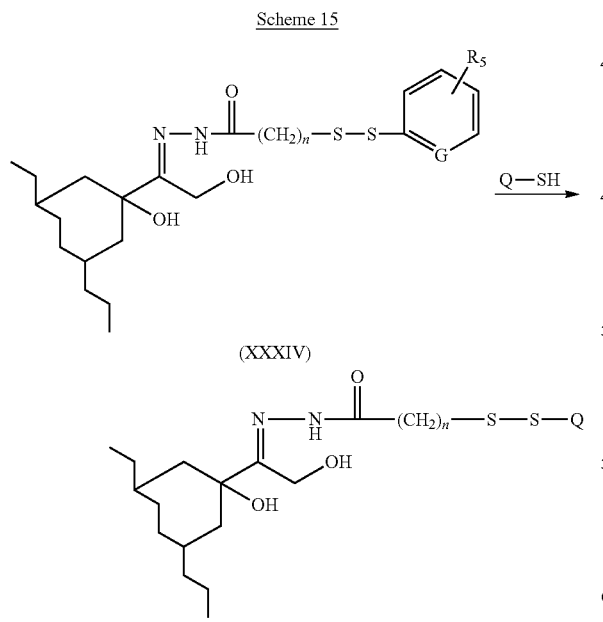

(XXXIV)

By reacting a compound of the formula (XXXIV) with a compound of the formula Q-SH as defined above, there are obtained compounds of the formula (I') wherein L is $L_2$, $L_2$ is a linker of the formula (VIII) as defined above and $R_1$, $R_2$, Q are as defined above.

Scheme 16

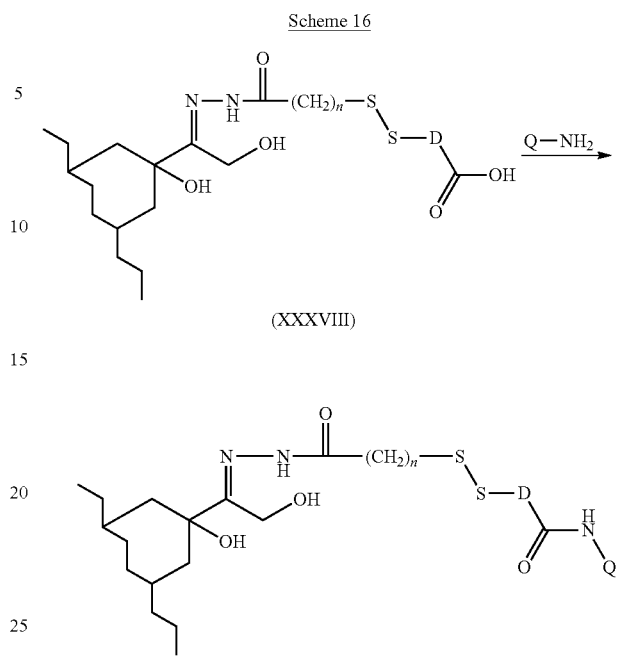

(XXXVIII)

By reacting a compound of the formula (XXXVIII) with a compound of the formula Q-NH$_2$ as defined above, there are obtained compounds of the formula (I') wherein L is $L_2$, $L_2$ is a linker of the formula (VIII) and $R_1$, $R_2$, Q and D are as defined above.

Scheme 17

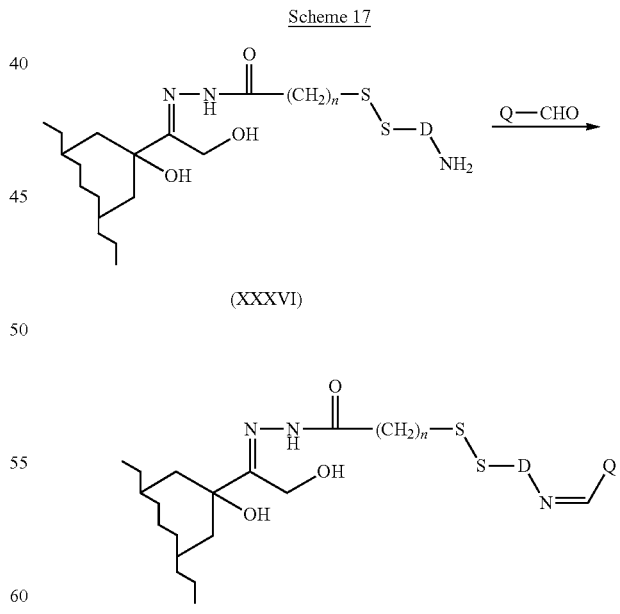

(XXXVI)

By reacting a compound of the formula (XXXVI) with a compound of the formula Q-CHO as defined above, there are obtained compounds of the formula (I') wherein L is $L_2$, $L_2$ is a linker of the formula (VIII) and $R_1$, $R_2$, Q and D are as defined above.

Scheme 18

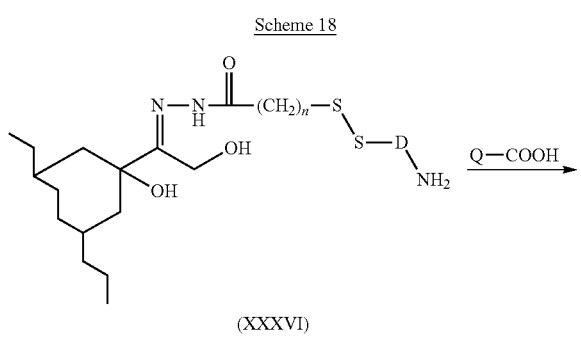

(XXXVI)

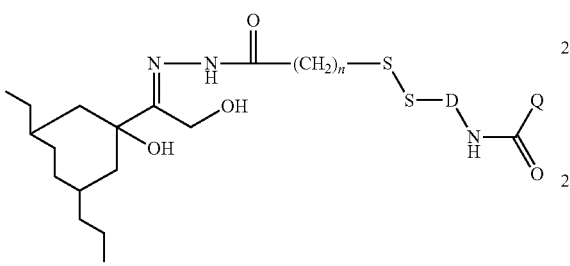

By reacting a compound of the formula (XXXVI) with a compound of the formula Q-COOH as defined above, there are obtained compounds of the formula (I') wherein L is $L_2$, $L_2$ is a linker of the formula (VIII) and $R_1$, $R_2$, Q and D are as defined above. Coupling reaction conditions described above are the same described under point 1e"above.

Starting compounds and reagent are commercially available or can be prepared following known method reported in the literature. For example, the compounds of the formula (II) are described in WO 98/02446, the compounds of the formula (IX) and (X) are described in WO 9202255.

Antibody-Drug Conjugates

The anthracycline derivative conjugate compounds of the invention include those with utility for anticancer activity. In one embodiment, the anthracycline derivative conjugate compounds include an antibody conjugated, i.e. covalently attached by a linker, to an anthracycline derivative drug moiety where the drug when not conjugated to an antibody has a cytotoxic or cytostatic effect. The biological activity of the drug moiety is thus modulated by conjugation to an antibody. Antibody-drug conjugates (ADC) of the invention may selectively deliver an effective dose of a cytotoxic agent to tumor tissue whereby greater selectivity, i.e. a lower efficacious dose may be achieved.

In one embodiment, the bioavailability of the ADC, or an intracellular metabolite of the ADC, is improved in a mammal when compared to the corresponding PNU-159682, anthracycline derivative compound alone. Also, the bioavailability of the ADC, or an intracellular metabolite of the ADC is improved in a mammal when compared to the corresponding antibody alone (antibody of the ADC, without the drug moiety or linker).

In one embodiment, the anthracycline derivative drug moiety of the ADC is not cleaved from the antibody until the antibody-drug conjugate binds to a cell-surface receptor or enters a cell with a cell-surface receptor specific for the antibody of the antibody-drug conjugate. The drug moiety may be cleaved from the antibody after the antibody-drug conjugate enters the cell. The anthracycline derivative drug moiety may be intracellularly cleaved in a mammal from the antibody of the compound, or an intracellular metabolite of the compound, by enzymatic action, hydrolysis, oxidation, or other mechanism.

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p 234-242). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

In one embodiment, an antibody-drug conjugate (ADC) compound comprises an antibody covalently attached by a linker L and an optional spacer Z to one or more anthracycline derivative drug moieties D, the compound having formula (Ic)

$$Ab\text{-}(L\text{-}Z_m\text{-}D)_p \quad \text{Ic}$$

or a pharmaceutically acceptable salt thereof, wherein:

Ab is an antibody;

D is an anthracycline derivative selected from the structures:

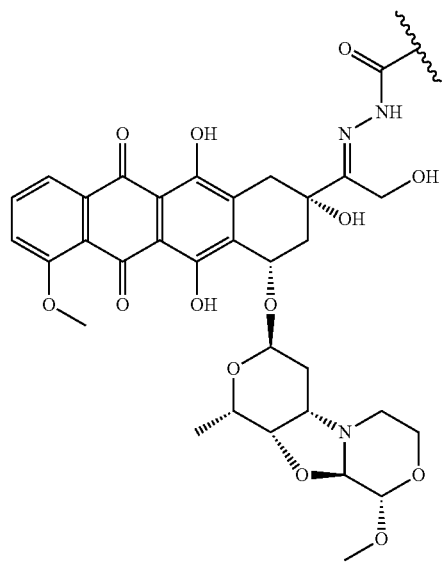

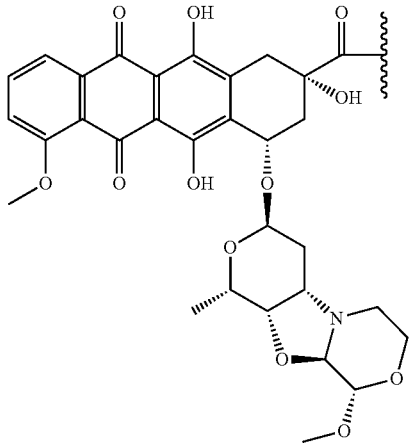

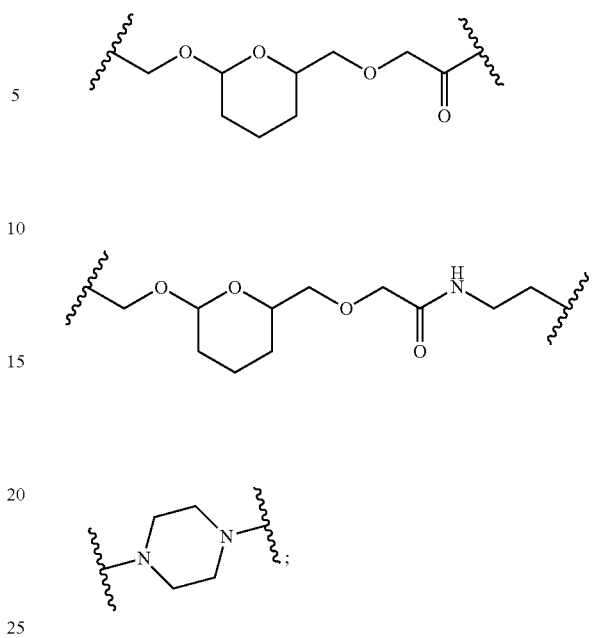

where the wavy line indicates the attachment to L;

L is a linker selected from —N(R)—, —N(R)$_m$(C$_1$-C$_{12}$ alkylene)-, —N(R)$_m$(C$_2$-C$_8$ alkenylene)-, —N(R)$_m$(C$_2$-C$_8$ alkynylene)-, —N(R)$_m$(CH$_2$CH$_2$O)$_n$—, and the structures:

where the wavy lines indicate the attachments to D and Z; and

Z is an optional spacer selected from —CH$_2$C(O)—, —CH$_2$C(O)NR(C$_1$-C$_{12}$ alkylene)-, and the structures:

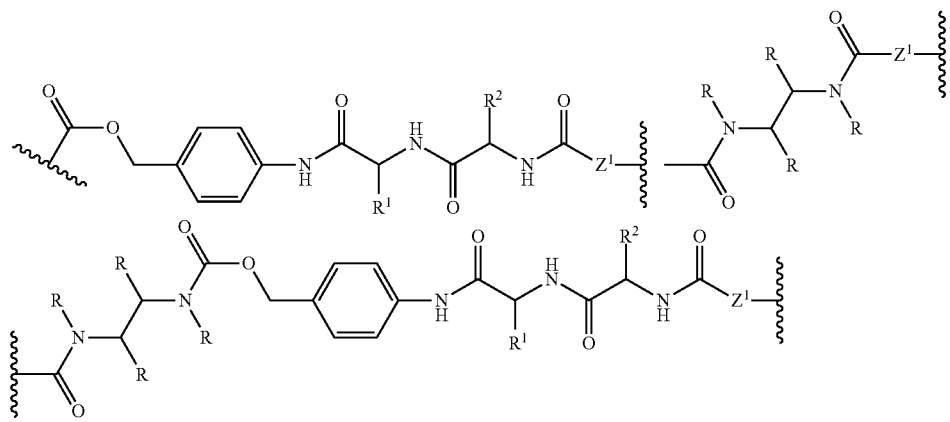

R is H, C$_1$-C$_{12}$ alkyl, or C$_6$-C$_{20}$ aryl;

R$^1$ and R$^2$ are independently selected from an amino acid side chain;

Z$^1$ is selected from —(C$_1$-C$_{12}$ alkylene)-, —(C$_2$-C$_8$ alkenylene)-, —(C$_2$-C$_8$ alkynylene)-, and —(CH$_2$CH$_2$O)$_n$—, m is 0 or 1;

n is 1 to 6; and p is an integer from 1 to 8.

Formula I compounds include all mixtures of variously loaded and attached antibody-drug conjugates where 1, 2, 3, 4, 5, 6, 7, and 8 drug moieties are covalently attached to the antibody.

Exemplary embodiments of antibody-drug conjugates include:
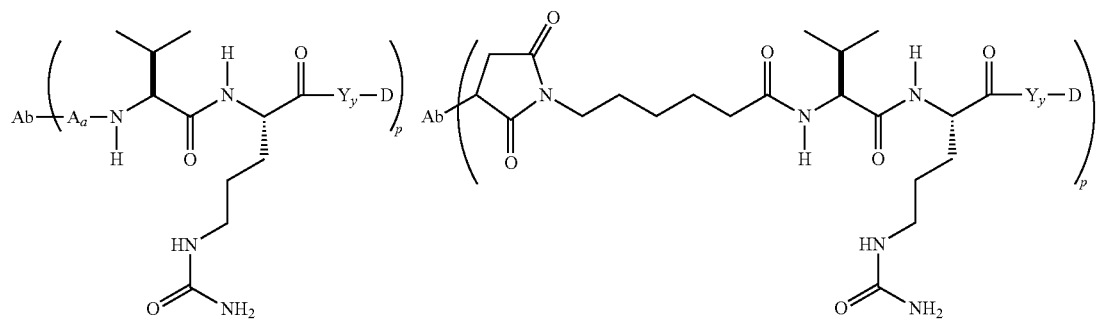
valine-citrulline (val-cit or vc)          MC-val-cit
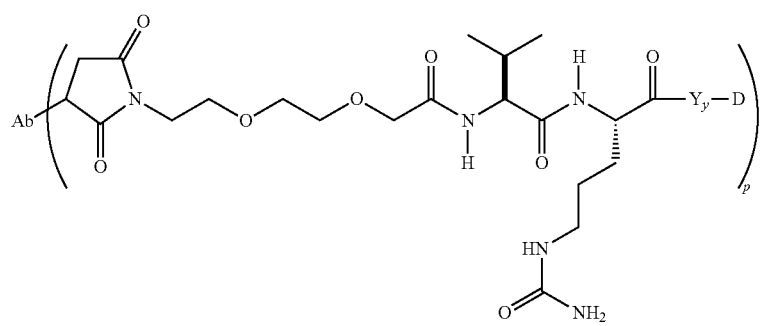
MPEG-val-cit
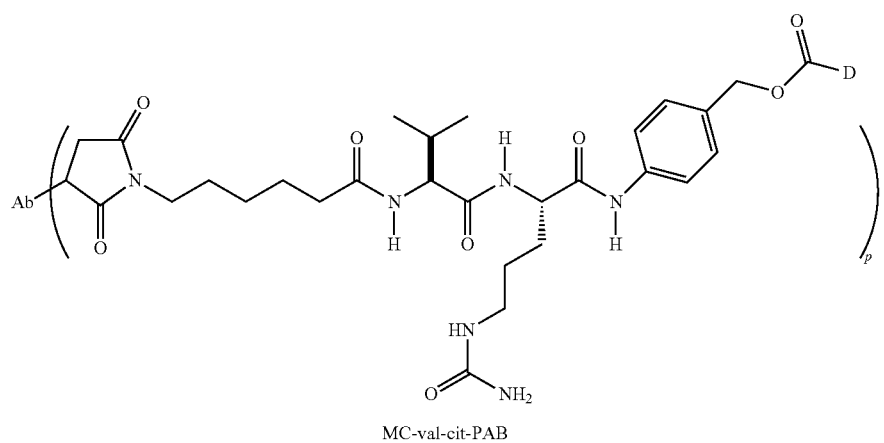
MC-val-cit-PAB
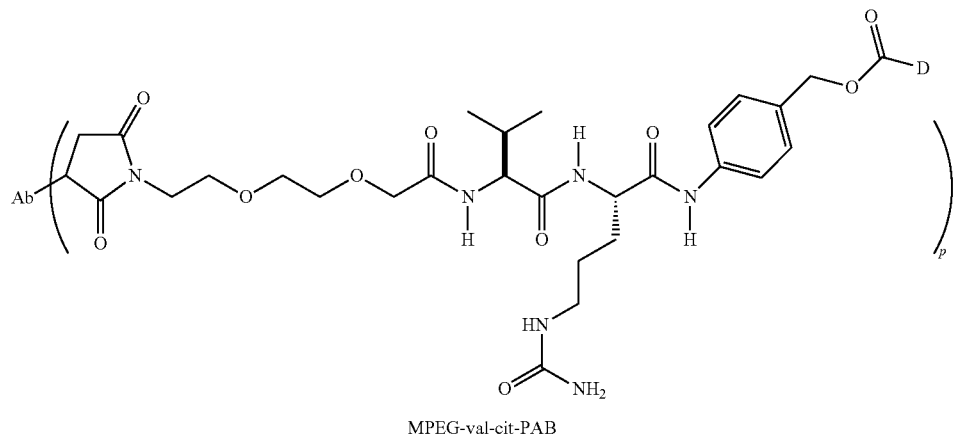
MPEG-val-cit-PAB

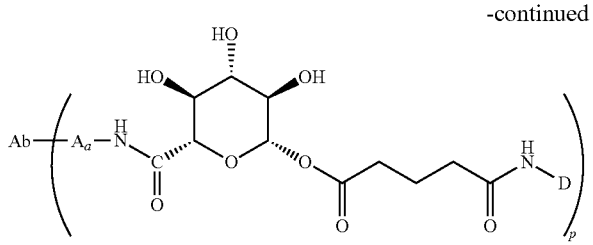

where $A_a$ is a divalent unit, such as MC (maleimidocaproyl), MP (maleimidopropanoyl) or MPEG (2-(2-(2-(2,5-dioxo-2,5-dihydro-1H-pyrrol-1-yl)ethoxy)ethoxy)acetyl), capable of linking an antibody (Ab) to an amino acid unit, such as valine-citrulline; and $Y_y$ is a divalent unit, such as PAB (para-aminobenzyloxycarbonyl) which links an amino acid unit to the drug moiety (D) when an amino acid unit is present. In other embodiments, $A_a$ links $Y_y$ directly to the drug moiety when the amino acid unit is absent. In other embodiments, the $Y_y$ unit links directly the drug moiety to the antibody unit when both the amino acid unit and the $A_a$ unit are absent.

Exemplary antibody-disulfide linker drug conjugates are represented by the structures:

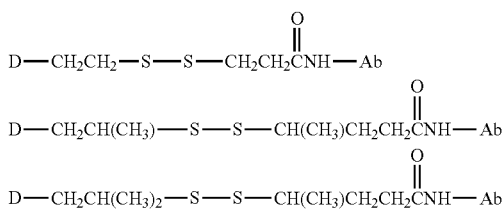

The disulfide linker SPP may be constructed with linker reagent N-succinimidyl 4-(2-pyridylthio) pentanoate.

The antibody-drug conjugates of formula (I) and the compounds of the formula (I') include all enantiomers, diastereomers, isomerically enriched, racemic mixtures, isotopically labelled and isotopically enriched forms (e.g. $^2H$, $^3H$, $^{14}C$, $^{15}N$), and protected forms thereof.

Not to be limited by any particular mechanism of action, the antibody-drug conjugates of formula (I) and the compound of the formula (I') of the present invention may be useful therapeutic agents since they contain an acetalic bond or a hydrazone bond, which releases the parent drug (II) upon hydronium-ion-catalyzed hydrolysis or "in vivo" enzymatic cleavage. It is well known that in malignant tumors there is a high rate of glycolysis compared to normal tissue, causing an increase in the production of lactate and thus a decrease of the pH in the tumor see: H. M. Rauen et al., Z. Naturforsch, Teil B, 23 (1968) 1461. The invention affords a two level specificity of action of the compounds, the first one consisting in a preferential localization of the conjugate in the tumor tissue by means of antigenic recognition, and the second one consisting in a preferential release of the drug in its active form in the tumor tissue by means of preferential acidic cleavage. While not limiting the scope or utility of the compositions or methods of the invention, the acid-sensitive acetal linkers described herein may be cleaved in vivo under localized or systemic acidic conditions, thus separating the targeting antibody from the drug moiety.

The conjugates produced according to the methods described are characterized following different chemical-physical methods. The retention of the original molecular weight and the lack of aggregate formation may be assessed by chromatographic gel filtration procedures (Yu, D. S. et al., J. Urol. 140, 415, 1988) with simultaneous and independent detection of anthracycline and antibody at different wavelengths, and by gel electrophoretic methods. The overall charge distribution of the compounds obtained may be assessed by chromatographic ion exchange methods. The anthracycline concentration may be assessed by spectrophotometric titration against a standard calibration curve obtained from the parent anthracycline. The protein concentration may be assessed by colorimetric assays such as the bicinchonic acid assay (Smith, P. K. et al., Anal. Biochem. 150, 76, 1985) or the Bradford dye assay (Bradford, M. M., (1976) Anal. Biochem. 72:248). The antigen binding activity retention of the antibodies, after the conjugation procedures, may be assessed by an ELISA method (Yu, D. S. et al., J. Urol. 140, 415, 1988) and by cytofluorimetric methods (Gallego, J. et al., Int. J. Cancer 33, 737, 1984). The acid sensitivity of the conjugate may be evaluated by chromatographic methods after incubation of the compounds in suitable buffered solutions.

Drug Loading

The drug loading is represented by p in an antibody-drug conjugate molecule of Formula I, the average number of anthracycline derivative drugs per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC of Formula I include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. Additionally, the antibody must be subjected to denaturing conditions to reveal reactive nucleophilic groups such as lysine or cysteine. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Cysteine amino acids may be engineered at reactive sites in an antibody and which do not form intrachain or intermolecular disulfide linkages (U.S. Pat. No. 7,521,541). The engineered cysteine thiols may react with linker reagents or the drug-linker reagents of the present invention which have thiol-reactive, electrophilic groups such as maleimide or alpha-halo amides to form ADC with cysteine engineered antibodies and the anthracycline derivative drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved and near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more anthracycline derivative drug moieties and where the drug moieties may be attached to the antibody at various amino acid residues.

Preparation of Antibody-Drug Conjugates

The ADC of Formula I may be prepared by several routes, employing organic chemistry reactions, conditions, and reagents known to those skilled in the art, including: (1) reaction of a nucleophilic group or an electrophilic group of an antibody with a bivalent linker reagent, to form antibody-linker intermediate Ab-L, via a covalent bond, followed by reaction with an activated drug moiety reagent; and (2) reaction of a nucleophilic group or an electrophilic group of a drug moiety reagent with a linker reagent, to form drug-linker reagent D-L, via a covalent bond, followed by reaction with the nucleophilic group or an electrophilic group of an antibody. Conjugation methods (1) and (2) may be employed with a variety of antibodies, drug moieties, and linkers to prepare the antibody-drug conjugates of Formula I.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody-drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p 234-242). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Reactive nucleophilic groups may be introduced on the anthracycline derivative compounds by standard functional group interconversions. For example, hydroxyl groups may be converted to thiol groups by Mitsunobu-type reactions, to form thiol-modified drug compounds.

The antibody-drug conjugates in Table 2 were prepared according to the described methods in the Examples and tested for efficacy by in vitro cell proliferation assay and in vivo tumor xenograft growth inhibition.

TABLE 2

Antibody-drug conjugates

| No. | ADC formula | Figures | linker-drug | DAR * |
|---|---|---|---|---|
| 101 | Tr-MCC-DM1 | 12-20, 22, 24, 26, 28, 31 | SMCC-DM1 | 3.4 |
| 102 | thio-HC-Tr-maleimide-ketal-Ant | 12-15, 22, 24, 26, 28, 30, 31 | 51 | 2.18 |
| 103 | thio-HC-Tr-maleimide-hydrazone-Ant | 12-15, 20, 22, 24, 26, 28, 30 | 52 | 2.4 |
| 104 | thio- HC-Tr-thiopyridine-hydrazone-Ant | 16-20, 22, 24, 26, 28 | 53 | 1.25 |
| 105 | thio-HC-Tr-NHS-ketal-Ant | 16-20, 22, 24, 26, 28 | 50 | 1.6 |
| 106 | thio-HC-Tr-MC-vc-PAB-MMAE | 20, 22, 24, 26, 28 | MC-vc-PAB-MMAE | 1.9 |
| 107 | thio- HC-anti-CD22-maleimide-ketal-Ant | 21, 23, 25, 27, 29, 30, 31, 32 | 51 | 2.57 |
| 108 | thio-HC-anti-CD22-maleimide hydrazone-Ant | 21, 23, 25, 27, 29, 30 | 52 | 2.43 |
| 109 | thio-HC-anti-CD22-thiopyridine-hydrazone-Ant | 21, 23, 25, 27, 29, | 53 | 1.43 |
| 110 | anti-CD22-NHS-ketal-Ant | 16-19, 21, 23, 25, 27, 29, | 50 | 2.13 |
| 111 | thio-HC-anti-CD22-MC-vc-PAB-MMAE | 30 | MC-vc-PAB-MMAE | 1.94 |
| 112 | thio-HC-anti-steap1-MC-vc-PAB-MMAE | 32 | MC-vc-PAB-MMAE | 2 |
| 113 | thio-HC-anti-steap1-maleimide-ketal-Ant | 32 | 51 | 1.65 |

* DAR = drug/antibody ratio average

Screening for Antibody-Drug Conjugates (ADC) Directed Against Tumor-Associated Antigens and Cell Surface Receptors Assay methods for detecting cancer cells comprise exposing cells to an antibody-drug conjugate compound, and determining the extent of binding of the antibody-drug conjugate compound to the cells. Formula I ADC compounds which are identified in the animal models and cell-based assays can be further tested in tumor-bearing higher primates and human clinical trials.

Transgenic animals and cell lines are particularly useful in screening antibody-drug conjugates (ADC) that have potential as prophylactic or therapeutic treatments of diseases or disorders involving overexpression of tumor-associated antigens and cell surface receptors, e.g. HER2 (U.S. Pat. No. 6,632,979). Screening for a useful ADC may involve administering candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. Candidate ADC may be screened serially and individually, or in parallel under medium or high-throughput screening format. The rate at which ADC may be screened for utility for prophylactic or therapeutic treatments of diseases or disorders is limited only by the rate of synthesis or screening methodology, including detecting/measuring/analysis of data.

One embodiment is a screening method comprising (a) transplanting cells from a stable breast cancer cell line into a non-human animal, (b) administering an ADC drug candidate to the non-human animal and (c) determining the ability of the candidate to inhibit the formation of tumors from the transplanted cell line. The invention also concerns a method of screening ADC candidates for the treatment of a disease or disorder characterized by the overexpression of a receptor protein comprising (a) contacting cells from a stable breast cancer cell line with a drug candidate and (b) evaluating the ability of the ADC candidate to inhibit the growth of the stable cell line.

One embodiment is a screening method comprising (a) contacting cells from a stable breast cancer cell line with an ADC drug candidate and (b) evaluating the ability of the ADC candidate to induce cell death, induce apoptosis, block heregulin binding, block ligand-stimulated tyrosine phosphorylation, or block ligand activation of HER2. Another embodiment the ability of the ADC candidate to is evaluated. In another embodiment the ability of the ADC candidate to is evaluated.

Another embodiment is a screening method comprising (a) administering an ADC drug candidate to a transgenic non-human mammal that overexpresses, e.g. in its mammary gland cells, a native human protein, e.g. HER2 or a fragment thereof, wherein such transgenic mammal has stably integrated into its genome a nucleic acid sequence encoding the native human protein or a fragment thereof having the biological activity of the native human protein, operably linked to transcriptional regulatory sequences directing its expression, and develops a tumor. Candidate ADC are screened by being administered to the transgenic animal over a range of doses, and evaluating the animal's physiological response to the compounds over time. Administration may be oral, or by suitable injection, depending on the chemical nature of the compound being evaluated. In some cases, it may be appropriate to administer the compound in conjunction with co-factors that would enhance the efficacy of the compound. If cell lines derived from the subject transgenic animals are used to screen for compounds useful in treating various disorders associated with overexpression of certain tumor-associated antigen proteins or cell surface receptors, e.g. HER2-overexpression. To identify growth inhibitory ADC compounds that specifically target HER2, one may screen for ADC which inhibit the growth of HER2-overexpressing cancer cells derived from transgenic animals (U.S. Pat. No. 5,677,171)

In Vitro Cell Proliferation Assay

Generally, the cytotoxic or cytostatic activity of an antibody-drug conjugate (ADC) is measured by: exposing mammalian cells having tumor-associated antigens or receptor proteins to the antibody of the ADC in a cell culture medium; culturing the cells for a period from about 6 hours to about 5 days; and measuring cell viability. Cell-based in vitro assays may be used to measure viability, i.e. proliferation ($IC_{50}$), cytotoxicity ($EC_{50}$), and induction of apoptosis (caspase activation) of the ADC. The CellTiter-Glo® Luminescent Cell Viability Assay is a commercially available (Promega Corp., Madison, Wis.), homogeneous assay method based on the recombinant expression of *Coleoptera* luciferase (U.S. Pat. No. 5,583,024; U.S. Pat. No. 5,674,713; U.S. Pat. No. 5,700, 670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay is conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a well format in 10 minutes after adding reagent and mixing.

The evaluation of the retention of cytotoxicity of conjugates in comparison with the parent drug may be assessed by a test based on the quantification of ATP. A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% CO2 and after 72 hours the plates were processed using CellTiter-Glo assay (Promega) following the manufacturer's instruction.

CellTiter-Glo is a homogenous method based on the quantification of the ATP present, an indicator of metabolically active cells. ATP is quantified using a system based on luciferase and D-luciferin resulting into light generation. The luminescent signal is proportional to the number of cells present in culture. Briefly, 25 μL/well reagent solutions were added to each well and after 5 minutes shacking microplates were read by a luminometer. The luminescent signal is proportional to the number of cells present in culture.

The anti-proliferative effects of antibody-drug conjugates of Formula Ic (Table 6) were measured by the CellTiter-Glo® Assay (Example 9) against the HER2 expressing tumor cell lines in FIGS. 8-29 in 3 day continuous exposure studies.

FIG. 8 shows a plot of SK-BR-3 in vitro cell viability at 3 days versus concentrations of: free drug PNU-159682 continuous exposure, PNU-159682 1 hr incubation, linker drug: NHS-ketal-Ant 50, linker drug: maleimide-ketal-Ant 51, linker drug: maleimide-hydrazone-Ant 52, and linker drug: thiopyridine-hydrazone-Ant 53. The HER2 expression level of SK-BR-3 cells is 3+. SK-BR-3 cell proliferation was most potently inhibited by continuous exposure to PNU-159682. Brief (1 hr) exposure also effectively inhibited growth of SK-BR-3 cells. Hydrazone-linked Ant 52 and 53 were less potent than free Ant, while ketal-linked Ant 50 and 51 linker drug intermediates showed minimal anti-proliferative activity.

FIG. 9 shows a plot of BT-474 in vitro cell viability at 3 days versus concentrations of: free drug: PNU-159682 continuous exposure, free drug: PNU-159682 1 hr incubation, linker drug: NHS-ketal-Ant 50, linker drug: maleimide-ketal-Ant 51, linker drug: maleimide-hydrazone-Ant 52, and linker drug: thiopyridine-hydrazone-Ant 53. The HER2 expression level of BT-474 cells is 3+. BT-474 cell proliferation was most potently inhibited by continuous exposure to PNU-159682. Brief (1 hr) exposure also effectively inhibited growth of BT-474 cells. Hydrazone-linked Ant 52 and 53 showed minimal anti-proliferative activity, while ketal-linked Ant 50 and 51 were inactive.

FIG. 10 shows a plot of MCF7 in vitro cell viability at 3 days versus concentrations of: free drug: PNU-159682 continuous exposure, free drug: PNU-159682 1 hr incubation, linker drug: NHS-ketal-Ant 50, linker drug: maleimide-ketal-Ant 51, linker drug: maleimide-hydrazone-Ant 52, and linker drug: thiopyridine-hydrazone-Ant 53. MCF7 cell proliferation was most potently inhibited by continuous exposure to PNU-159682. Brief (1 hr) exposure also effectively inhibited growth of MCF7 cells. Hydrazone-linked Ant 52 and 53 showed minial anti-proliferative activity, while ketal-linked Ant 50 and 51 were inactive.

FIG. 11 shows a plot of doxorubicin-resistant (DoxRes) HER2 in vitro cell viability at 3 days versus concentrations of: free drug: PNU-159682 continuous exposure, free drug: PNU-159682 1 hr incubation, linker drug: NHS-ketal-Ant 50, linker drug: maleimide-ketal-Ant 51, linker drug: maleimide-hydrazone-Ant 52, and linker drug: thiopyridine-hydrazone-Ant 53. The HER2 expression level of DoxRes HER2 cells is 3+, with high PgP/MDR1. DoxRes/HER2 cell proliferation was most potently inhibited by continuous exposure to PNU-159682. Brief (1 hr) exposure also effectively inhibited growth of AdrRes/HER2 cells. Hydrazone-linked Ant 52 and 53 were less potent than free Ant, while ketal-linked Ant 50 and 51 showed minimal anti-proliferative activity. The DoxRes Her2 cell line is also known as "AdrRes Her2".

FIG. 12 shows a plot of SK-BR-3 in vitro cell viability at 3 days versus concentrations of: trastuzumab, trastuzumab-MCC-DM1 101, thio-trastuzumab (HC A114C)-maleimide ketal-Ant 102, and thio-trastuzumab (HC A114C)-maleimide hydrazone-Ant 103. Thio-Tr-HC-maleimide-hydrazone-Ant 103 showed the most potent anti-proliferative activity on SK-BR-3 cells. Thio-Tr-HC-maleimide-ketal-Ant 102 and Tr-MCC-DM1 101 were equally potent in terms of $IC_{50}$, but treatment of SK-BR-3 cells with 102 resulted in greater cell killing than 101. All conjugates tested were more potent than trastuzumab.

FIG. 13 shows a plot of BT-474 in vitro cell viability at 3 days versus concentrations of: trastuzumab, trastuzumab-MCC-DM1 101, thio-trastuzumab (HC A114C)-maleimide ketal-Ant 102, and thio-trastuzumab (HC A114C)-maleimide hydrazone-Ant 103. Thio-Tr-HC-maleimide hydrazone-Ant 103 showed the most potent anti-proliferative activity on BT-474 cells. Thio-Tr-HC-maleimide-ketal-Ant 102 and Tr-MCC-DM1 101 were equally potent in inhibiting growth of BT-474 cells. All conjugates tested were more potent than trastuzumab.

FIG. 14 shows a plot of MCF-7 in vitro cell viability at 3 days versus concentrations of: trastuzumab, trastuzumab-MCC-DM1 101, thio-trastuzumab (HC A114C)-maleimide ketal-Ant 102, and thio-trastuzumab (HC A114C)-maleimide hydrazone-Ant 103. The HER2 expression level of MCF7 cells is normal. Thio-Tr-HC-maleimide-hydrazone-Ant 103 showed potent anti-proliferative activity on the Her2-normal MCF7 cell line. Trastuzumab, Tr-MCC-DM1 101 and thio-Tr-HC-maleimide-ketal-Ant 102 were not active on MCF7 cells.

FIG. 15 shows a plot of doxorubicin-resistant (DoxRes) HER2 in vitro cell viability at 3 days versus concentrations of: trastuzumab, trastuzumab-MCC-DM1 101, thio-trastuzumab (HC A114C)-maleimide ketal-Ant 102, and thio-trastuzumab (HC A114C)-maleimide hydrazone-Ant 103. Thio-Tr-HC-maleimide-hydrazone-Ant 103 showed potent anti-proliferative activity on DoxRes/HER2 cells, which express high levels of both HER2 and the multi-drug resistance transporter MDR1/PgP. Thio-Tr-HC-maleimide-ketal-Ant 103 was active only at the two highest concentrations tested (3.3 and 10 ug/ml) whereas Tr-MCC-DM1 101 and trastuzumab showed minimal activity on this cell line.

FIG. 16 shows a plot of SK-BR-3 in vitro cell viability at 3 days versus concentrations of: anti-CD22 NHS ketal-Ant 110, trastuzumab, trastuzumab-MCC-DM1 101, and thio-trastuzumab (HC A114C)-NHS-ketal-Ant 105. Thio-Tr-HC-NHS-ketal-Ant 105 and Tr-MCC-DM1 101 showed equivalent potency on SK-BR-3 cell proliferation in terms of $IC_{50}$; with 105 treatment resulting in greater cell killing. The non-targeted control anti-CD22-NHS-ketal-Ant 110 also showed potent anti-proliferative activity on SK-BR-3 cells. All conjugates tested were more potent than trastuzumab.

FIG. 17 shows a plot of BT-474 in vitro cell viability at 3 days versus concentrations of: anti-CD22 NHS ketal-Ant 110, trastuzumab, trastuzumab-MCC-DM1 101, and thio-trastuzumab (HC A114C)-NHS-ketal-Ant 105. Thio-Tr-HC-NHS ketal-Ant 105 showed the most potent anti-proliferative activity on BT-474 cells. Treatment with Tr-MCC-DM1 also resulted in growth inhibition of BT-474 cells. The non-targeted control anti-CD22-NHS-ketal-Ant 110 showed potent anti-proliferative effects on BT-474 cells. All conjugates tested were more potent than trastuzumab.

FIG. 18 shows a plot of MCF-7 in vitro cell viability at 3 days versus concentrations of: anti-CD22 NHS ketal-Ant 110, trastuzumab, trastuzumab-MCC-DM1 101, and thio-trastuzumab (HC A114C)—NHS-ketal-Ant 105. Thio-Tr-HC-NHS-ketal-Ant 105 and anti-CD22-NHS-ketal-Ant 110 showed equivalent activity on low HER2-expressing MCF7 cells. Trastuzumab and Tr-MCC-DM1 101 were not active on MCF7.

FIG. 19 shows a plot of doxorubicin-resistant (DoxRes) Her2 in vitro cell viability at 3 days versus concentrations of: anti-CD22 NHS ketal-Ant 110, trastuzumab, trastuzumab-MCC-DM1 101, and thio-trastuzumab (HC A114C)-NHS-ketal-Ant 105. Thio-Tr-HC-NHS-ketal-Ant 105 and anti-CD22-NHS-ketal-Ant 110 showed equivalent activity on DoxRes/HER2 cells. Tr-MCC-DM1 101 showed modest activity, and trastuzumab had no effect on DoxRes/HER2.

FIG. 20 shows a plot of SK-BR-3 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, and thio-trastuzumab (HC A114C)-MC-vc-PAB-MMAE 106.

FIG. 21 shows a plot of SK-BR-3 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, and PNU-159682 free drug. As previously reported, trastuzumab modestly inhibits the growth of SK-BR-3 cells through a cytostatic mechanism. Non-targeted control ADCs thio-anti-CD22-HC-ketal-Ant 107 and anti-CD22-NHS-ketal-Ant 110 showed anti-proliferative activity only at the highest doses tested. Non-targeted control ADCs thio-anti-CD22-HC-maleimide hydrazone-Ant 108 and thio-anti-CD22-H-thiopyridine-hydrazone-Ant 109 showed equivalent potency for inhibiting SK-BR-3 cell growth as the HER2-targeted ADCs (FIG. 20), indicating lability of hydrazone-linked ADCs. Free drug PNU-159682, administered in nM concentrations, caused cytotoxicity at all doses tested.

FIG. 22 shows a plot of BT-474 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, and thio-trastuzumab (HC A114C)-MC-vc-PAB-MMAE 106. All ADCs tested showed similar activity on BT-474 cell proliferation. Thio-Tr-HC-vc-MMAE 106 had the lowest $IC_{50}$ (0.01 ng/ml), while treatment with thio-Tr-HC-maleimide-hydrazone-Ant 103 and thio-Tr-HC-thiopyridine-hydrazone-Ant 104 resulted in the greatest amount of total growth inhibition.

FIG. 23 shows a plot of BT-474 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, and PNU-159682 free drug. As previously reported, trastuzumab modestly inhibits the growth of BT-474 cells through a cytostatic mechanism. Non-targeted control ADCs thio-anti-CD22-HC-ketal-Ant 107 and anti-CD22-NHS-ketal-Ant 110 had no anti-proliferative effect on BT-474 cells. Non-targeted control ADCs thio-anti-CD22-HC-maleimide hydrazone-Ant 108 and thio-anti-CD22-H-thiopyridine-hydrazone-Ant 109 showed equivalent potency for inhibiting BT-474 cell growth as the HER2-targeted ADCs (FIG. 22), indicating lability of hydrazone-linked ADCs. Free drug PNU-159682, administered in µM concentrations, caused cytotoxicity at all doses tested.

FIG. 24 shows a plot of MCF-7 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A 114C)-NHS-ketal-Ant 105, trastuzumab-MCC-DM1 101, and thio-trastuzumab (HC A114C)-MC-vc-PAB-MMAE 106. Only thio-Tr-HC-maleimide-hydrazone-Ant 103 and thio-Tr-HC-thiopyridine-Ant 104 had anti-proliferative effects on HER2-low MCF7 cells, indicating lability of hydrazone-linked ADCs. All other ADCs tested (thio-Tr-HC-vc-MMAE 106, Tr-MCC-DM1 101, thio-Tr-HC-maleimide-ketal-Ant 102 and thio-Tr-NHS-ketal-Ant 105) had no effect on MCF7 cell growth.

FIG. 25 shows a plot of MCF-7 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, and PNU-159682 free drug. Consistent with previous reports, trastuzumab was completely inactive on low HER2-expressing MCF7 cells. Non-targeted control ADCs thio-anti-CD22-HC-maleimide-ketal-Ant 107 and thio-anti-CD22-NHS-ketal-Ant 110 also did not inhibit growth of MCF7 cells, indicating lack of drug release from stable ketal linkers. Hydrazone-linked non-targeted control ADCs 108 and 109 showed anti-proliferative effects on MCF7 cells, indicating release of drug from labile hydrazone-linked ADCs. Free drug PNU-159682 administered in nM doses, caused cytotoxicity at all concentrations tested.

FIG. 26 shows a plot of doxorubicin-resistant (DoxRes)/HER2 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, and thio-trastuzumab (HC A 114C)-MC-vc-PAB-MMAE 106. While 106 had no effect and Tr-MCC-DM1 101 had minimal effect on growth of DoxRes/HER2 cells, ketal-linked ADC 102 and 105 were active only at the highest concentrations tested, while hydrazone-linked ADC 103 and 104 potently inhibited growth of DoxRes/HER2 cells FIG. 27 shows a plot of doxorubicin-resistant (DoxRes)/HER2 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A 114C)-thiopyridine hydrazone-Ant 109, anti-CD22-NHS-ketal-Ant 110, and PNU-159682 free drug. Trastuzumab alone had no effect on growth of DoxRes/HER2 cells. Ketal-linked non-targeted control ADC 107 and 110 inhibited growth of DoxRes/HER2 cells only at the highest concentrations tested, while hydrazone-linked non-targeted control ADC 108 and 109 showed potent anti-proliferative activity on DoxRes/HER2 cells. Activities of all four non-targeted anti-CD22-Ant control ADC were similar to HER2-targeted thio-Ant ADC (FIG. 26). Free drug PNU-159682, administered in µM doses, inhibited growth at all concentrations tested.

FIG. 28 shows a plot of doxorubicin-resistant (DoxRes)/HER2 in vitro cell viability at 3 days versus concentrations of: thio-trastuzumab (HC A114C)-maleimide ketal-Ant 102, thio-trastuzumab (HC A114C)-maleimide hydrazone-Ant 103, thio-trastuzumab (HC A114C)-thiopyridine hydrazone-Ant 104, thio-trastuzumab (HC A114C)-NHS-ketal-Ant 105, trastuzumab-MCC-DM1 101, and thio-trastuzumab (HC A 114C)-MC-vc-PAB-MMAE 106, all administered in the presence of verapamil (10 µg/m). Verapamil inhibits efflux of diverse drugs known to be substrates of the multi-drug resistance transporter MDR1/P-glycoprotein (PgP), which is highly expressed on DoxRes/HER2 cells. Addition of verapamil rendered the DoxRes/HER2 cells sensitive to the cytotoxic effects of Tr-MCC-DM1 101, indicating that DM1 is a substrate for MDR1/PgP. Verapamil had no effect on the response to the other ADCs tested (102-106), indicating that the drug effects of these ADCs are not inhibited by NDR1/PgP.

FIG. 29 shows a plot of doxorubicin-resistant (DoxRes)/HER2 in vitro cell viability at 3 days versus concentrations of: trastuzumab, thio-anti-CD22 (HC A114C)-maleimide ketal-Ant 107, thio-anti-CD22 (HC A114C)-maleimide hydrazone-Ant 108, thio-anti-CD22 (HC A114C)-thiopyridine hydrazone-Ant 109, anti-CD22-NHS-ketal-Ant 110, and PNU-159682 free drug, all administered in the presence of verapamil. All ADCs tested (107-110) were equally active in the presence of verapamil (compare to FIG. 27), indicating that the Ant drug is not a substrate of MDR1/PgP.

Table 3 summarizes the $IC_{50}$ values (ug/ml) for inhibition of SK-BR-3, BT-474, MCF7, doxorubicin-resistant (DoxRes), and doxorubicin-resistant (DoxRes) with verapamil cell proliferation of the test compounds of FIGS. 20-29. Comparing SK-BR-3 and BT-474 to MCF7, the maleimide-ketal-Ant and NHS-ketal-Ant ADC show target-dependent killing whereas hydrazone-linked-Ant ADC show target-independent, non-selective killing.

TABLE 3 in vitro inhibition of SK-BR-3, BT-474, MCF7, doxorubicin-resistant (DoxRes),
and doxorubicin-resistant (DoxRes) with verapamil cell proliferation

| Test compound | IC50 (ug/ml) SK-BR-3 FIGS. 20, 21 | IC50 (ug/ml) BT-474 FIGS. 22, 23 | IC50 (ug/ml) MCF7 FIGS. 24, 25 | IC50 (ug/ml) Adr-res HER2 FIGS. 26, 27 | IC50 (ug/ml) Adr-res HER2 + verapamil FIGS. 28, 29 |
|---|---|---|---|---|---|
| thio-trastuzumab (HC A114C)-maleimide ketal-Ant 102 | 0.0014 | 0.0341 | — | 1.5 | 0.284 |
| thio-trastuzumab (HC A114C)-maleimide hydrazone-Ant 103 | 0.0022 | 0.032 | 0.1102 | 0.005 | 0.005 |
| thio-trastuzumab (HC A114C)-thiopyridine hydrazone-Ant 104 | 0.005 | 0.0897 | 0.1390 | 0.009 | 0.014 |
| thio-trastuzumab (HC A114C)-NHS-ketal-Ant 105 | 0.014 | 0.0369 | — | 5.662 | 0.4 |
| trastuzumab-MCC-DM1 101 | 0.0032 | 0.0287 | — | — | 0.021 |
| thio-trastuzumab (HC A114C)-MC-vc-PAB-MMAE 106 | 0.0036 | 0.0075 | — | — | — |
| trastuzumab | — | — | — | — | — |
| thio-anti-CD22 (HC A114C)-maleimide ketal-Ant 107 | 1.588 | — | — | 4.827 | 2.541 |
| thio-anti-CD22 (HC A114C)-maleimide hydrazone-Ant 108 | 0.0025 | 0.049 | 0.0437 | 0.005 | 0.006 |
| thio-anti-CD22 (HC A114C)-thiopyridine hydrazone-Ant 109 | 0.011 | 0.1331 | 0.1367 | 0.015 | 0.015 |
| anti-CD22-NHS-ketal-Ant 110 | 1.615 | — | — | 3.254 | 1.685 |
| PNU-159682 free drug | — | — | — | — | — |

The anti-proliferative effects of antibody-drug conjugates of Formula Ic (Table 6) were measured by the CellTiter-Glo® Assay (Example 9) against CD22 positive, B-lymphoma cell lines: BJAB, GRANTA, DoHH2 and SuDHL4 in 3 day continuous exposure studies. Jurkat cells (CD22 negative) were treated with the antibody-drug conjugates as a negative control.

Table 4 summarizes the $IC_{50}$ values (ug/ml) for inhibition of BJAB, GRANTA, DoHH2 SuDHL4 and Jurkat cell lines by test antibody-drug conjugate compounds in 3 day continuous exposure studies. The anti-CD22 antibody-drug conjugates 107-110 showed highly potent cell killing effects. Significant cell killing was observed with negative control anti-HER2 antibody drug conjugates 102-105. Significant cell killing was observed with anti-CD22 antibody-drug conjugates 107-110 on CD22 negative Jurkat cells.

TABLE 4 in vitro inhibition of BJAB, GRANTA, DoHH2 SuDHL4 and Jurkat cell lines

| test ADC | IC50 (ug/ml) BJAB | IC50 (ug/ml) GRANTA | IC50 (ug/ml) DoHH2 | IC50 (ug/ml) SuDHL4 | IC50 (ug/ml) JURKAT |
|---|---|---|---|---|---|
| thio-trastuzumab (HC A114C)-maleimide ketal-Ant 102 | 0.9863 | 0.3318 | 0.2053 | 0.7990 | 2.2985 |
| thio-trastuzumab (HC A114C)-maleimide hydrazone-Ant 103 | $<1.28 \times 10^{-6}$ | $<1.28 \times 10^{-6}$ | $<1.28 \times 10^{-6}$ | $<1.28 \times 10^{-6}$ | $2.09 \times 10^{-5}$ |
| thio-trastuzumab (HC A114C)-thiopyridine hydrazone-Ant 104 | >10 | >10 | >10 | >10 | >10 |
| thio-trastuzumab (HC A114C)-NHS-ketal-Ant 105 | 0.01197 | 0.00265 | 0.00189 | 0.00966 | 0.02811 |
| thio-anti-CD22 (HC A114C)-maleimide ketal-Ant 107 | 0.000312 | $<1.28 \times 10^{-6}$ | $<1.28 \times 10^{-6}$ | $<1.28 \times 10^{-6}$ | 0.001446 |
| thio-anti-CD22 (HC A114C)-maleimide hydrazone-Ant 108 | $<1.28 \times 10^{-6}$ | $<1.28 \times 10^{-6}$ | $<1.28 \times 10^{-6}$ | $<1.28 \times 10^{-6}$ | $4.60 \times 10^{-5}$ |
| thio-anti-CD22 (HC A114C)-thiopyridine hydrazone-Ant 109 | $9.83 \times 10^{-5}$ | $<1.28 \times 10^{-6}$ | $<1.28 \times 10^{-6}$ | 0.000105 | 0.000412 |
| anti-CD22-NHS-ketal-Ant 110 | 0.001217 | 0.000219 | 0.000125 | 0.001066 | 0.004702 |

In Vivo Serum Clearance and Stability in Mice

Serum clearance and stability of ADC may be investigated in nude, naive (without tumors received by exogenous grafts) mice according to the procedures in Example 10. A difference in the amount of total antibody and ADC indicates cleavage of the linker and separation of the antibody from its drug moiety.

Stability of the conjugates was studied using HPLC analysis. The conjugate was incubated in ammonium acetate buffers at pH 4 and 5.2 at 37° C. Each solution was then taken periodically and applied to an HPLC column using a method reported above. The amount of material released from the conjugate was determined and expressed as percent of released material.

In Vivo Efficacy

Figure 32:
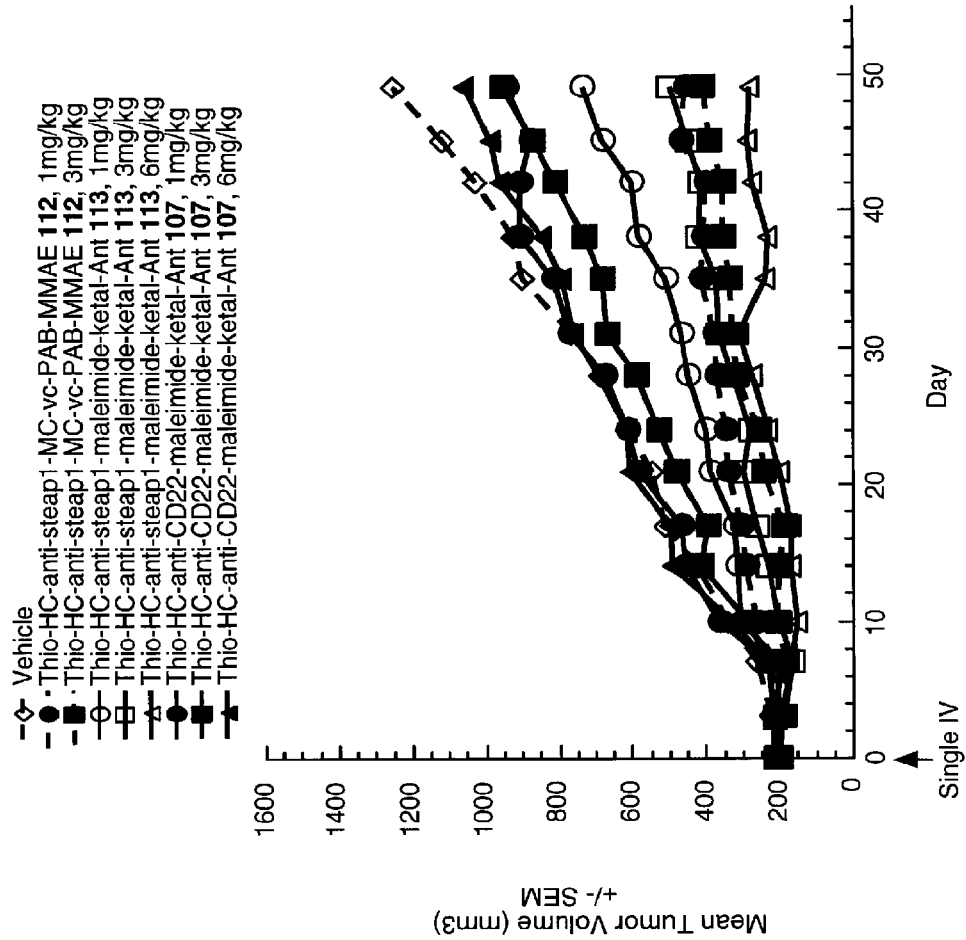
FIG. 32 shows a plot of the in vivo mean tumor volume change over time in LnCap-Ner xenograft tumors inoculated into male SCID-beige mice after single iv dosing on day 0 with: (1) Vehicle, (2) thio-anti-steap1 (HC A114C)-MC-vc-PAB-MMAE 112 1 mg/kg, (3) thio-anti-steap1 (HC A114C)-MC-vc-PAB-MMAE 112 3 mg/kg, (4) thio-anti-steap1 (HC A114C)-maleimide ketal-Ant 113 1 mg/kg, (5) thio-anti-steap1 (HC A114C)-maleimide ketal-Ant 113 3 mg/kg, (6) thio-anti-steap1 (HC A114C)-maleimide ketal-Ant 113 6 mg/kg, (7) thio-anti-CD22 (HC A114C)-maleimide ketal-Ant 107 1 mg/kg, (8) thio-anti-CD22 (HC A114C)-maleimide ketal-Ant 107 3 mg/kg, (9) thio-anti-CD22 (HC A114C)-maleimide ketal-Ant 107 6 mg/kg

The therapeutic effect of the antibody-drug conjugate (ADC) compounds and the improvement of their therapeutic efficacy in comparison with the parent drug, were assessed in animal models of human transplanted tumors. Mice bearing xenografts of human tumors were treated with suitable doses of antibody-drug conjugates, of PNU-159682 free drug, and naked antibody, at certain doses, and the tumor growth was recorded and compared in the different treatment groups. FIGS. 30-32 show the efficacy of the antibody-drug conjugates of Formula Ic by xenograft tumor inhibition in mice.

The efficacy of the antibody-drug conjugates of the invention may be measured in vivo by implanting allografts or xenografts of cancer cells or primary tumors in rodents and treating the tumors with ADC according to the procedures of Example 12. Variable results are to be expected depending on the cell line, the specificity of antibody binding of the ADC to receptors present on the cancer cells, dosing regimen, and other factors. For example, the in vivo efficacy of anti-HER2 ADC may be measured by a high expressing HER2 transgenic explant mouse model. An allograft may be propagated from the Fo5 mmtv transgenic mouse which does not respond to, or responds poorly to, HERCEPTIN® therapy. Subjects are treated once with ADC and monitored over 3-6 weeks to measure the time to tumor doubling, log cell kill, and tumor shrinkage. Follow up dose-response and multi-dose experiments may be further conducted.

FIG. 30 shows a plot of the in vivo mean tumor volume change over time in Burkitt's lymphoma Bjab-luc xenograft tumors inoculated into CB17 SCID mice after single dosing on day 0 with: (1) Vehicle, (2) thio-anti-CD22 (HC A114C)-MC-vc-PAB-MMAE 111 1 mg/kg, (3) thio-trastuzumab (HC A114C)-maleimide ketal-Ant 102 1 mg/kg, (4) thio-trastuzumab (HC A114C)-maleimide ketal-Ant 102 5 mg/kg, (5) thio-anti-CD22 (HC A114C)-maleimide ketal-Ant 107 1 mg/kg, (6) thio-anti-CD22 (HC A114C)-maleimide ketal-Ant 107 5 mg/kg, (7) thio-trastuzumab (HC A114C)-maleimide hydrazone-Ant 103 1 mg/kg, (8) thio-anti-CD22 (HC A114C)-maleimide hydrazone-Ant 108 1 mg/kg, (9) PNU-159682 free drug 8.77 ug/kg. All of the anti-CD22 conjugates (107, 108 and 111) showed target-specific tumor growth inhibition and the inhibitory activity of the ketal-linked anti-CD22 ADC 107 was dose-dependent. Free drug PNU-159682 and non-targeted control ADCs (102 and 103) at the equivalent dose had no effect on tumor growth.

Table 5 shows the drug exposure level, average drug loading, tumor incidence, and responses for each test compound treated group of FIG. 30 in the 48 day in vivo Bjab-luc xenograft tumor efficacy study. The Bjab-luc (EBV-negative Burkitt's lymphoma, luciferase expressing Bjab cells) tumors express CD22 receptor protein (Polson et al (2009) Cancer Res. 69(6):2358-2364; US 2008/0050310; US 2005/0276812). CD22 is expressed only in the B-cell compartment and on the surface of most NHL cells (D'Arena et al (2000) Am J Hematol. 64:275-81; Olejniczak et al (2006) Immunol Invest. 35:93-114). Efficacy in inhibiting the Bjab-luc xenograft tumor in mice as a model system may predict the clinical response in treating patients with hematopoietic malignancies such as non-Hodgkins lymphoma. All of the anti-CD22 ADC (107, 108, 111) were effective in tumor inhibition as compared with Vehicle and control ADC (102 and 103) that did not bind the Bjab-luc cells. The absence of activity with control ADC indicates that the activity seen with the targeted ADC is specific, for example, it is not due to systemic release of free drug. In several cases, tumors were not only inhibited, but also partially and completely regressed by anti-CD22 conjugates (107, 108, 111). These data indicate that anti-CD22 surface antigen is a potentially effective target for the anthracycline-derivative ADC of the invention.

TABLE 5 in vivo Bjab-luc xenograft tumor efficacy study (FIG. 30)

| Test compound dose | drug exposure ug/m2 | avg. drug loading | TI - tumor incidence | PR - partial tumor regression | CR - complete tumor regression |
|---|---|---|---|---|---|
| (1) Vehicle | — | — | 9/9 | 0 | 0 |
| (2) thio-anti-CD22 (HC A114C)-MC-vc-PAB-MMAE 111 1 mg/kg | 28.66 | 1.94 | 8/8 | 1 | 1 |
| (3) thio-trastuzumab (HC A114C)-maleimide ketal-Ant 102 1 mg/kg, | 26.65 | 2 | 9/9 | 0 | 0 |
| (4) thio-trastuzumab (HC A114C)-maleimide ketal-Ant 102 5 mg/kg | 133.25 | 2 | 9/9 | 0 | 0 |
| (5) thio-anti-CD22 (HC A114C)-maleimide ketal-Ant 107 1 mg/kg | 26.42 | 2 | 9/9 | 0 | 0 |
| (6) thio-anti-CD22 (HC A114C)-maleimide ketal-Ant 107 5 mg/kg | 132.08 | 2 | 9/9 | 3 | 0 |
| (7) thio-trastuzumab (HC A114C)-maleimide hydrazone-Ant 103 1 mg/kg | 22.65 | 1.7 | 9/9 | 0 | 0 |
| (8) thio-anti-CD22 (HC A114C)-maleimide hydrazone-Ant 108 1 mg/kg | 22.45 | 1.7 | 9/9 | 1 | 1 |
| (9) PNU-159682 free drug 8.77 ug/kg | 26.42 | — | 9/9 | 0 | 0 |

FIG. 31 shows a plot of the in vivo mean tumor volume change over time in MMTV-HER2Fo5 mammary allograft tumors inoculated into CRL nu/nu mice after single dosing on day 0 with: (1) Vehicle, (2) trastuzumab-MCC-DM1 101 5 mg/kg, (3) trastuzumab-MCC-DM1 101 10 mg/kg, (4) thio-trastuzumab (HC A114C)-maleimide ketal-Ant 102 5 mg/kg, (5) thio-trastuzumab (HC A114C)-maleimide ketal-Ant 102 10 mg/kg, (6) thio-anti-CD22 (HC A114C)-maleimide ketal-Ant 107 5 mg/kg, (7) thio-anti-CD22 (HC A114C)-maleimide ketal-Ant 107 10 mg/kg, (8) trastuzumab-MCC-DM1 101 5 mg/kg+thio-trastuzumab (HC A114C)-maleimide ketal-Ant 102 5 mg/kg. All of the anti-Her2 conjugates (101 and 102) showed target-specific tumor growth inhibition and the inhibitory activity was dose-dependent. Non-targeted control ADC 107 at equivalent doses had no effect on tumor growth.

Table 6 shows the tumor growth inhibition at day 7, drug exposure level, average drug loading, tumor incidence and responses for each test compound treated group of FIG. 31 in the 38 day in vivo MMTV-HER2Fo5 mammary allograft tumor efficacy study (Phillips et al (2008) Cancer Res. 68(22):9280-9290; US 2005/0276812). The MMTV-HER2 Fo5 mammary allograft tumor is a trastuzumab-insensitive, HER2-overexpressing breast cancer cell line. The targeted anti-HER2 ADC (101, 102, and combination of 101 and 102) were effective in tumor inhibition as compared with Vehicle and control ADC (107) that did not bind the MMTV-HER2 Fo5 cells. The absence of activity with control ADC indicates that the activity seen with the targeted ADC is specific, for example, it is not due to systemic release of free drug. Tumors were not only inhibited, but also partially and completely regressed by anti-HER2 conjugates (101, 102, and combination of 101 and 102). Combination trastuzumab-MCC-DM1 101 and thio-trastuzumab (HC A114C)-maleimide-ketal-Ant 102 showed no additional response beyond that of single agent 102. These data indicate that anti-HER2 surface antigen is a potentially effective target for the anthracycline-derivative ADC of the invention.

TABLE 6 in vivo MMTV-HER2 Fo5 mammary allograft tumor efficacy study (FIG. 31)

| Test compound dose | % inhibition at day 7 | drug exposure ug/m2 | avg. drug loading | TI - tumor incidence | PR - partial tumor regression | CR - complete tumor regression |
|---|---|---|---|---|---|---|
| (1) Vehicle | — | — | — | 8/8 | 0 | 0 |
| (2) trastuzumab-MCC-DM1 101 5 mg/kg | 72 | 290 | 3.5 | 6/6 | 0 | 0 |
| (3) trastuzumab-MCC-DM1 101 10 mg/kg | 86 | 580 | 3.5 | 6/6 | 0 | 0 |

TABLE 6-continued in vivo MMTV-HER2 Fo5 mammary allograft tumor efficacy study (FIG. 31)

| Test compound dose | % inhibition at day 7 | drug exposure ug/m2 | avg. drug loading | TI - tumor incidence | PR - partial tumor regression | CR - complete tumor regression |
|---|---|---|---|---|---|---|
| (4) thio-trastuzumab (HC A114C)-maleimide ketal-Ant 102 5 mg/kg | 87 | 110 | 1.5 | 6/7 | 3 | 2 |
| (5) thio-trastuzumab (HC A114C)-maleimide ketal-Ant 102 10 mg/kg | 91 | 215 | 1.5 | 5/7 | 3 | 4 |
| (6) thio-anti-CD22 (HC A114C)-maleimide ketal-Ant 107 5 mg/kg | 18 | 125 | 1.75 | 8/8 | 0 | 0 |
| (7) thio-anti-CD22 (HC A114C)-maleimide ketal-Ant 107 10 mg/kg | 5 | 250 | 1.75 | 8/8 | 0 | 0 |
| (8) combination: trastuzumab-MCC-DM1, 101 5/mg/kg and thio-trastuzumab (HC A114C)-maleimide ketal-Ant 102, 5 mg/kg | 88 | 290 + 110 | 3.5 + 1.5 | 6/7 | 2 | 2 |

FIG. 32 shows a plot of the in vivo mean tumor volume change over time in LnCap-Ner xenograft tumors inoculated into male SCID-beige mice after single dosing on day 0 with: (1) Vehicle, (2) thio-anti-steap1 (HC A114C)-MC-vc-PAB-MMAE 112 1 mg/kg, (3) thio-anti-steap1 (HC A114C)-MC-vc-PAB-MMAE 112 3 mg/kg, (4) thio-anti-steap1 (HC A114C)-maleimide ketal-Ant 113 1 mg/kg, (5) thio-anti-steap1 (HC A114C)-maleimide ketal-Ant 113 3 mg/kg, (6) thio-anti-steap1 (HC A114C)-maleimide ketal-Ant 113 6 mg/kg, (7) thio-anti-CD22 (HC A114C)-maleimide ketal-Ant 107 1 mg/kg, (8) thio-anti-CD22 (HC A114C)-maleimide ketal-Ant 107 3 mg/kg, (9) thio-anti-CD22 (HC A114C)-maleimide ketal-Ant 107 6 mg/kg. All of the anti-steap1 conjugates (112 and 113) showed target-specific tumor growth inhibition and the inhibitory activity of the ketal-linked anti-steap1 ADC 113 was dose-dependent. Non-targeted control ADC 107 at equivalent doses had no effect on tumor growth.

Table 7 shows the drug exposure level, average drug loading, tumor incidence and responses for each test compound treated group of FIG. 32 in the 49 day in vivo LnCap-Ner xenograft tumor efficacy study. Steap1 (six-transmembrane epithelial antigen of the prostate) is a prostate-specific cell-surface antigen highly expressed in human prostate tumors (Hubert et al (1999) PNAS 96(25):14523-14528). The LnCap cell line highly expresses steap1. The LnCap-Ner xenograft (Jin et al (2004) Cancer Res. 64:5489-5495) tumor inhibition study in mice may be an effective predictor for treatment of prostate cancer in patients. The targeted anti-steap1 ADC (112 and 113) were effective in tumor inhibition as compared with Vehicle and control ADC (107) that did not bind the LnCap cells. The absence of activity with control ADC indicates that the activity seen with the targeted ADC is specific, for example, it is not due to systemic release of free drug. Tumors were not only inhibited, but also partially regressed by anti-HER2 conjugates (112 and 113). These data indicate that anti-steap1 surface antigen is a potentially effective target for the anthracycline-derivative ADC of the invention.

TABLE 7 in vivo LnCap-Ner xenograft tumor efficacy study (FIG. 32)

| Test compound dose | drug exposure ug/m2 | avg. drug loading | TI - tumor incidence | PR - partial tumor regression | CR - complete tumor regression |
|---|---|---|---|---|---|
| (1) Vehicle | — | — | 8/8 | 0 | 0 |
| (2) thio-anti-steap1 (HC A114C)-MC-vc-PAB-MMAE 112 1 mg/kg | 30.95 | 2 | 8/8 | 1 | 0 |
| (3) thio-anti-steap1 (HC A114C)-MC-vc-PAB-MMAE 112 3 mg/kg | 92.85 | 2 | 8/8 | 1 | 0 |
| (4) thio-anti-steap1 (HC A114C)-maleimide ketal-Ant 113 1/mg/kg | 22.83 | 1.65 | 8/8 | 0 | 0 |
| (5) thio-anti-steap1 (HC A114C)-maleimide ketal-Ant 113 3 mg/kg | 68.49 | 1.65 | 8/8 | 1 | 0 |

TABLE 7-continued in vivo LnCap-Ner xenograft tumor efficacy study (FIG. 32)

| Test compound dose | drug exposure ug/m2 | avg. drug loading | TI - tumor incidence | PR - partial tumor regression | CR - complete tumor regression |
|---|---|---|---|---|---|
| (6) thio-anti-steap1 (HC A114C)-maleimide ketal-Ant 113 6 mg/kg | 137 | 1.65 | 7/7 | 5 | 0 |
| (7) thio-anti-CD22 (HC A114C)-maleimide ketal-Ant 107 1 mg/kg | 24.21 | 1.75 | 6/6 | 0 | 0 |
| (8) thio-anti-CD22 (HC A114C)-maleimide ketal-Ant 107 3 mg/kg | 72.64 | 1.75 | 7/7 | 1 | 0 |
| (9) thio-anti-CD22 (HC A114C)-maleimide ketal-Ant 107 6 mg/kg | 145 | 1.75 | 7/7 | 0 | 0 |

Rodent Toxicity

Antibody-drug conjugates and an ADC-minus control, "Vehicle", may be evaluated in an acute toxicity rat model (Brown et al (2002) Cancer Chemother. Pharmacol. 50:333-340) and according to Example 11. Toxicity of ADC is investigated by treatment of female Sprague-Dawley rats with the ADC and subsequent inspection and analysis of the effects on various organs. Based on gross observations (body weights), clinical pathology parameters (serum chemistry and hematology) and histopathology, the toxicity of ADC may be observed, characterized, and measured.

A multi-day acute toxicity study in adolescent female rats may be conducted by one or more doses of a candidate ADC, a control ADC, free anthracycline derivative compound (PNU-159682) and a control Vehicle (day 0). Body weight is measured periodically. Clinical chemistry, serum enzymes and hematology analysis is also conducted periodically; concluding with complete necropsy with histopathological assessment. Toxicity signals included the clinical observation of weight loss, considering that weight loss, or weight change relative to animals dosed only with Vehicle in animals after dosing with ADC, is a gross and general indicator of systemic or localized toxicity. Hepatotoxicity may be measured by: (i) elevated liver enzymes such as AST (aspartate aminotransferase), ALT (alanine aminotransferase), GGT (g-glutamyl transferase); (ii) increased numbers of mitotic and apoptotic figures; and (iii) hepatocyte necrosis. Hematolymphoid toxicity is observed by depletion of leukocytes, primarily granuloctyes (neutrophils), and/or platelets, and lymphoid organ involvement, i.e. atrophy or apoptotic activity. Toxicity is also noted by gastrointestinal tract lesions such as increased numbers of mitotic and apoptotic figures and degenerative entercolitis.

Administration of Antibody-Drug Conjugate Pharmaceutical Formulations

Therapeutic antibody-drug conjugates (ADC) may be administered by any route appropriate to the condition to be treated. The ADC will typically be administered parenterally, i.e. infusion, subcutaneous, intramuscular, intravenous, intradermal, intrathecal, bolus, intratumor injection or epidural (Shire et al (2004) J. Pharm. Sciences 93(6):1390-1402).

Pharmaceutical formulations of therapeutic antibody-drug conjugates (ADC) are typically prepared for parenteral administration with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers, in the form of a lyophilized formulation or an aqueous solution (Remington's Pharmaceutical Sciences (1980) 16th edition, Osol, A. Ed.).

The ADC may be formulated as pharmaceutical compositions with a pharmaceutically acceptable carrier or diluent. Any appropriate carrier or diluent may be used. Suitable carriers and diluents include physiological saline solution and Ringers dextrose solutions.

Acceptable parenteral vehicles, diluents, carriers, excipients, and stabilizers are nontoxic to recipients at the dosages and concentrations employed, and include: (i) buffers such as phosphate, citrate, dibasic calcium phosphate, magnesium stearate, and other organic acids; (ii) antioxidants including ascorbic acid and methionine; (iii) preservatives (such as octadecyldimethylbenzyl ammonium chloride; hexamethonium chloride; benzalkonium chloride, benzethonium chloride; phenol, butyl or benzyl alcohol; (iv) alkyl parabens such as methyl or propyl paraben; catechol; resorcinol; cyclohexanol; 3-pentanol; and m-cresol); (v) low molecular weight (less than about 10 residues) polypeptides; proteins, such as serum albumin, gelatin, or immunoglobulins; (vi) hydrophilic polymers such as polyvinylpyrrolidone; (vii) amino acids such as glycine, glutamine, asparagine, histidine, arginine, or lysine; (viii) monosaccharides, disaccharides, and other carbohydrates including glucose, lactose, sucrose, mannitol, trehalose, sodium starch glycolate, sorbitol mannose, carboxymethylcellulose, or dextrins; (ix) chelating agents such as EDTA; (x) salt-forming counter-ions such as sodium; metal complexes (e.g. Zn-protein complexes); (xi) non-ionic surfactants such as TWEEN™, PLURONICS™ or polyethylene glycol (PEG); (xii) glidants or granulating agents such as magnesium stearate, carboxymethylcellulose, talc, silica, and hydrogenated vegetable oil; (xiii) disintegrant such as crosprovidone, sodium starch glycolate or cornstarch; (xiv) thickening agents such as gelatin and polyethylene glycol;

(xv) enteric coatings such as triethyl citrate; and/or (xvi) taste or texture modifiers, antifoaming agents, pigments, and dessicants. For example, lyophilized anti-ErbB2 antibody formulations are described in WO 97/04801, expressly incorporated herein by reference. An exemplary formulation of an ADC contains about 100 mg/ml of trehalose (2-(hydroxymethyl)-6-[3,4,5-trihydroxy-6-(hydroxymethyl)tetrahydropyran-2-yl]oxy-tetrahydropyran-3,4,5-triol; $C_{12}H_{22}O_{11}$; CAS Number 99-20-7) and about 0.1% TWEEN™ 20 (polysorbate 20; dodecanoic acid 2-[2-[3,4-bis(2-hydroxyethoxy)tetrahydrofuran-2-yl]-2-(2-hydroxyethoxy)ethoxy]ethyl ester; $C_{26}H_{50}O_{10}$; CAS Number 9005-64-5) at approximately pH 6.

Pharmaceutical formulations of a therapeutic antibody-drug conjugate (ADC) may contain certain amounts of unreacted drug moiety (D), antibody-linker intermediate (Ab-L), and/or drug-linker intermediate (D-L), as a consequence of incomplete purification and separation of excess reagents, impurities, and by-products, in the process of making the ADC; or time/temperature hydrolysis or degradation upon storage of the bulk ADC or formulated ADC composition. For example, a formulation of the ADC may contain a detectable amount of free drug. Alternatively, or in addition to, it may contain a detectable amount of drug-linker intermediate. Alternatively, or in addition to, it may contain a detectable amount of the antibody. The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared under sterile conditions and by uniformly and intimately bringing into association the ADC with liquid carriers or finely divided solid carriers or both, and then, if necessary, shaping the product.

Aqueous suspensions contain the active materials (ADC) in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 μg of the active ingredient per milliliter of solution in order that infusion of a suitable volume at a rate of about 30 mL/hr can occur. Subcutaneous (bolus) administration may be effected with about 1.5 ml or less of total volume and a concentration of about 100 mg ADC per ml. For ADC that require frequent and chronic administration, the subcutaneous route may be employed, such as by pre-filled syringe or autoinjector device technology.

As a general proposition, the initial pharmaceutically effective amount of ADC administered per dose will be in the range of about 0.01-100 mg/kg, namely about 0.1 to 20 mg/kg of patient body weight per day, with the typical initial range of compound used being 0.3 to 15 mg/kg/day. For example, human patients may be initially dosed at about 1.5 mg ADC per kg patient body weight. The dose may be escalated to the maximally tolerated dose (MTD). The dosing schedule may be about every 3 weeks, but according to diagnosed condition or response, the schedule may be more or less frequent. The dose may be further adjusted during the course of treatment to be at or below MTD which can be safely administered for multiple cycles, such as about 4 or more.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are generally disfavored due to poor bioavailability due to limited absorption, hydrolysis or denaturation in the gut, formulations of ADC suitable for oral administration may be prepared as discrete units such as capsules, cachets or tablets each containing a predetermined amount of the ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

Antibody-Drug Conjugate Methods of Treatment

Antibody-drug conjugates of the invention are useful as antitumor agents. A mammal, e.g. a human or animal, may therefore be treated by a method comprising administering thereto a pharmaceutically effective amount of a conjugate of formula I as hereinbefore defined. The condition of the human or animal may be ameliorated or improved in this way.

Formula I ADC may be used to treat various diseases or disorders in a patient, such as cancer and autoimmune conditions including those characterized by the overexpression of a tumor-associated antigen. Exemplary conditions or disorders include benign or malignant tumors; leukemia and lymphoid malignancies; other disorders such as neuronal, glial, astrocytal, hypothalamic, glandular, macrophagal, epithelial, stromal, blastocoelic, inflammatory, angiogenic and immunologic disorders. Cancer types susceptible to ADC treatment include those which are characterized by the overexpression of certain tumor associated antigens or cell surface receptors, e.g. HER2.

One method is for the treatment of cancer in a mammal, wherein the cancer is characterized by the overexpression of an ErbB receptor. The mammal optionally does not respond, or responds poorly, to treatment with an unconjugated anti-ErbB antibody. The method comprises administering to the mammal a therapeutically effective amount of an antibody-drug conjugate compound. The growth of tumor cells that overexpress a growth factor receptor such as HER2 receptor or EGF receptor may be inhibited by administering to a patient a Formula I ADC which binds specifically to said growth factor receptor and a chemotherapeutic agent wherein said antibody-drug conjugate and said chemotherapeutic agent are each administered in amounts effective to inhibit growth of tumor cells in the patient.

A human patient susceptible to or diagnosed with a disorder characterized by overexpression of ErbB2 receptor, may be treated by administering a combination of a Formula I ADC and a chemotherapeutic agent. Such excessive activation may be attributable to overexpression or increased production of the ErbB receptor or an ErbB ligand. In one embodiment, a diagnostic or prognostic assay will be performed to determine whether the patient's cancer is characterized by excessive activation of an ErbB receptor. For example, ErbB gene amplification and/or overexpression of an ErbB receptor in the cancer may be determined. Various assays for determining such amplification/overexpression are available in the art and include IHC, FISH and shed antigen assays.

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The ADC formulation is suitably administered to the patient at one time or over a series of treatments. Depending on the type and severity of the disease, about 1 µg/kg to 15 mg/kg (e.g. 0.1-20 mg/kg) of ADC is an initial candidate dosage for administration to the patient, whether, for example, by one or more separate administrations, or by continuous infusion. A typical dosage regimen might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the ADC. Other dosage regimens may be useful.

Combination Therapy

An antibody-drug conjugate (ADC) may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, aromatase inhibitor, protein kinase inhibitor, lipid kinase inhibitor, anti-androgen, antisense oligonucleotide, ribozyme, gene therapy vaccine, anti-angiogenic agent and/or cardioprotectant. Such molecules are suitably present in combination in amounts that are effective for the purpose intended. A pharmaceutical composition containing an ADC may also have a therapeutically effective amount of a chemotherapeutic agent such as a tubulin-forming inhibitor, a topoisomerase inhibitor, or a DNA binder.

Alternatively, or additionally, the second compound may be an antibody which binds or blocks ligand activation of tumor-associated antigen or receptor. The second antibody may be conjugated with a cytotoxic or chemotherapeutic agent, e.g., a macrocyclic depsipeptide, an auristatin, a calicheamicin, or a 1,8 bis-naphthalimide moiety. For example, it may be desirable to further provide antibodies which bind to EGFR, ErbB2, ErbB3, ErbB4, or vascular endothelial factor (VEGF) in the one formulation or dosing regimen.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

In one embodiment, treatment with an ADC of the present invention involves the combined administration of an anticancer agent identified herein, and one or more chemotherapeutic agents or growth inhibitory agents. Preparation and dosing schedules for such chemotherapeutic agents may be used according to manufacturers's instructions or as determined empirically by the skilled practitioner. Preparation and dosing schedules for such chemotherapy are also described in Chemotherapy Service Ed., M. C. Perry, Williams & Wilkins, Baltimore, Md. (1992).

The ADC may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products may be identified by preparing a radiolabelled (e.g. $^{14}C$ or $^{3}H$) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds.

Metabolites include the products of in vivo cleavage of the ADC where cleavage of any bond occurs that links the drug moiety to the antibody. Metabolic cleavage may thus result in the naked antibody, or an antibody fragment. The antibody metabolite may be linked to a part, or all, of the linker. Metabolic cleavage may also result in the production a drug moiety or part thereof. The drug moiety metabolite may be linked to a part, or all, of the linker.

Articles of Manufacture

In another embodiment, an article of manufacture, or "kit", containing ADC and materials useful for the treatment of the disorders described above is provided. The article of manufacture comprises a container and a label or package insert on or associated with the container. Suitable containers include, for example, bottles, vials, syringes, or blister pack. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer.

In one embodiment, the article of manufacture may further comprise a second (or third) container comprising a pharmaceutically-acceptable buffer, such as bacteriostatic water for injection (BWFI), phosphate-buffered saline, Ringer's solution and dextrose solution, and a package insert indicating that the first and second compounds can be used to treat cancer. It may further include other materials desirable from a commercial and user standpoint, including other buffers, diluents, filters, needles, and syringes.

EXAMPLES

The compounds of the present invention, as prepared according to the following examples, were characterized by HPLC/MS analytical data; HPLC/MS data were collected following any one of methods 1, 2.

HPLC/MS Analytic Method 1

Waters 2795 Alliance HT HPLC system equipped with a 2996 Waters PDA detector and Micromass mod. ZQ single quadruple mass spectrometer, equipped with an electrospray (ESI) ion source. Instrument control, data acquisition and data processing were provided by Empower and MassLynx 4.0 software. HPLC was carried out at 30° C. at a flow rate of 1.0 mL/min using a C18, 3 micron Phenomenex (4.6×50 mm) column. Mobile phase A was ammonium acetate 5 mM pH 5.2 buffer with acetonitrile (95:5), and mobile phase B was H$_2$O/acetonitrile (5:95); the gradient was from 10 to 90% B in 8 minutes then ramp to 100% B in 1.0 minutes. The injection volume was 10 uL. The mass spectrometer was operated in positive and in negative ion mode, the capillary voltage was set up at 3.5 KV (ES$^+$) and 28 V (ES); the source temperature was 120° C.; cone was 14 V (ES$^+$) and 2.8 KV (ES); full scan, mass range from 100 to 1000 m/z.

HPLC/MS Analytic Method 2

Waters 2795 HPLC system was equipped with a 996 Waters PDA detector and Micromass mod. ZQ single quadruple mass spectrometer, equipped with an electrospray (ESI) ion source. Instrument control, data acquisition and data processing were provided by Empower and MassLynx 4.0 software. HPLC was carried out at 30° C. at a flow rate of 1 mL/min using a RP18 Waters X Terra (4.6 μM×50 mm) column. Mobile phase A was ammonium hydroxide 0.05% pH=10 buffer with acetonitrile (95:5), and Mobile phase B was H$_2$O/acetonitrile (5:95); the gradient was from 10 to 90% B in 8 minutes then hold 100% B for 2 minutes. The injection volume was 10 μL. The mass spectrometer was operated in positive and in negative ion mode, the capillary voltage was set up at 2.5 KV; the source temperature was 120° C.; cone was 10 V; full scan, mass range from 100 to 1000 m/z.

Example 1

N-methyl-2-[(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}cyclohexyl)oxy]acetamide (Compound 2)

Step 1 Synthesis of the intermediate ethyl [(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}cyclohexyl)oxy]acetate 45

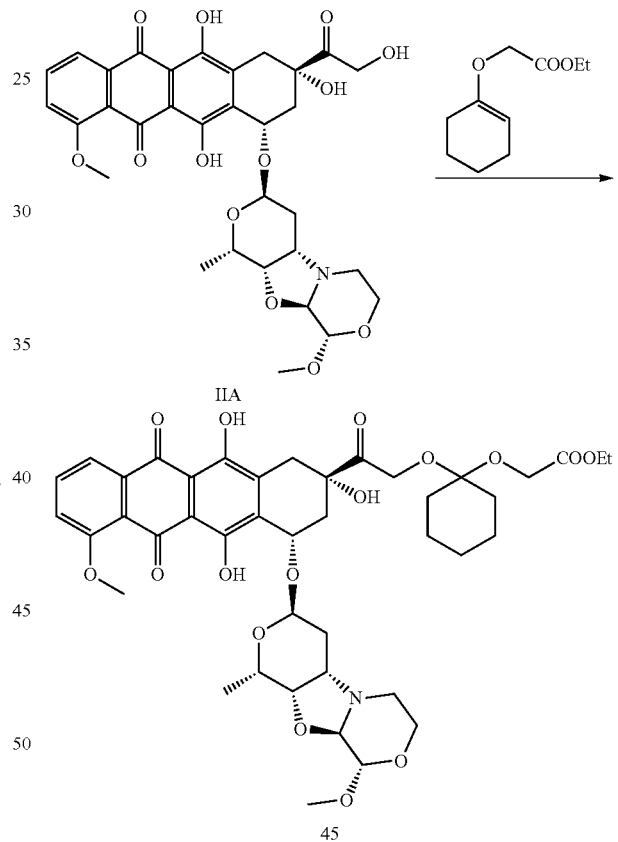

To a solution of (8S,10S)-6,8,11-trihydroxy-8-(hydroxyacetyl)-1-methoxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione (50 mg, 0.078 mmol) [PNU-159682, compound IIA, prepared as reported in WO 9802446] in 2 ml of dry dimethylformamide kept under argon, (Cyclohex-1-enyloxy)-acetic acid ethyl ester (0.5 mL, [prepared as reported in J. Org. Chem. (1978) 43:1244-1245] and p-toluenesulfonic acid monohydrate (5 mg, 0.026 mmol) were added. The reaction mixture was stirred overnight at room temperature, sodium bicarbonate saturated solution was added (20 mL)

and the product extracted with dichloromethane (2×20 mL). The combined organic phases were dried over anhydrous sodium sulfate, filtered, the solvent removed under vacuum and the residue partially purified by flash chromatography (DCM/MeOH 97.5:2.5) to give 30 mg (37%) of the ester intermediate that was used as such in step 2. MS (ESI): 826 [M+H]+. Retention time=7.48 min. method 2

Step 2 Synthesis of the intermediate [(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}cyclohexyl)oxy] acetic acid 46

46

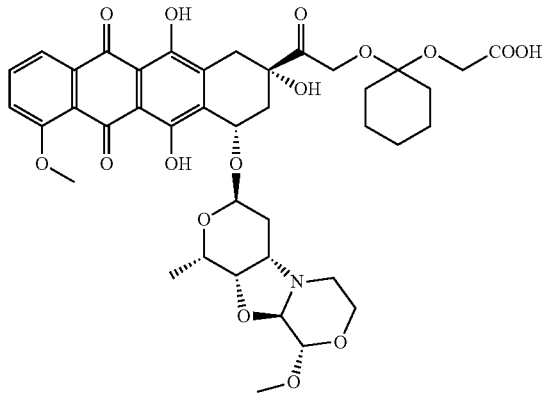

To 30 mg of 45, 5 mL of in 01N NaOH was added. The suspension was cooled at 5° C. and stirred under argon for 3 hours. The aqueous solution was brought to pH≅8 with 10% acetic acid water solution and extracted with dichloromethane (2×10 mL). The combined organic phases were dried over anhydrous sodium sulfate, filtered, the solvent removed under vacuum and the residue purified by flash chromatography (DCM/MeOH 90:10) to give 5 mg (y=8% 2 steps) of the acid intermediate 46 as a red solid. MS (ESI): 798 [M+H]+. Retention time=3.94 min. Method 2

Step 3 Synthesis of intermediate 1-({[(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5] [1,3]oxazolo[2,3-c][1,4]oxazin-3-yl]oxy}-6,11-dioxo-1,2,3,4,6,11-hexahydrotetracen-2-yl]ethoxy}cyclohexyl)oxy] acetyl}oxy)pyrrolidine-2,5-dione 47

47

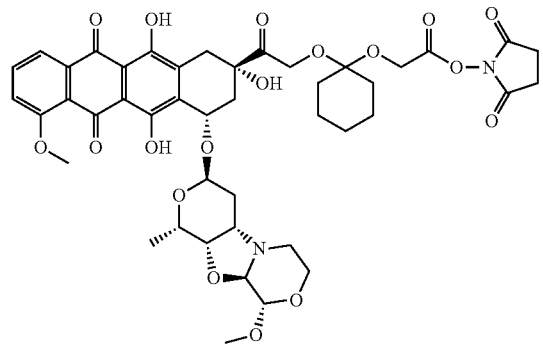

To a solution of the acid intermediate 46 (4 mg, 0.005 mmol) in dry Dichloromethane (2 mL) kept at +5° C., N-hydroxysuccinimide (2 mg, 0.017 mmol) and N,N'-dicyclohexylcarbodiimide (2 mg, 0.01 mmol) were added. The solution was stirred at room temperature for 6 h, the solvent evaporated under vacuum and the residue treated with ethyl ether (5 mL). The suspension was stirred for 30 minutes, the solid removed by filtration and organic solution concentrated in vacuo. Purification of the crude by flash chromatography (DCM/Acetone 80:20) yield 1.5 mg (y=33%) of 47 as a red solid. MS (ESI): 895 [M+H]+. Retention time=3.22 min. Method 1.

Step 4 Synthesis of the Title Compound 2

2

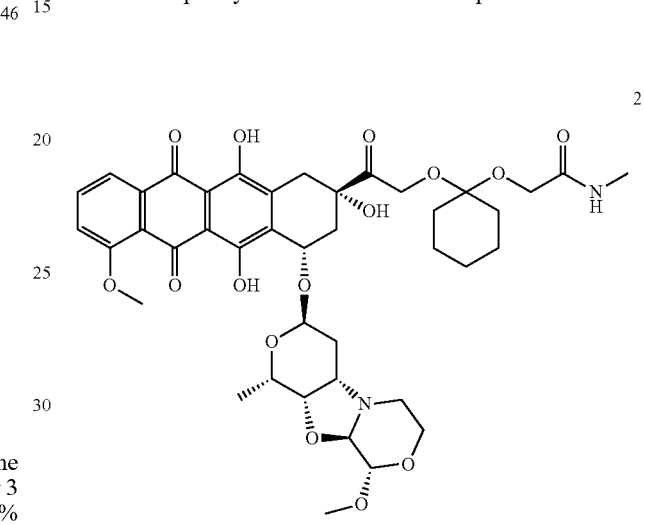

To a solution of 47 obtained from step 3 (1 mg, 0.001 mmol) in dry tetrahydrofuran (2 mL), 1 M methylamine in THF (3 μL, 0.003 mmol) were added. The solution was stirred at room temperature 30 minutes, the solvent evaporated under vacuum and the residue purified by flash chromatography (dichloromethane/methanol 90:10) yield 0.9 mg (y=99%) of 2 as a red solid. MS (ESI): 811 [M+H] Retention time=6.10 min. Method 2, Retention time=5.99 min. Method 1.

By analogous procedure and using the suitable starting materials the following compounds were prepared:

2-[(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5] [1,3]oxazolo[2,3-c][1,4]oxazin-3-yl]oxy}-6,11-dioxo-1,2,3,4,6,11-hexahydrotetracen-2-yl]ethoxy}cyclohexyl)oxy]acetamide (Compound 1) MS (ESI): 887 [M+H] Retention time=5.86 min. Method 2

N-benzyl-2-[(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4, 5][1,3]oxazolo[2,3-c][1,4]oxazin-3-yl]oxy}-6,11-dioxo-1,2,3,4,6,11-hexahydrotetracen-2-yl]ethoxy}cyclohexyl)oxy]acetamide (Compound 3) MS (ESI): 797 [M+H] Retention time=7.16 min. Method 2

$N^2$-(tert-butoxycarbonyl)-$N^6$-{[(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}cyclohexyl)oxy]acetyl}-L-lysine (Compound 4) MS (ESI): 1026 [M+H]+. Retention time=5.26 min. Method 1; Retention time=4.64 min. Method 2

Example 2

N-methyl-2-[(6-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}tetrahydro-2H-pyran-2-yl)methoxy]acetamide (Compound 7)

Step 1 Synthesis of the intermediate: ethyl (3,4-dihydro-2H-pyran-2-ylmethoxy)acetate

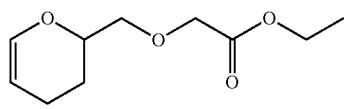

In a dried round bottomed flask under argon atmosphere, 60% sodium hydride (240 mg, 6.0 mmol) was rinsed three times with anhydrous n-pentane. A solution of 2-hydroxymethyl-3,4-dihydro-2H-pyran (570.8 mg, 5 mmol) in tetrahydrofuran (10 ml) was cooled at 0° C. and then added to the NaH. The reaction mixture was stirred at 0° C. until hydrogen evolution ended. A solution of ethyl bromoacetate (1253 mg, 7.5 mmol) in tetrahydrofuran (6 ml) was added to the reaction mixture and the stirring was continued at room temperature until disappearance of the starting alcohol (TLC analysis). After cooling, H₂O was added, and the solvent was evaporated under reduced pressure. The residue was purified by flash column chromatography (AcOEt:hexane=1:12) on silica gel (230-400 mesh), affording 626 mg (yield 57%) of ethyl (3,4-dihydro-2H-pyran-2-ylmethoxy)acetate as a colorless oil; $^1$H NMR (401 MHz, DMSO-$d_6$) δ ppm 1.18-1.23 (m, 3H) 3.55-3.59 (m, 2H) 3.93 (m, J=10.08, 5.11, 5.11, 2.38 Hz, 1H) 4.13 (q, J=7.07 Hz, 2H) 4.14 (s, 2H) 4.67 (dddd, J=6.14, 4.83, 2.56, 1.34 Hz, 1H) 6.36 (dt, J=6.13, 1.75 Hz, 1H).

Step 2 Synthesis of the intermediate: ethyl [(6-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}tetrahydro-2H-pyran-2-yl)methoxy]acetate 48

To a solution of (8S,10S)-6,8,11-trihydroxy-8-(hydroxyacetyl)-1-methoxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione (50 mg, 0.078 mmol) [PNU-159682, formula IIA, prepared as reported in WO 9802446] in 4 ml of dry dichloromethane under argon atmosphere, ethyl (3,4-dihydro-2H-pyran-2-ylmethoxy)acetate from step 1 (118.5 mg, 0.592 mmol) and anhydrous p-toluenesulfonic acid (22.3 mg, 0.12 mmol) were added. The reaction mixture was stirred at room temperature for 4 hours, until no starting material was detectable (TLC analysis, MeOH:CH₂Cl₂=0.3:9.7). Sodium bicarbonate 10% aqueous solution was then added to the reaction mixture and the aqueous phase was extracted with dichloromethane (4×20 ml).The combined organic phases were dried over anhydrous sodium sulfate, filtered and evaporated under vacuum. The residue was purified by flash column chromatography (MeOH:CH₂Cl₂=0.3:9.7) on silica gel (230-400 mesh), affording 41 mg (red wax, yield 62%) of 48, as a mixture of four diastereoisomers. MS (ESI): 842 [M+H]⁺. Retention time=7.47, 7.83 min (method 2).

Step 3 Synthesis of the intermediate: [(6-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}tetrahydro-2H-pyran-2-yl)methoxy]acetic acid 49

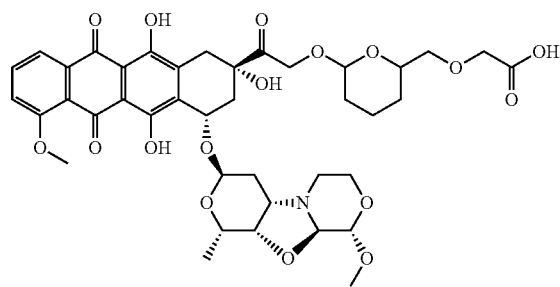

49

The ethyl ester intermediate 48 obtained from step 2 (40 mg, 0.0475 mmol) cooled at 0° C., was treated with aqueous

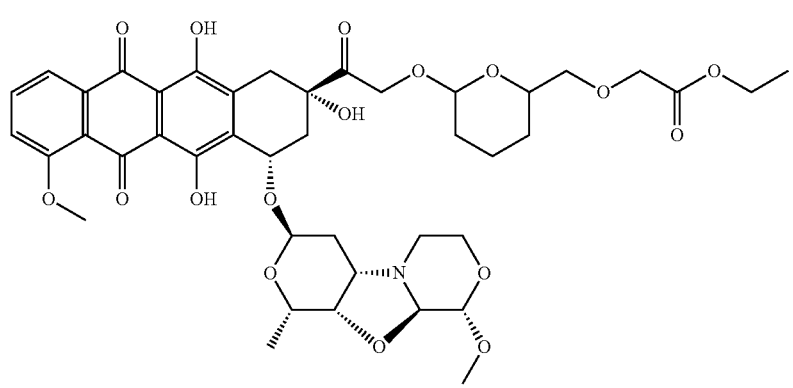

48

0.1 N sodium hydroxide (1.5 ml) under argon. The reaction mixture was stirred at 0° C. for 2 hours. The course of the reaction was followed by reverse-phase HPLC-MS. After that, the reaction mixture was brought to pH≅ 8 with 10% acetic acid water solution, and extracted with n-butanol saturated with water (8×10 mL). The combined organic phases were dried over anhydrous sodium sulfate, filtered, and the solvent removed under vacuum. The residue was purified by flash column chromatography (MeOH:CH$_2$Cl$_2$=1:9) on silica gel (230-400 mesh), affording 4.5 mg (red solid, yield 12%) of 49 as a diasteroisomeric mixture. MS (ESI): 814 [M+H]$^+$. Retention time=2.99, 3.50, 3.66 (method 2). Retention time=4.24 (method 1).

Step 4 Synthesis of the intermediate: 1-({[(6-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}tetrahydro-2H-pyran-2-yl)methoxy]acetyl}oxy)pyrrolidine-2,5-dione 50 starting material was detectable (HPLC-MS analysis), and the solvent evaporated under vacuum. The residue was purified by flash column chromatography (MeOH: CH$_2$Cl$_2$=0.3: 9.7) on silica gel (230-400 mesh), affording 0.46 mg (red solid, yield 51%) of 7 as a mixture of diastereoisomers. MS (ESI): 827 [M+H]$^+$. Retention time=5.34, 5.54, 5.66 min (method 1).

By analogous procedures and using the suitable starting materials the following compounds were prepared:

2-[(6-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}tetrahydro-2H-pyran-2-yl)methoxy]acetamide (Compound 6) MS (ESI): 813 [M+H]$^+$. Retention time=5.42 min (method 2).

N-benzyl-2-[(6-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}tetrahydro-2H-pyran-2-yl)methoxy]acetamide (Compound 8) MS (ESI): 903 [M+H]$^+$. Retention time=6.92 min (method 1). Retention time=6.94 min (method 2).

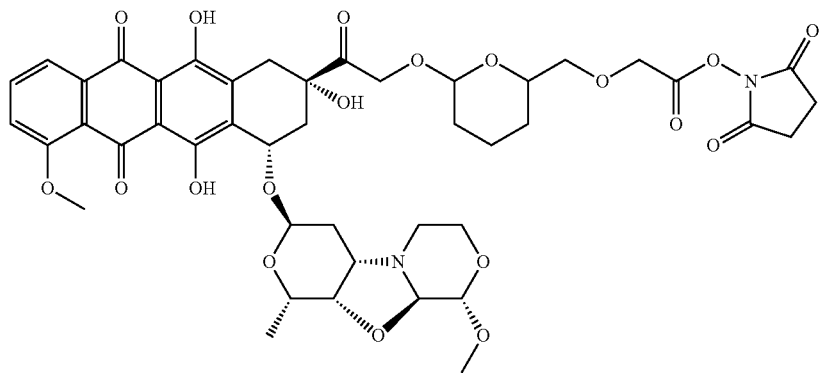

50

To a solution of the acid intermediate 49 obtained from step 3 of the process (2 mg, 0.0024 mmol) in dry dichloromethane (1 ml) cooled at 0° C., N-hydroxysuccinimide (1 mg, 0.00792 mmol) and N,N'-dicyclohexylcarbodiimide (1 mg, 0.004556 mmol) were added. The reaction mixture was stirred at 0° C. for 2.5 h, until disappearance of the starting material (HPLC-MS analysis). The solvent evaporated under vacuum and the residue treated with ethyl ether (2×4 ml). The suspension was stirred for 10 minutes, the solid removed by filtration and the organic solution concentrated in vacuo, affording 2 mg of 50 (red solid) as a mixture of diastereoisomers. MS (ESI): 911 [M+H]$^+$. Retention time=6.12, 6.30, 6.42 min (method 1).

Step 5 The Title Compound 7

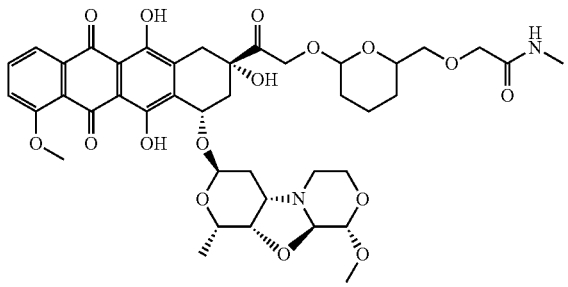

7

To a solution of 50 obtained from step 4 of the process (1 mg, 0.0011 mmol) in dry dichloromethane (100 μL), 2.0 M methylamine in THF (65 μL, 0.0033 mmol) were added. The solution was stirred at room temperature 4 hours until no Example 3

N-acetyl-3-({3-[(2E)-2-{2-hydroxy-1-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethylidene}hydrazinyl]-3-oxopropyl}disulfanyl)-L-alanine (Compound 12)

Step 1 N'-{(1E)-2-hydroxy-1-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethylidene}-3-(pyridin-2-yldisulfanyl)propanehydrazide 53

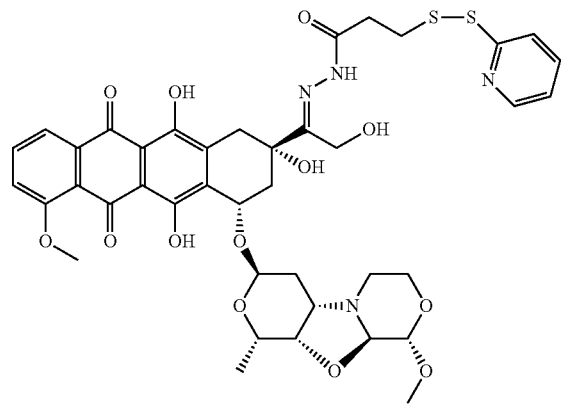

53

A solution of 3-(2-pyridyldithio)propionic acid hydrazide HCl (41.5 mg, 0.156 mmol) in anhydrous methanol (5 ml) was added to (8S,10S)-6,8,11-trihydroxy-8-(hydroxyacetyl)-1-methoxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione [PNU-159682, compound IIA, prepared as reported in WO 9802446] (50 mg, 0.078 mmol). The solution was stirred in the dark at room temperature for 20 hours. The course of the reaction was followed by reverse-phase HPLC-MS. After this period the solvent was evaporated and the residue was purified by flash column chromatography (MeOH:CH$_2$Cl$_2$=0.2:9.8) on silica gel (230-400 mesh), affording 18 mg (yield 27%) of 53. MS (ESI): 853 [M+H]$^+$. Retention time=5.52 min (method 2).

By analogous procedures and using the suitable starting materials the following compound was prepared: 6-(2,5-dioxo-2,5-dihydro-1H-pyrrol-1-yl)-N'-{(1E)-2-hydroxy-1-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethylidene}hexanehydrazide 52. MS (ESI): 849 [M+H]$^+$. Retention time=5.15 min (method 2).

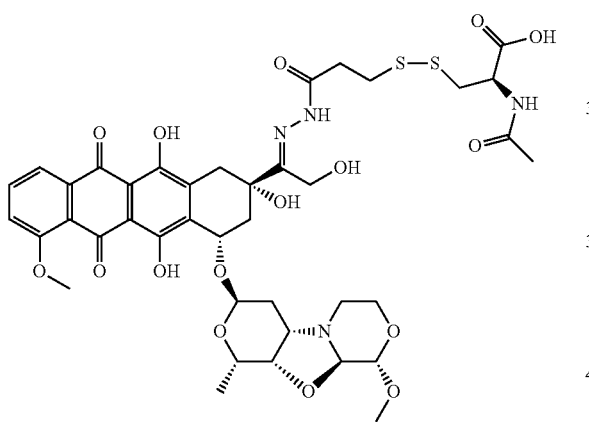

12

Step 2

To a solution of 53 obtained from step 1 (8.5 mg, 0.01 mmol.) N-acetylcysteine was added (0.32 mg, 0.02 mmol). The solution was stirred at room temperature for 24 hours, the solvent was evaporated and the residue was purified by flash column chromatography (MeOH:CH$_2$Cl$_2$=2:8) on silica gel (230-400 mesh), affording 7.2 mg (yield 80%) of 12 as a red solid. MS (ESI): 905 [M+H]$^+$. Retention time=3.62 min (method 2).

By analogous procedures and using the suitable starting materials the following compounds were prepared:

N-acetyl-S-(1-{6-[(2E)-2-{2-hydroxy-1-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethylidene}hydrazinyl]-6-oxohexyl}-2,5-dioxopyrrolidin-3-yl)-L-cysteine (Compound 9). MS (ESI): 1012 [M+H]$^+$.

N$^2$-(tert-butoxycarbonyl)-N$^6$-(1-{6-[(2E)-2-{2-hydroxy-1-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethylidene}hydrazinyl]-6-oxohexyl}-2,5-dioxopyrrolidin-3-yl)-L-lysine (Compound 10, Table 1) MS (ESI): 1095 [M+H]$^+$.

Example 3a

Preparation of (2S,4S)—N-[2-(2,5-dioxo-2,5-dihydro-1H-pyrrol-1-yl)ethyl]-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracene-2-carboxamide 54

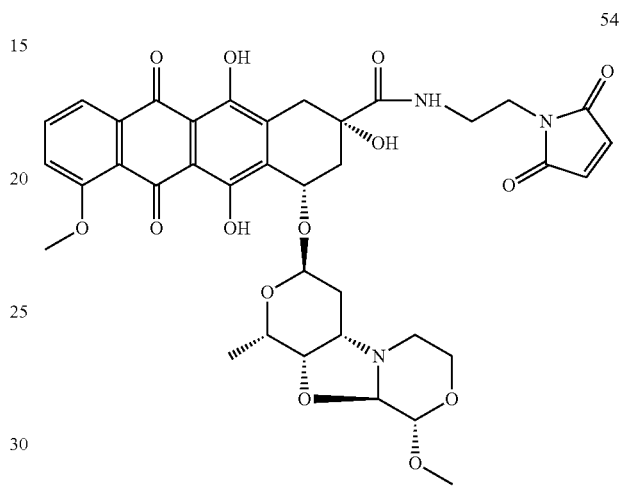

54

To a solution of PNU-159682 (15.3 mg, 0.02038 mmol) prepared as reported in WO 98/02446, in 3 ml of methanol and 2 ml of H$_2$O, a solution of NaIO$_4$ (5.1 mg, 0.0238 mmol) in 1 ml of H$_2$O was added. The reaction mixture was stirred at room temperature for 3 hours, until no starting material was detectable (TLC and HPLC analysis). The solvents were removed under reduced pressure and the crude red solid (2S, 4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracene-2-carboxylic acid 56 was used without further purifications in the next step. MS (ESI): 628 [M+H]$^+$. Retention time=2.1-3.2 min (method 1, Example 3b).

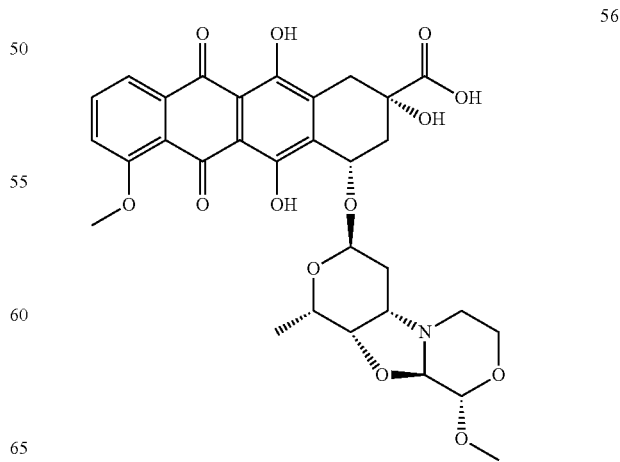

56

To a solution of the crude intermediate 56 (4.4 mg) in anhydrous dichloromethane (1.5 ml) under argon atmosphere, anhydrous triethylamine (2.2 mg, 0.0204 mmol), TBTU (4.4 mg, 0.01388 mmol) and commercially available N-(2-aminoethyl)maleimide trifluoroacetate salt (3.6 mg, 0.00694 mmol) were added. The reaction mixture was stirred at room temperature for 30 min, until disappearance of the starting material (HPLC-MS analysis). The solvent was evaporated under vacuum and the residue was then purified by flash column chromatography (EtOH:CH$_2$Cl$_2$=0.2:9.8) on silica gel (230-400 mesh), affording 1.1 mg (red solid, yield calculated on PNU-159682=21%) of 54. MS (ESI): 750 [M+H]$^+$. Retention time=5.18 min (method 1, Example 3b).

Example 3b

Preparation of N-[6-(2,5-dioxo-2,5-dihydro-1H-pyrrol-1-yl)hexanoyl]-L-valyl-N$^5$-carbamoyl-N-[4-({[(4-{[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]carbonyl}piperazin-1-yl)carbonyl]oxy}methyl)phenyl]-L-ornithinamide 55

Step 1 4-((S)-2-((S)-2-(6-(2,5-Dioxo-2,5-dihydro-1H-pyrrol-1-yl)hexanamido)-3-methylbutanamido)-5-ureidopentanamido)benzyl 4-nitrophenyl carbonate 58 (30 mg, 0.041 mmol) was reacted with tert-butyl piperazine-1-carboxylate (5.3 mg, 0.0287 mmol) in anhydrous DMSO under argon atmosphere at room temperature (FIG. 7d). The reaction mixture was stirred for 1 h, until disappearance of the starting material (HPLC-MS analysis). Diethyl ether (80 ml) was then added to the reaction mixture and the precipitate thus obtained was collected by filtration to give N-[6-(2,5-dioxo-2,5-dihydro-1H-pyrrol-1-yl)hexanoyl]-L-valyl-N-{4-[({[4-(tert-butoxycarbonyl)piperazin-1-yl]carbonyl}oxy)methyl]phenyl}-N$^5$-carbamoyl-L-ornithinamide 59 as a yellow solid, 22.0 mg) was isolated and used without further purification in the next step. MS (ESI): 785 [M+H]$^+$. Retention time=4.87 min (method 1).

Step 2 The intermediate 59 (22.0 mg) was treated with trifluoroacetic acid (327 mg, 2.87 mmol) in anhydrous dichloromethane (0.12 ml). The reaction mixture was stirred at room temperature for 15 minutes, until disappearance of the starting material (HPLC-MS analysis). After that, the reaction mixture was treated with diethyl ether (20 ml) and the residue thus obtained was rinsed with diethyl ether (2×10 ml): the product N-[6-(2,5-dioxo-2,5-dihydro-1H-pyrrol-1-yl)hexanoyl]-L-valyl-N$^5$-carbamoyl-N-(4-{[(piperazin-1-ylcarbonyl)oxy]methyl}phenyl)-L-ornithinamide 60 (white wax, 20.0 mg) was thus isolated and used without further purification in the next step. MS (ESI): 685 [M+H]$^+$. Retention time=2.97 min (method 1).

Step 3 To the intermediate 60 (13.2 mg) a solution of crude (2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracene-2-carboxylic acid 56 (9.3 mg) in anhydrous dichloromethane (2.6 ml), TBTU (5.3 mg, 0.0165 mmol), and anhydrous triethylamine (2.8 mg, 0.0275 mg) was added. The reaction mixture was stirred at room temperature under argon atmosphere for 15 minutes, until disappearance of the starting material (HPLC-MS analysis). The solvent was then evaporated under vacuum and the crude was purified by flash column chromatography (EtOH:AcOEt=1.5:8.5) on silica gel (230-400 mesh), affording 4.8 mg (red solid, yield calculated on PNU-159682=34%) of 55. MS (ESI): 1295 [M+H]$^+$. Retention time=5.51 min(method 1).

55

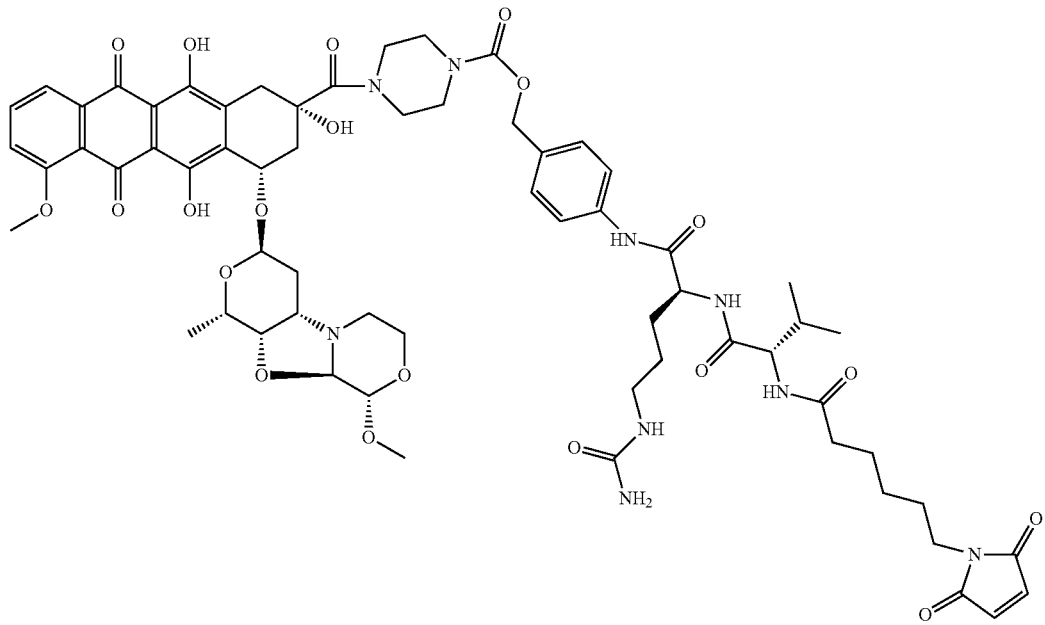

Compounds were characterized by HPLC/MS analytical data; HPLC/MS data were collected following any one of the following Methods 1 or 2.

HPLC/MS Analytic Method 1: The HPLC equipment consisted of a Waters 2795 Alliance HT system equipped with a 2996 Waters PDA detector and Micromass mod. ZQ single quadrupole mass spectrometer, equipped with an electrospray (ESI) ion source. Instrument control, data acquisition and data processing were providen by Empower and MassLynx 4.0 software. HPLC was carried out at 30° C. at a flow rate of 1.0 mL/min using a Waters X Terra MS C18-3.5 nM (4.6×50 mm) column. Mobile phase A was ammonium acetate 5 mM pH=5.2 buffer with acetonitrile (95:5), and mobile phase B was H$_2$O/acetonitrile (5:95); the gradient was from 10 to 90% B in 8 minutes then ramp to 100% B in 1.0 minutes. The mass spectrometer was operated in positive and in negative ion mode, the capillary voltage was set up at 3.5 kV (ES$^+$) and 28 V (ES$^-$); the source temperature was 120°

C.; cone was 14 V (ES+) and 2.8 kV (ES−); full scan, mass range from 100 to 1000 m/z was set up.

HPLC/MS Analytic Method 2: The HPLC equipment consisted of a Waters 2795 HPLC system equipped with a 996 Waters PDA detector and Micromass mod. ZQ single quadrupole mass spectrometer, equipped with an electrospray (ESI) ion source. Instrument control, data acquisition and data processing were provided by Empower and MassLynx 4.0 software. HPLC was carried out at 30° C. at a flow rate of 1 mL/min using a RP18 Waters X Terra (4.6 µM×50 mm) column. Mobile phase A was ammonium hydroxide 0.05% pH=10 buffer with acetonitrile (95:5), and Mobile phase B was $H_2O$/acetonitrile (5:95); the gradient was from 10 to 90% B in 8 minutes then hold 100% B for 2 minutes. The mass spectrometer was operated in positive and in negative ion mode, the capillary voltage was set up at 2.5 kV; the source temperature was 120° C.; cone was 10 V; full scan, mass range from 100 to 1000 m/z was set up.

Example 3c

Preparation of (8S,10S)-6,8,11-trihydroxy-1-methoxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-8-(piperazin-1-ylcarbonyl)-7,8,9,10-tetrahydrotetracene-5,12-dione 57

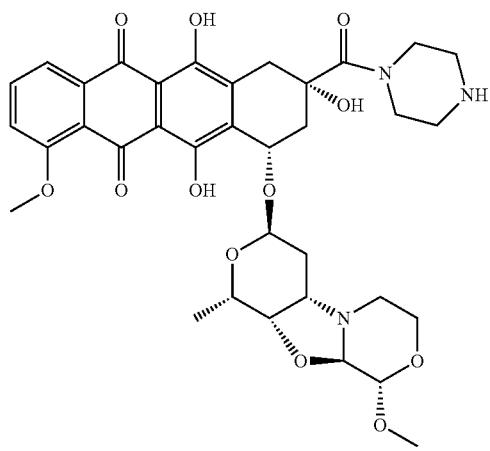

57

To a solution of the crude intermediate 50 (103.8 mg) in anhydrous dichloromethane (29.7 ml) under argon atmosphere, the commercially available N-(2-aminoethyl)maleimide trifluoroacetate salt (57.9 mg, 0.228 mmol) and anhydrous triethylamine (23.1 mg, 0.228 mmol) were added. The reaction mixture was stirred at room temperature for 1 h, until disappearance of the starting material (HPLC-MS analysis). The solvent was evaporated under vacuum and the residue rinsed with a mixture of $Et_2O$/n-hexane (1 ml/20 ml). The crude was then purified by flash column chromatography (EtOH:$CH_2Cl_2$=0.2:9.8) on silica gel (230-400 mesh), affording 12.2 mg (red solid, yield calculated on PNU-159682=20%) of 51 as a diasteroisomeric mixture. MS (ESI): 936 [M+H]+. Retention time=5.86, according to the following method:

Waters 2795 Alliance HT HPLC system with a 2996 Waters PDA detector and Micromass mod. ZQ single quadrupole mass spectrometer, with an electrospray (ESI) ion source. Instrument control, data acquisition and data processing by Empower and MassLynx 4.0 software. HPLC was carried out at 30° C. at a flow rate of 1.0 mL/min using a Waters X Terra MS C18-3.5 µM (4.6×50 mm) column. Mobile phase A was ammonium acetate 5 mM pH=5.2 buffer with acetonitrile (95:5), and mobile phase B was $H_2O$/acetonitrile (5:95); the gradient was from 10 to 90% B in 8 minutes then ramp to 100% B in 1.0 minutes. The mass spectrometer was operated in positive and in negative ion mode, the capillary voltage was set up at 3.5 kV (ES+) and 28 V (ES); the source temperature was 120° C.; cone was 14 V (ES+) and 2.8 kV (ES); full scan, mass range from 100 to 1000 m/z.

Example 3d

Preparation of N-[2-(2,5-dioxo-2,5-dihydro-1H-pyrrol-1-yl)ethyl]-2-[(6-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6-methylidene-11-oxo-1,2,3,4,6,11-hexahydrotetracen-2-yl]ethoxy}tetrahydro-2H-pyran-2-yl)methoxy]acetamide 51

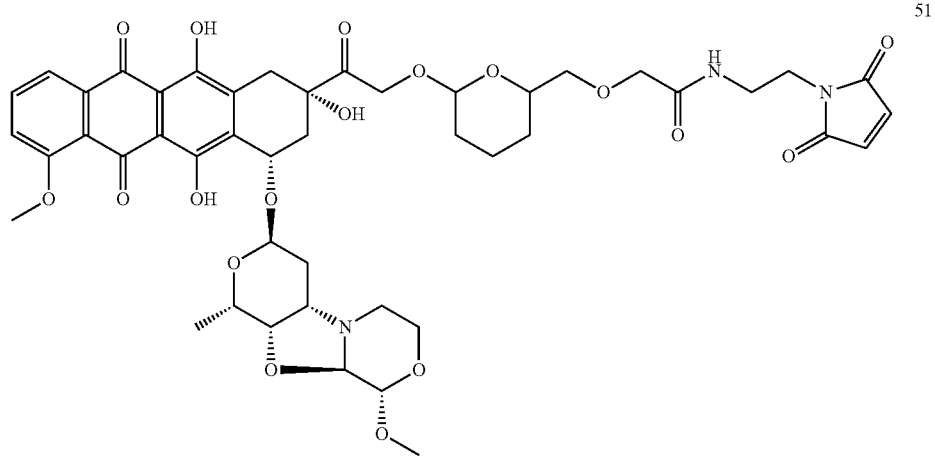 [SMILES: COc1cccc2c1C(=O)c1c(O)c3c(c(O)c1C2=O)C[C@@](O)(C(=O)COC1CCCC(COCC(=O)NCCN2C(=O)C=CC2=O)O1)C[C@@H]3O[C@H]1C[C@H]2[C@H](O[C@@H]3[C@@H](OC)OCCN32)[C@H](C)O1]

51

Example 4

Preparation of the MCM2 conjugate Compound 5, as identified in Table 1

MCM2 (10-294) protein [Ishimi et al (2001) Jour. Biol. Chem. 276(46):42744-42752] (1.5 mg, 0.045 mmol) was dissolved in 0.5 ml of phosphate buffered saline solution (pH 7.2), pH value was adjusted to 8.5 by addition of 55 µl of 1M NaHCO$_3$ (pH 8.5) and 0.5 mg of 1-({[(1-{2-oxo-2-[(2S,4S)-2,5,12-trihydroxy-7-methoxy-4-{[(1S,3R,4aS,9S,9aR,10aS)-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}cyclohexyl)oxy]acetyl}oxy)pyrrolidine-2,5-dione (0.55 µmol) [prepared as reported in example 1 step 3] was added from a 10 mg/ml acetonitrile solution. The reaction was incubated for 1 hr at room temperature then the reaction mixture was desalted on a NAP-10 column conditioned in phosphate buffered saline solution and the fractions containing the protein were collected and pooled.

The reacted protein was analyzed by SDS PAGE in comparison with unreacted MCM2 and different amount of 1-({[(1-{2-oxo-2-[(2S,4S)-2,5,12-trihydroxy-7-methoxy-4-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-6,11-dioxo-1,2,3,4,6,11-hexahydrotetracen-2-yl]ethoxy}cyclohexyl)oxy]acetyl}oxy)pyrrolidine-2,5-dione as reported above.

By analogous procedures and using the suitable starting materials the following compounds (Table 1) were prepared: MCM2 conjugate Compound 11; MCM2 conjugate Compound 13; MCM2 conjugate Compound 14.

Example 5

Stability of the Conjugate: General Procedure

To 0.5 mg of conjugate, ammonium acetate 5 mM pH=5.2 buffer solution (200 mL) was added. The solution was warmed at 37° C. and sample was taken periodically and analyzed by HPLC (method 2). Results are expressed as % of released material (8S,10S)-6,8,11-trihydroxy-8-(hydroxyacetyl)-1-methoxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione (Compound IIA) from the conjugate.

By analogous procedures, using the ammonium acetate 5 mM pH=4.5 buffer solution, the stability at pH 4.5 was also determined.

By analogous procedures, stability was performed on Compound 12 (Table 1), showing, after four hours incubation, 90% release in pH 5.2 buffer solution and 100% release in pH 4.2 buffer solution, of (8S,10S)-6,8,11-trihydroxy-8-(hydroxyacetyl)-1-methoxy-10-{[(1S,3R,4aS,9S,9aR,10aS)-9-methoxy-1-methyloctahydro-1H-pyrano[4',3':4,5][1,3]oxazolo[2,3-c][1,4]oxazin-3-yl]oxy}-7,8,9,10-tetrahydrotetracene-5,12-dione (Compound IIA) from the conjugate.

Example 6

Preparation of Cysteine Engineered Antibodies for Conjugation by Reduction and Reoxidation Light chain and heavy chain amino acids are numbered according to Kabat (Kabat et al., *Sequences of proteins of immunological interest*, (1991) 5th Ed., US Dept of Health and Human Service, National Institutes of Health, Bethesda, Md.). Single letter amino acid abbreviations are used.

Full length, cysteine engineered monoclonal antibodies (ThioMabs) expressed in CHO cells bear cysteine adducts (cystines) or glutathionylated on the engineered cysteines due to cell culture conditions. To liberate the reactive thiol groups of the engineered cysteines, the ThioMabs are dissolved in 500 mM sodium borate and 500 mM sodium chloride at about pH 8.0 and reduced with about a 50-100 fold excess of 1 mM TCEP (tris(2-carboxyethyl)phosphine hydrochloride; Getz et al (1999) Anal. Biochem. 273:73-80; Soltec Ventures, Beverly, Mass.) for about 1-2 hrs at 37° C. Alternatively, DTT can be used as reducing agent. The formation of interchain disulfide bonds was monitored either by non-reducing SDS-PAGE or by denaturing reverse phase HPLC PLRP column chromatography. The reduced cysteine engineered antibody is diluted and loaded onto a HiTrap S column in 10 mM sodium acetate, pH 5, and eluted with PBS containing 0.3M sodium chloride. The eluted reduced cysteine engineered antibody (ThioMab) is treated with 2 mM dehydroascorbic acid (dhAA) at pH 7 for 3 hours, or 2 mM aqueous copper sulfate (CuSO$_4$) at room temperature overnight. Ambient air oxidation may also be effective. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Liquid chromatography/Mass Spectrometric Analysis was performed on a TSQ Quantum Triple quadrupole mass spectrometer with extended mass range (Thermo Electron, San Jose Calif.). Samples were chromatographed on a PRLP-S, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluant was directly ionized using the electrospray source. Data were collected by the Xcalibur data system and deconvolution was performed using ProMass (Novatia, LLC, New Jersey). Prior to LC/MS analysis, antibodies or antibody-drug conjugates (50 µg) are treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 µm, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody.

Example 7

Conjugation of Antibodies and Anthracycline Derivative Drug-Linker Intermediates Generally, antibodies and anthracycline derivative drug-linker intermediates are conjugated according to the methods of U.S. Pat. No. 7,521,541; U.S. Pat. No. 7,498,298; US 2005/0276812; US 2008/0311134; and "NEMORUBICIN METABOLITE AND ANALOG ANTIBODY-DRUG CON- JUGATES AND METHODS", PCT/US2009/031199, filed 16 Jan. 2009, each of which are incorporated by reference.

Conjugates quantization analysis by in-gel fluorescence detection was performed using ProXpress CCD-based scanner (PerkinElmer). Instrument excitation and emission filters were set at 480/30 nm and 590/35 nm respectively. Quantization analysis was performed using Profinder software provided with the instrument using the different amount of starting materials loaded on the gel as reference. Total loaded protein was then evaluated by Coomassie Blue protein staining Example 8

Conjugation of Cysteine Engineered Antibodies and Maleimide Drug-Linker Intermediates After the reduction and reoxidation procedures of Example 6, the cysteine engineered antibody is dissolved in PBS (phosphate buffered saline) buffer and chilled on ice. About 1.5 molar equivalents relative to engineered cysteines per antibody of an anthracycline derivative with a thiol-reactive functional group such as: pyridine-disulfide, e.g. drug-linker intermediates 53 or; bromo-acetamido and maleimide, e.g. drug-linker intermediates 51 and 52, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The reaction mixture is concentrated by centrifugal ultrafiltration and the cysteine engineered antibody-drug conjugate is purified and desalted by elution through G25 resin in PBS, filtered through 0.2 μm filters under sterile conditions, and frozen for storage.

By the procedures above, cysteine engineered antibody drug conjugates were prepared: 102, 103, 104, 105, 106, 107, 108, 109, 111, 112, and 113 (Table 2). Each of the cysteine engineered antibodies comprising antibody-drug conjugates 102, 103, 104, 105, 106, 107, 108, 109, 111, 112, and 113 were the heavy chain (HC) A114C (Kabat) cysteine engineered mutant (U.S. Pat. No. 7,521,541). For the trastuzumab antibody, the A114C mutant by the Kabat numbering scheme is the same as the A118C mutant by the EU numbering scheme and the A121C mutant by the Sequential numbering scheme.

Cysteine engineered antibody drug conjugates with the maleimide caproyl (MC), valine-citrulline (vc), p-aminobenzyloxycarbamoyl (PAB), and auristatin drug (MMAE) drug-linker moieties (106, 111, and 112) were prepared by the method of Example 3 of US 2008/0311134, and Examples 27 and 29 of U.S. Pat. No. 7,498,298, which are incorporated by reference, with drug-linker intermediate MC-vc-PAB-MMAE:

Example 9

In Vitro Cell Proliferation Assay

Tumor cell lines breast carcinoma BT-474, SKBR-3, and MCF7 were obtained from American Type Culture Collection.

The in vitro potency of antibody-drug conjugates was measured by a cell proliferation assay (FIGS. 8-29). The CellTiter-Glo® Luminescent Cell Viability Assay is a commercially available (Promega Corp., Madison, Wis.), homogeneous assay method based on the recombinant expression of *Coleoptera* luciferase (U.S. Pat. No. 5,583,024; U.S. Pat. No. 5,674,713; U.S. Pat. No. 5,700,670). This assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium.

The homogeneous "add-mix-measure" format results in cell lysis and generation of a luminescent signal proportional to the amount of ATP present. The substrate, Beetle Luciferin, is oxidatively decarboxylated by recombinant firefly luciferase with concomitant conversion of ATP to AMP and generation of photons. Viable cells are reflected in relative luminescence units (RLU). Data can be recorded by luminometer or CCD camera imaging device. The luminescence output is presented as RLU, measured over time. Alternatively, photons from luminescence can be counted in a scintillation counter in the presence of a scintillant. The light units can be represented then as CPS—counts per second.

Efficacy of ADC were measured by a cell viability assay employing the following protocol, adapted from CellTiter Glo Luminescent Cell Viability Assay, Promega Corp. Technical Bulletin TB288 and Mendoza et al (2002) Cancer Res. 62:5485-5488:

1. An aliquot of 50 μl of cell culture containing about 1000 or more cells, including:

HER2-expressing and CD22-expressing cells, in medium was deposited in each well of a 96-well, opaque-walled, clear bottom plate.

2. ADC (50 μl) was added to triplicate experimental wells to final concentration of 10 μg/mL, with "no ADC" control wells receiving medium alone, and incubated for 3 or more days.

3. The plates were equilibrated to room temperature for approximately 30 minutes.

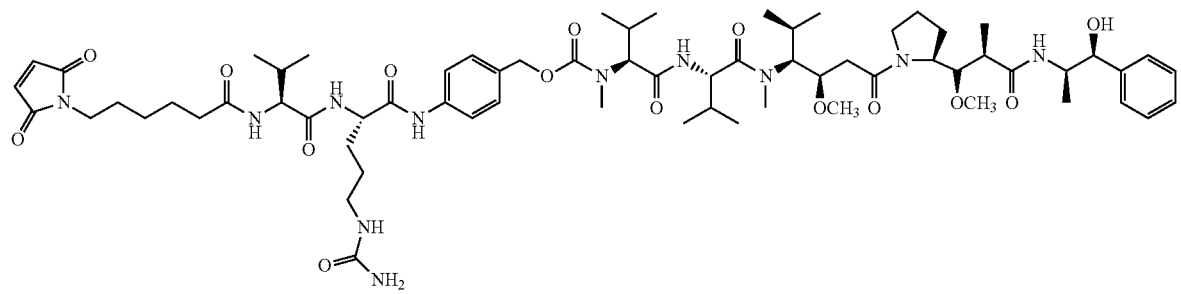

4. CellTiter-Glo Reagent (100 µl) was added.

5. The contents were mixed for 2 minutes on an orbital shaker to induce cell lysis.

6. The plate was incubated at room temperature for 10 minutes to stabilize the luminescence signal.

7. Luminescence was recorded and reported in graphs as RLU=relative luminescence units.

Example 10

Pharmacokinetics—Serum Clearance and Stability

The disposition of antibody-drug conjugates in vivo is analyzed by measuring the serum concentrations of antibody and of drug conjugate after a single intravenous bolus dose into Sprague-Dawley rats. Concentrations of antibody-drug conjugates bearing at least one cytotoxic drug are measured with an ELISA that used a extracellular domain (ECD) protein for the capture and anti-anthracycline and horseradish peroxidase (HRP) conjugated anti-mouse Fc antibody for detection. Total antibody concentrations in serum were measured with an ELISA that uses ECD for capture and anti-human-Fc HRP for detection, measuring antibody, both with and without conjugated anthracycline derivative. The serum concentration-time data from each animal is analyzed using a two-compartment model with IV bolus input, first-order elimination, and macro-rate constants (Model 8, WinNonlin Pro v.5.0.1, Pharsight Corporation, Mountain View, Calif.).

Example 11

Animal Toxicity

A 12 day acute toxicity study in adolescent female rats (100-125 gms) is conducted by a single injection of antibody-drug conjugate at about 1-10 mg/kg, and a control Vehicle at day 1. Injection of test article is typically administered as an intravenous bolus. Body weight is measured daily. Clinical chemistry, serum enzymes and hematology analysis is conducted periodically. Toxicity signals included the clinical observation of weight loss.

Example 12

Tumor Growth Inhibition, In Vivo Efficacy Mouse Model

All animal studies were performed in compliance with NIH guidelines for the care and use of laboratory animals and were approved by the Institutional Animal Care and Use Committee at Genentech.

Efficacy studies were performed using SCID mice (Charles River Laboratories). The efficacy models for the studies exemplified in FIGS. 30-32 were employed as described (Polson et al (2009) Cancer Res. 69(6):2358-2364; Phillips et al (2008) Cancer Res. 68(22):9280-9290; US 2008/0050310; US 2005/0276812), evaluating tumor volume after a single intravenous dose. Transplant models were developed using tumors excised from a mouse bearing an intraperitoneal tumor, then serially passaged into recipient mice. For example, cells for implantation were washed and suspended in HBSS (Hyclone) and inoculated subcutaneously into the flanks of female CB17 ICR severe combined immunodeficiency mice (7-16 weeks of age from Charles Rivers Laboratories), in a volume of 0.2 mL/mouse. To test the efficacy of the antibody drug conjugates in vivo, approximately several million cells per SCID mouse were inoculated once and allowed to grow for about 10 to 60 days post-injection. When tumor volumes reached 150-200 mm$^3$ (typically Day 14 to Day 21 after inoculation), the mice were segregated into sample groups of 9-10 mice per group and the tumor volume was determined in each mouse. When mean tumor size reached the desired volume, the mice were divided into groups of 8 to 10 mice with the same mean tumor size and dosed intravenously via the tail vein with samples: ADCs, antibodies, or Vehicle. ADC doses were either measured as the mass of the conjugated cytotoxic small molecule drug per surface area of the mouse, or as a constant mass of ADC per mass of the mouse (e.g., 5 mg of ADC/kg mouse). In general, the drug loads on the antibodies in any given experiment were similar or normalized, so these two measures could be considered equivalent. Tumor volume was measured using calipers according to the formula: V (mm$^3$)=0.5A×B$^2$, where A and B are the long and short diameters, respectively. Mice were euthanized before tumor volume reached 3000 mm$^3$ or when tumors showed signs of impending ulceration. Data collected from each experimental group were expressed as mean±SE.

The invention claimed is:

1. An anthracycline derivative of formula (IIc)

$$\text{Ant-L-(Z)}_m\text{—X} \qquad \text{(IIc)}$$

wherein Ant has the structure:

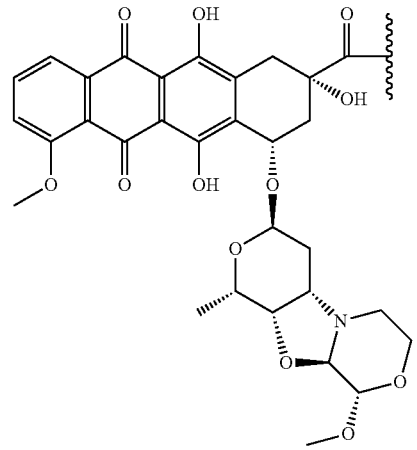 [SMILES: *C(=O)[C@]1(O)Cc2c(O)c3c(c(O)c2[C@@H](O[C@H]2C[C@H]4[C@H](O[C@@H]5[C@@H](OC)OCCN54)[C@H](C)O2)C1)C(=O)c1c(OC)cccc1C3=O]

where the wavy line indicates the attachment to L;

L is a linker selected from —CH$_2$O—, —N(R)$_m$(C$_1$-C$_{12}$ alkylene)-X$^1$, —N(R)—, —N(R)$_m$(C$_1$-C$_{12}$ alkylene)-, —N(R)$_m$(C$_2$-C$_8$ alkenylene)-, —N(R)$_m$(C$_2$-C$_8$ alkynylene)-, —N(R)$_m$(CH$_2$CH$_2$O)$_n$—, and the structures:

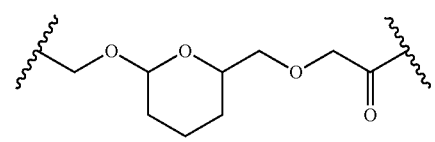

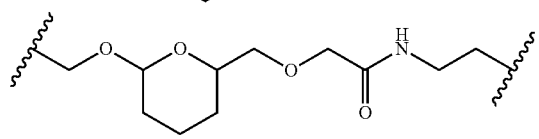

-continued

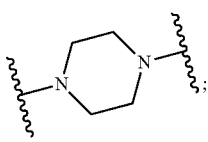

where the wavy lines indicate the attachments to Ant and Z; and

Z is an optional spacer selected from —CH₂C(O)—, —CH₂C(O)NR(C₁-C₁₂ alkylene)-, and the structures:

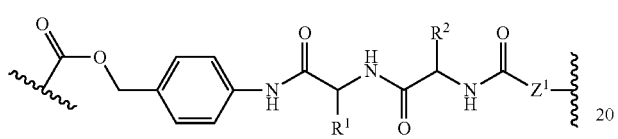

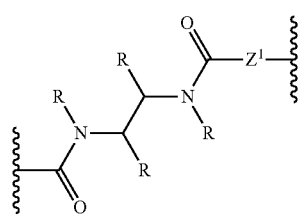

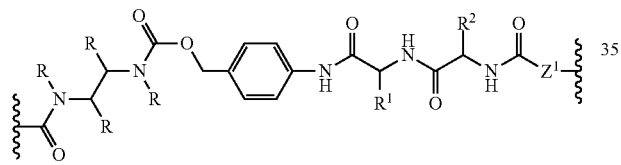

X is a reactive functional group selected from maleimide, thiol, amino, bromide, p-toluenesulfonate, iodide, hydroxyl, carboxyl, pyridyl disulfide, and N-hydroxysuccinimide;

R is H, $C_1$-$C_{12}$ alkyl, or $C_6$-$C_{20}$ aryl;

$R^1$ and $R^2$ are independently selected from an amino acid side chain;

$Z^1$ is selected from —S—, —CH₂C(O)—, —(CH₂CH₂O)$_n$CH₂C(O)—, —(CH₂CH₂O)$_n$CH₂— and —(C₁-C₁₂ alkylene)-;

m is 0 or 1; and n is 1 to 6.

2. The anthracycline derivative of claim 1 selected from the structures:

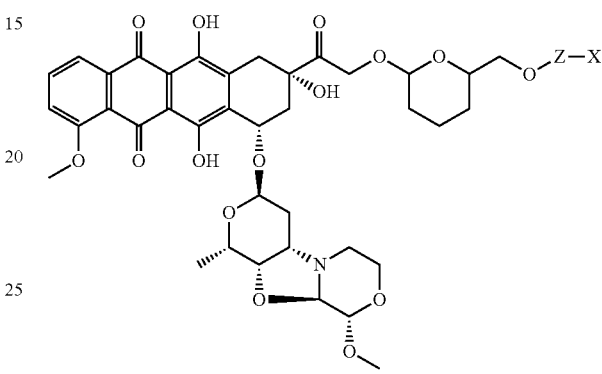

wherein Z—X is selected from:

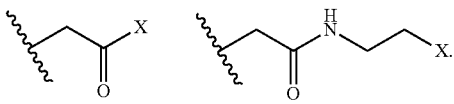

3. The anthracycline derivative of claim 2 having the structure:

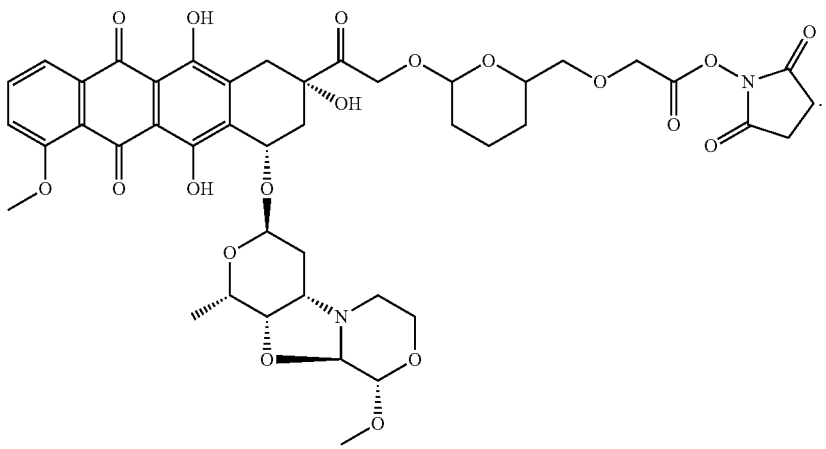 [SMILES: COc1cccc2c1C(=O)c1c(O)c3c(c(O)c1C2=O)C[C@@](O)(C(=O)COC1CCCC(COCC(=O)ON2C(=O)CCC2=O)O1)C[C@@H]3O[C@H]1C[C@H]2[C@H](O[C@@H]3[C@@H](OC)OCCN32)[C@H](C)O1]

4. The anthracycline derivative of claim 2 having the structure:
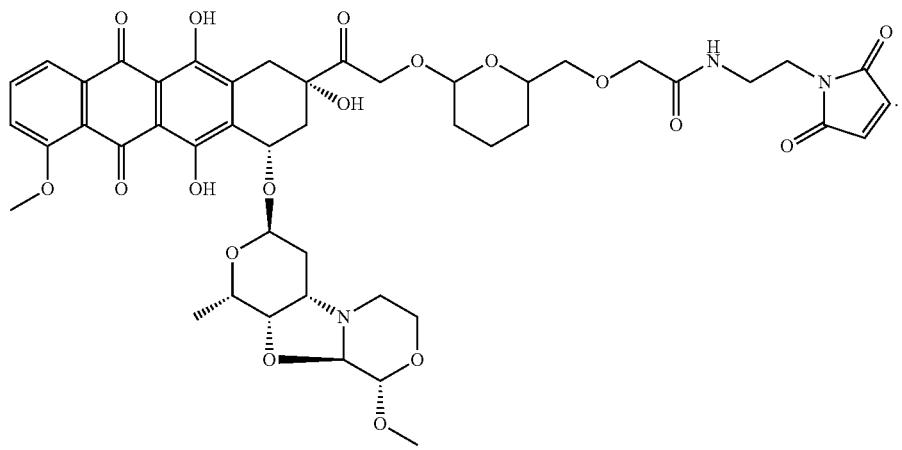 [SMILES: COc1cccc2c1C(=O)c1c(O)c3c(c(O)c1C2=O)C[C@@](O)(C(=O)COC1CCCC(COCC(=O)NCCN2C(=O)C=CC2=O)O1)C[C@@H]3O[C@H]1C[C@H]2[C@H](O[C@@H]3[C@@H](OC)OCCN32)[C@H](C)O1]
5. The anthracycline derivative of claim 1 having the structure:
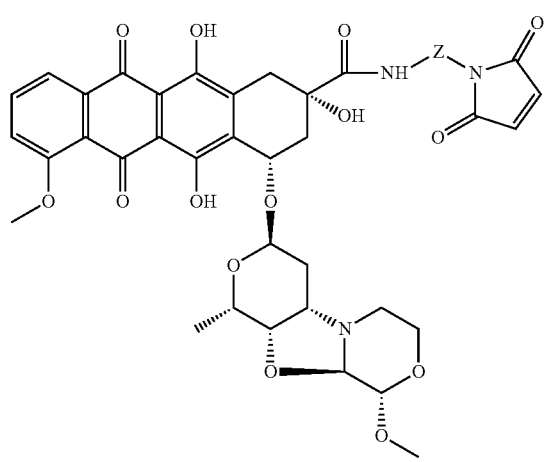
where Z is $C_1$-$C_{12}$ alkylene.
6. The anthracycline derivative of claim 5 having the structure:
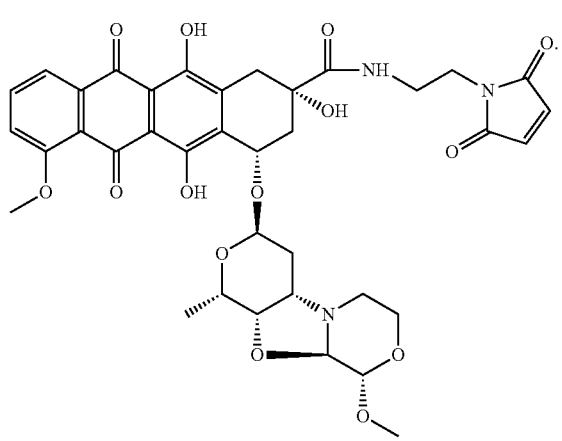 [SMILES: COc1cccc2c1C(=O)c1c(O)c3c(c(O)c1C2=O)C[C@@](O)(C(=O)NCCN1C(=O)C=CC1=O)C[C@@H]3O[C@H]1C[C@H]2[C@H](O[C@@H]3[C@@H](OC)OCCN32)[C@H](C)O1]
7. The anthracycline derivative of claim 1 having the structure:
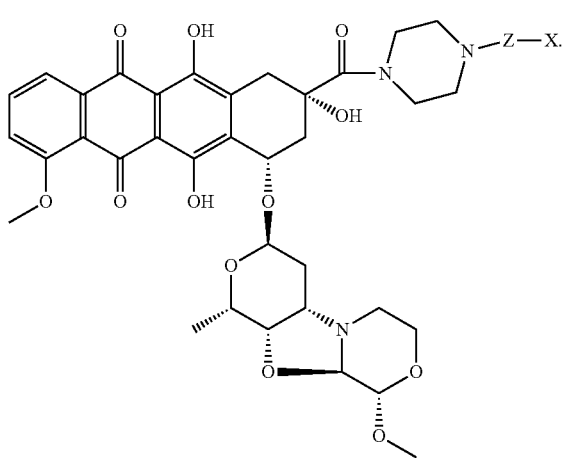
8. The anthracycline derivative of claim 7 having the structure:
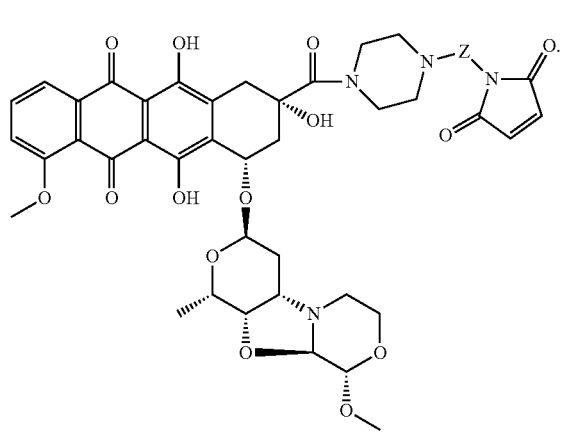

9. The anthracycline derivative of claim 7 having the structure:
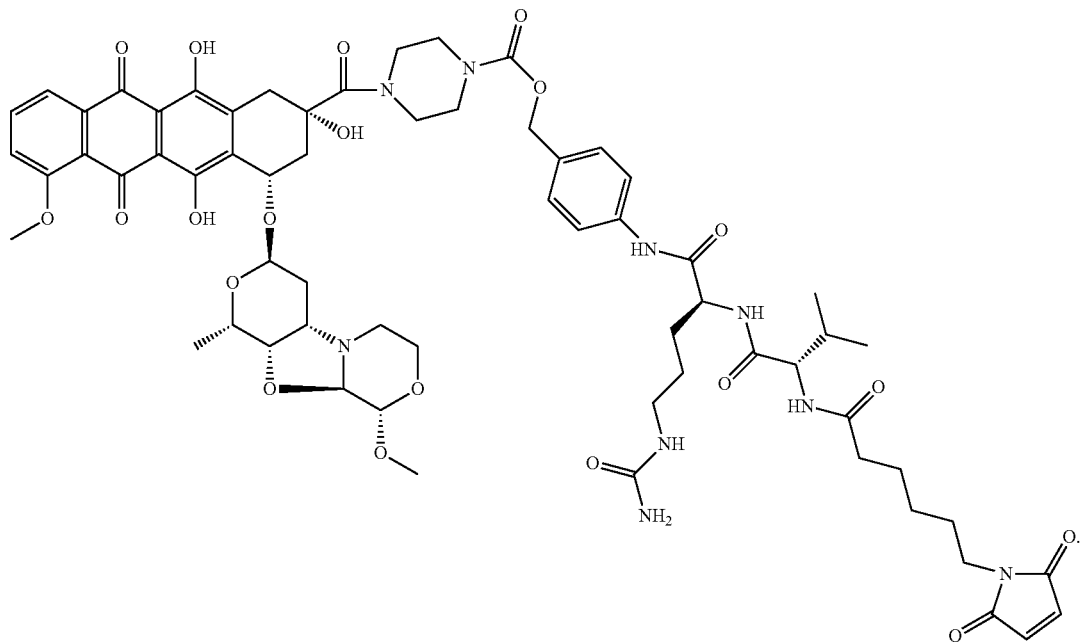 [SMILES: COc1cccc2c1C(=O)c1c(O)c3c(c(O)c1C2=O)C[C@@](O)(C(=O)N1CCN(C(=O)OCc2ccc(NC(=O)[C@H](CCCNC(N)=O)NC(=O)[C@@H](NC(=O)CCCCCN4C(=O)C=CC4=O)C(C)C)cc2)CC1)C[C@@H]3O[C@H]1C[C@H]2[C@H](O[C@@H]3[C@@H](OC)OCCN32)[C@H](C)O1]
10. The anthracycline derivative of claim 7 selected from the structures:
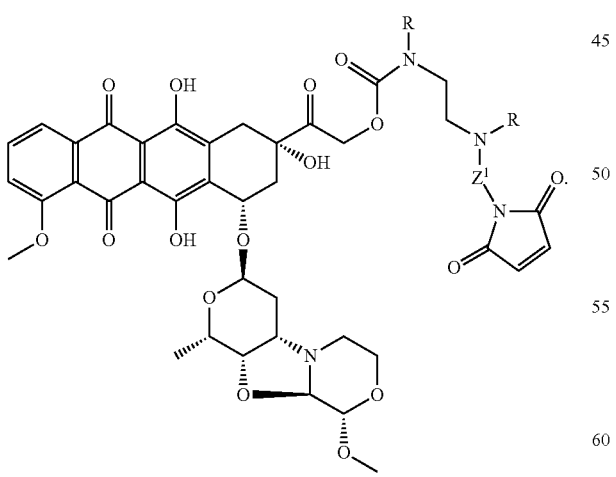
11. The anthracycline derivative of claim 10 wherein $Z^1$ is —($C_1$-$C_{12}$ alkylene)-.

12. The anthracycline derivative of claim 10 having the structure:

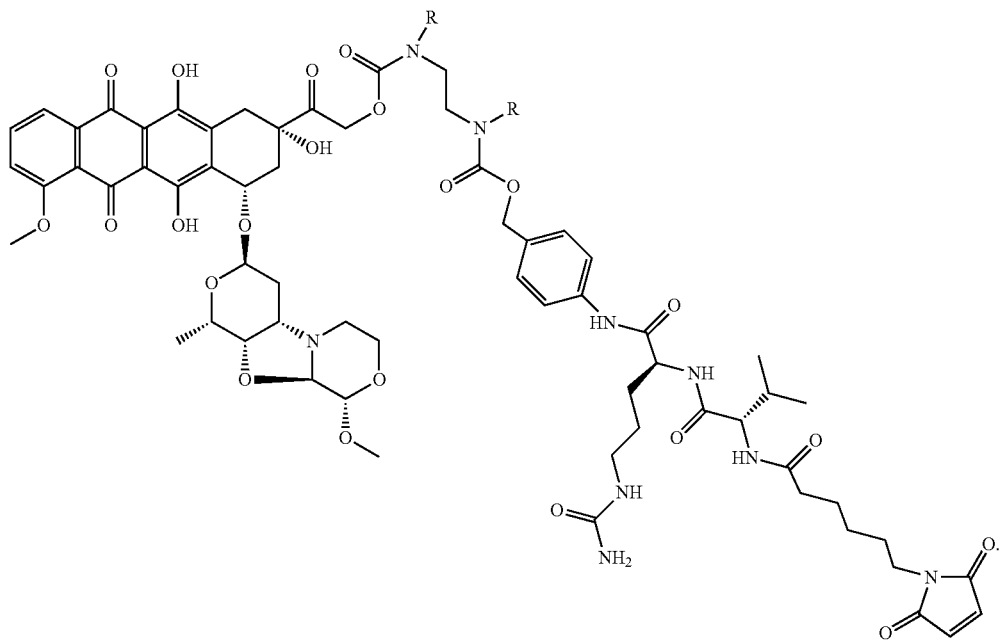

13. The anthracycline derivative of claim 1 wherein $R^1$ and $R^2$ are independently selected from hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$—(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl, and the following structures:

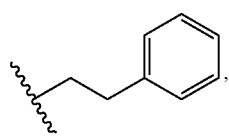

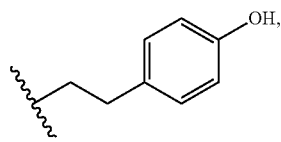

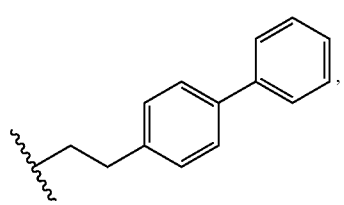

-continued

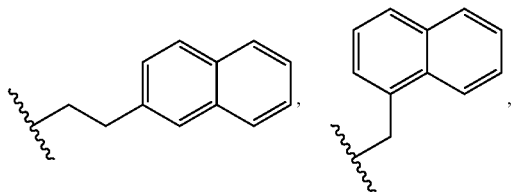

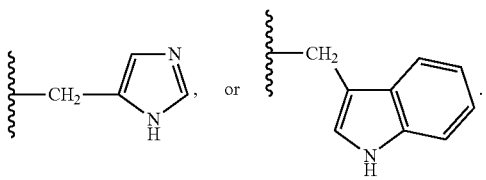

14. The anthracycline derivative of claim 1 selected from the structures:
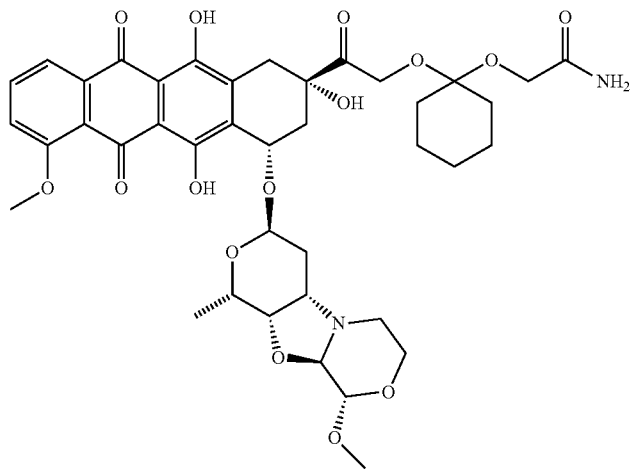
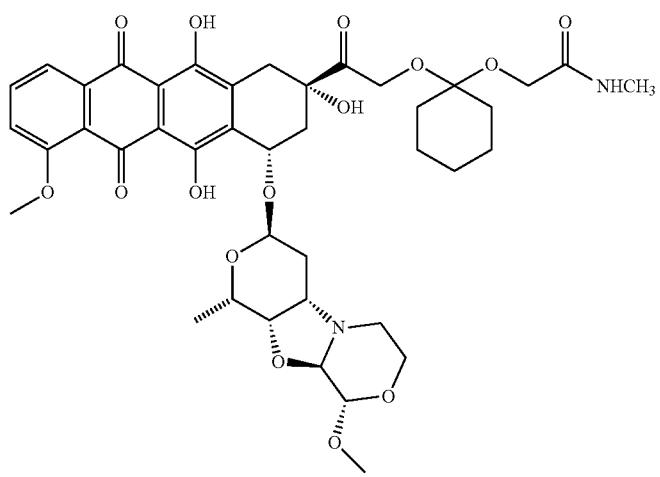
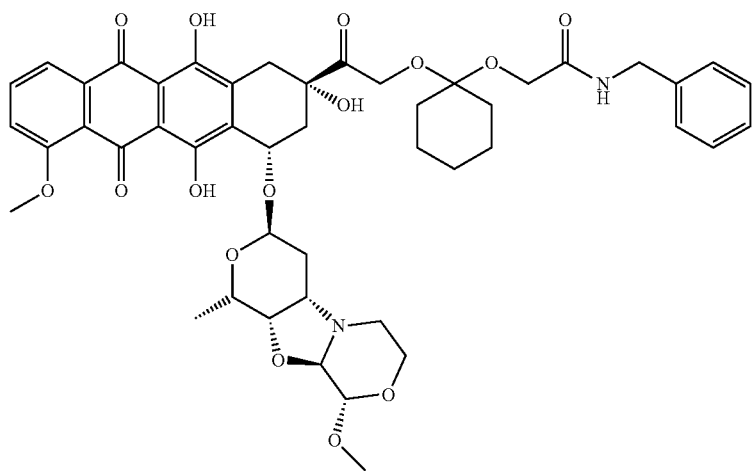

-continued
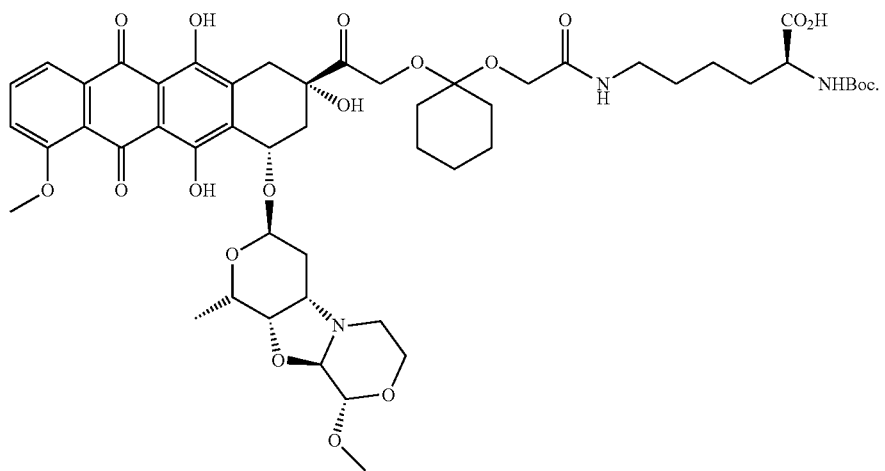
15. The anthracycline derivative of claim 1 selected from the structures:
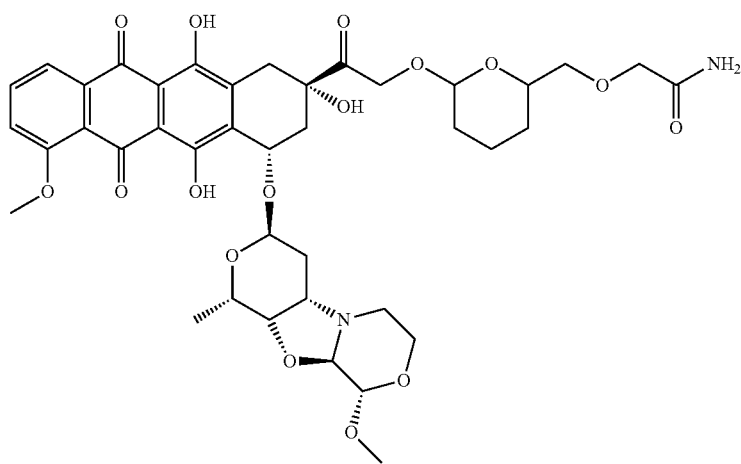
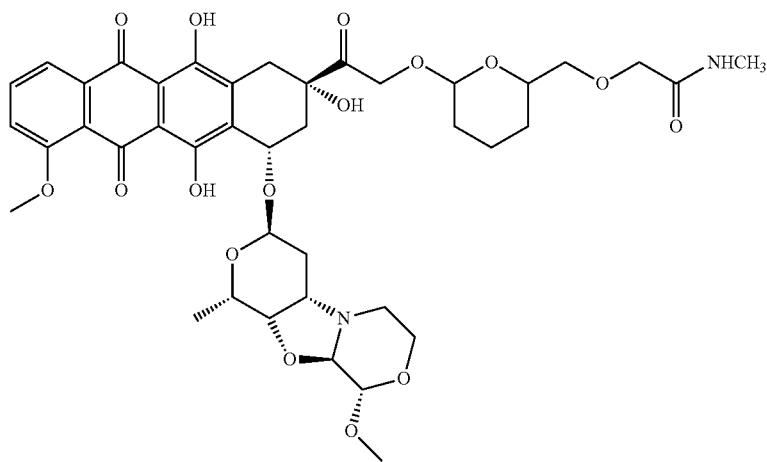

-continued
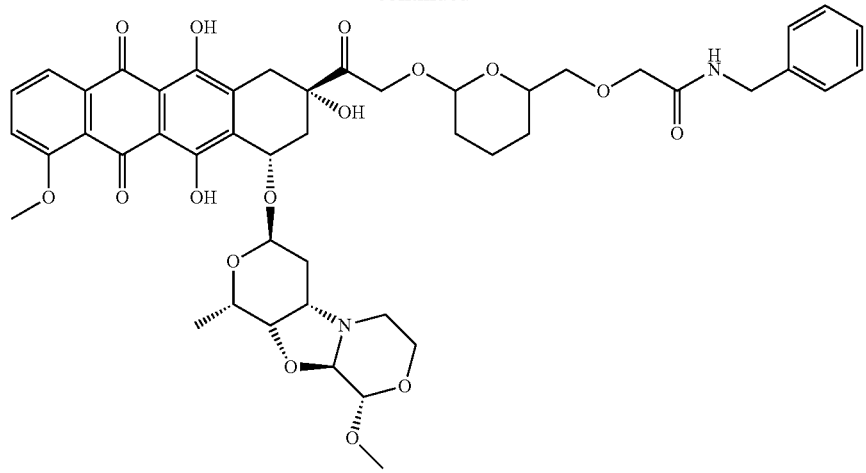
* * * * *

UNITED STATES PATENT AND TRADEMARK OFFICE
CERTIFICATE OF CORRECTION

| | | |
|---|---|---|
| PATENT NO. | : 8,389,697 B2 | Page 1 of 1 |
| APPLICATION NO. | : 13/360212 | |
| DATED | : March 5, 2013 | |
| INVENTOR(S) | : Beria et al. | |

It is certified that error appears in the above-identified patent and that said Letters Patent is hereby corrected as shown below:

On the Title page,

(73) Assignee: Genentech, Inc., South San Francisco, CA (US)

Please add Nerviano Medical Sciences SRL, Milano, Italy, as co-Assignee.

Signed and Sealed this
Twenty-sixth Day of January, 2016

Michelle K. Lee
*Director of the United States Patent and Trademark Office*